(12) United States Patent
Deschenes et al.

(10) Patent No.: US 12,102,635 B2
(45) Date of Patent: Oct. 1, 2024

(54) METHODS OF USING PROTEIN PALMITOYLATIONS INHIBITORS

(71) Applicants: University of South Florida, Tampa, FL (US); The Florida International University Board of Trustees, Miami, FL (US)

(72) Inventors: Robert Deschenes, Tampa, FL (US); Arunava Roy, Tampa, FL (US); Ahmed Ramadan, Tampa, FL (US); Subhra Mohapatra, Tampa, FL (US); Marcello Giulianotti, Miami, FL (US)

(73) Assignees: University of South Florida, Tampa, FL (US); The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 17/938,531

(22) Filed: Oct. 6, 2022

(65) Prior Publication Data

US 2023/0135119 A1    May 4, 2023

Related U.S. Application Data

(60) Provisional application No. 63/262,147, filed on Oct. 6, 2021.

(51) Int. Cl.
*A61K 31/496* (2006.01)
*A61P 31/14* (2006.01)

(52) U.S. Cl.
CPC ............ *A61K 31/496* (2013.01); *A61P 31/14* (2018.01)

(58) Field of Classification Search
CPC .................................................. A61K 31/496
See application file for complete search history.

(56) References Cited

PUBLICATIONS

Abdulrahman DA, Meng X, Veit M. 2021. S-Acylation of Proteins of Coronavirus and Influenza Virus: Conservation of Acylation Sites in Animal Viruses and DHHC Acyltransferases in Their Animal Reservoirs. Pathogens 10.
Bentz J, Mittal A. 2003. Architecture of the influenza hemagglutinin membrane fusion site. Biochim Biophys Acta 1614:24-35.
Blanc M, David FPA, van der Goot FG. 2019. SwissPalm 2: Protein S-Palmitoylation Database. Methods Mol Biol 2009:203-214.
Cai Y, Zhang J, Xiao T, Peng H, Sterling SM, Walsh RM, Jr., Rawson S, Rits-Volloch S, Chen B. 2020. Distinct conformational states of SARS-CoV-2 spike protein. Science 369:1586-1592.
Chang KW, Sheng Y, Gombold JL. 2000. Coronavirus-induced membrane fusion requires the cysteine-rich domain in the spike protein. Virology 269:212-24.
Chase JF, Tubbs PK. 1972. Specific inhibition of mitochondrial fatty acid oxidation by 2-bromopalmitate and its coenzyme A and carnitine esters. Biochem J 129:55-65.
Chavda B, Arnott JA, Planey SL. 2014. Targeting protein palmitoylation: selective inhibitors and implications in disease. Expert Opin Drug Discov 9:1005-19.
Chen JJ, Marsden AN, Scott CA, Akimzhanov AM, Boehning D. 2020. DHHC5 Mediates beta-Adrenergic Signaling in Cardiomyocytes by Targeting Galpha Proteins. Biophys J 118:826-835.
Coleman RA, Rao P, Fogelsong RJ, Bardes ES. 1992. 2-Bromopalmitoyl-CoA and 2-bromopalmitate: promiscuous inhibitors of membrane-bound enzymes. Biochim Biophys Acta 1125:203-9.
Corman VM, Landt O, Kaiser M, Molenkamp R, Meijer A, Chu DK, Bleicker T, Brunink S, Schneider J, Schmidt ML, Mulders DG, Haagmans BL, van der Veer B, van den Brink S, Wijsman L, Goderski G, Romette JL, Ellis J, Zambon M, Peiris M, Goossens H, Reusken C, Koopmans MP, Drosten C. 2020. Detection of 2019 novel coronavirus (2019-nCoV) by real-time RT-PCR. Euro Surveill 25.
Coutard B, Valle C, de Lamballerie X, Canard B, Seidah NG, Decroly E. 2020. The spike glycoprotein of the new coronavirus 2019-nCoV contains a furin-like cleavage site absent in CoV of the same clade. Antiviral Res 176:104742.
Crawford KHD, Eguia R, Dingens AS, Loes AN, Malone KD, Wolf CR, Chu HY, Tortorici MA, Veesler D, Murphy M, Pettie D, King NP, Balazs AB, Bloom JD. 2020. Protocol and Reagents for Pseudotyping Lentiviral Particles with SARS-CoV-2 Spike Protein for Neutralization Assays. Viruses 12.
Dai L, Gao GF. 2021. Viral targets for vaccines against COVID-19. Nat Rev Immunol 21:73-82.
Davda D, El Azzouny MA, Tom CT, Hernandez JL, Majmudar JD, Kennedy RT, Martin BR. 2013. Profiling targets of the irreversible palmitoylation inhibitor 2-bromopalmitate. ACS Chem Biol 8:1912-7.
Draper JM, Smith CD. 2009. Palmitoyl acyltransferase assays and inhibitors (Review). Mol Membr Biol 26:5-13.
Duan L, Zheng Q, Zhang H, Niu Y, Lou Y, Wang H. 2020. The SARS-CoV-2 Spike Glycoprotein Biosynthesis, Structure, Function, and Antigenicity: Implications for the Design of Spike-Based Vaccine Immunogens. Front Immunol 11:576622.
Dull T, Zufferey R, Kelly M, Mandel RJ, Nguyen M, Trono D, Naldini L. 1998. A third-generation lentivirus vector with a conditional packaging system. J Virol 72:8463-71.
Fredriksson S, Gullberg M, Jarvius J, Olsson C, Pietras K, Gustafsdottir SM, Ostman A, Landegren U. 2002. Protein detection using proximity-dependent DNA ligation assays. Nat Biotechnol 20:473-7.
Gadalla MR, Veit M. 2020. Toward the identification of ZDHHC enzymes required for palmitoylation of viral protein as potential drug targets. Expert Opin Drug Discov 15:159-177.

(Continued)

*Primary Examiner* — Paul V Ward
(74) *Attorney, Agent, or Firm* — Meunier Carlin & Curfman LLC

(57) ABSTRACT

The present disclosure relates to methods of using palmitoylation inhibitors for reducing or treating enveloped virus infections.

14 Claims, 30 Drawing Sheets

Specification includes a Sequence Listing.

(56) References Cited

PUBLICATIONS

Gordon DE, et al. 2020. A SARS-CoV-2 protein interaction map reveals targets for drug repurposing. Nature 583:459-468.

Gottlieb CD, Linder ME. 2017. Structure and function of DHHC protein S-acyltransferases. Biochem Soc Trans 45:923-8.

Hamel LD, Lenhart BJ, Mitchell DA, Santos RG, Giulianotti MA, Deschenes RJ. 2016. Identification of Protein Palmitoylation Inhibitors from a Scaffold Ranking Library. Comb Chem High Throughput Screen 19:262-74.

Hoffmann M, Kleine-Weber H, Pohlmann S. 2020. A Multibasic Cleavage Site in the Spike Protein of SARS-CoV-2 Is Essential for Infection of Human Lung Cells. Mol Cell 78:779-784 e5.

Hoffmann M, Kleine-Weber H, Schroeder S, Kruger N, Herrler T, Erichsen S, Schiergens TS, Herrler G, Wu NH, Nitsche A, Muller MA, Drosten C, Pohlmann S. 2020. SARS-CoV-2 Cell Entry Depends on ACE2 and TMPRSS2 and Is Blocked by a Clinically Proven Protease Inhibitor. Cell 181:271-280 e8.

Hogue IB, Bosse JB, Hu JR, Thiberge SY, Enquist LW. 2014. Cellular mechanisms of alpha herpesvirus egress: live cell fluorescence microscopy of pseudorabies virus exocytosis. PLoS Pathog 10:e1004535.

Huang Y, Yang C, Xu XF, Xu W, Liu SW. 2020. Structural and functional properties of SARS-CoV-2 spike protein: potential antivirus drug development for COVID-19. Acta Pharmacol Sin 41:1141-1149.

Iwanaga T, Tsutsumi R, Noritake J, Fukata Y, Fukata M. 2009. Dynamic protein palmitoylation in cellular signaling. Prog Lipid Res 48:117-27.

Jiang H, Zhang X, Chen X, Aramsangtienchai P, Tong Z, Lin H. 2018. Protein Lipidation: Occurrence, Mechanisms, Biological Functions, and Enabling Technologies. Chem Rev 118:919-988.

Lee M, Sugiyama M, Mekhail K, Latreille E, Khosraviani N, Wei K, Lee WL, Antonescu C, Fairn GD. 2020. Fatty Acid Synthase inhibition prevents palmitoylation of SARS-CoV2 Spike Protein and improves survival of mice infected with murine hepatitis virus. bioRxiv doi: 10.1101/2020.12.20.423603:2020.12.20.423603.

Li D, Liu Y, Lu Y, Gao S, Zhang L. 2021. Palmitoylation of SARS-CoV-2 S protein is critical for S-mediated syncytia formation and virus entry. J Med Virol doi:10.1002/jmv.27339.

Linder ME, Deschenes RJ. 2007. Palmitoylation: policing protein stability and traffic. Nat Rev Mol Cell Biol 8:74-84.

Lobo S, Greentree WK, Linder ME, Deschenes RJ. 2002. Identification of a Ras palmitoyltransferase in Saccharomyces cerevisiae. J Biol Chem 277:41268-73.

Lontok E, Corse E, Machamer CE. 2004. Intracellular targeting signals contribute to localization of coronavirus spike proteins near the virus assembly site. J Virol 78:5913-22.

Luo Z, Matthews AM, Weiss SR. 1999. Amino acid substitutions within the leucine zipper domain of the murine coronavirus spike protein cause defects in oligomerization and the ability to induce cell-to-cell fusion. J Virol 73:8152-9.

McBride CE, Machamer CE. 2010. Palmitoylation of SARS-CoV S protein is necessary for partitioning into detergent-resistant membranes and cell-cell fusion but not interaction with M protein. Virology 405:139-48.

McClafferty H, Shipston MJ. 2019. siRNA Knockdown of Mammalian zDHHCs and Validation of mRNA Expression by rt-qPCR. Methods Mol Biol 2009:151-168.

Mesquita FS, Abrami L, Sergeeva O, Turelli P, Qing E, Kunz B, Raclot C, Paz Montoya J, Abriata LA, Gallagher T, Dal Peraro M, Trono D, D'Angelo G, van der Goot FG. 2021. S-acylation controls SARS-CoV-2 membrane lipid organization and enhances infectivity. Dev Cell doi:10.1016/j.devcel.2021.09.016.

Mitchell DA, Vasudevan A, Linder ME, Deschenes RJ. 2006. Protein palmitoylation by a family of DHHC protein S-acyltransferases. J Lipid Res 47:1118-27.

Myhill N, Lynes EM, Nanji JA, Blagoveshchenskaya AD, Fei H, Carmine Simmen K, Cooper TJ, Thomas G, Simmen T. 2008. The subcellular distribution of calnexin is mediated by PACS-2. Mol Biol Cell 19:2777-88.

Ohta E, Misumi Y, Sohda M, Fujiwara T, Yano A, Ikehara Y. 2003. Identification and characterization of GCP16, a novel acylated Golgi protein that interacts with GCP170. J Biol Chem 278:51957-67.

Pedro MP, Vilcaes AA, Tomatis VM, Oliveira RG, Gomez GA, Daniotti JL. 2013. 2-Bromopalmitate reduces protein deacylation by inhibition of acyl-protein thioesterase enzymatic activities. PLoS One 8:e75232.

Percher A, Thinon E, Hang H. 2017. Mass-Tag Labeling Using Acyl-PEG Exchange for the Determination of Endogenous Protein S-Fatty Acylation. Curr Protoc Protein Sci 89:14 17 1-14 17 11.

Petit CM, Chouljenko VN, Iyer A, Colgrove R, Farzan M, Knipe DM, Kousoulas KG. 2007. Palmitoylation of the cysteine-rich endodomain of the SARS-coronavirus spike glycoprotein is important for spike-mediated cell fusion. Virology 360:264-74.

Puthenveetil R, Lun CM, Murphy RE, Healy LB, Vilmen G, Christenson ET, Freed EO, Banerjee A. 2021. S-acylation of SARS-CoV-2 Spike Protein: Mechanistic Dissection, In Vitro Reconstitution and Role in Viral Infectivity. J Biol Chem doi:10.1016/j.jbc.2021.101112:101112.

Qing E, Kicmal T, Kumar B, Hawkins GM, Timm E, Perlman S, Gallagher T. 2021. Dynamics of SARS-CoV-2 Spike Proteins in Cell Entry: Control Elements in the Amino-Terminal Domains. mBio doi:10.1128/mBio.01590-21:e0159021.

Ren J, Wen L, Gao X, Jin C, Xue Y, Yao X. 2008. CSS-Palm 2.0: an updated software for palmitoylation sites prediction. Protein Eng Des Sel 21:639-44.

Rodenburg RNP, Snijder J, van de Waterbeemd M, Schouten A, Granneman J, Heck AJR, Gros P. 2017. Stochastic palmitoylation of accessible cysteines in membrane proteins revealed by native mass spectrometry. Nat Commun 8:1280.

Roth AF, Feng Y, Chen L, Davis NG. 2002. The yeast DHHC cysteine-rich domain protein Akr1p is a palmitoyl transferase. J Cell Biol 159:23-8.

Sanders DW, Jumper CC, Ackerman PJ, Bracha D, Donlic A, Kim H, Kenney D, Castello-Serrano I, Suzuki S, Tamura T, Tavares AH, Saeed M, Holehouse AS, Ploss A, Levental I, Douam F, Padera RF, Levy BD, Brangwynne CP. 2021. SARS-CoV-2 requires cholesterol for viral entry and pathological syncytia formation. Elife 10.

Santos-Beneit F, Raskevicius V, Skeberdis VA, Bordel S. 2021. A metabolic modeling approach reveals promising therapeutic targets and antiviral drugs to combat COVID-19. Sci Rep 11:11982.

Scudellari M. 2021. How the coronavirus infects cells—and why Delta is so dangerous. Nature 595:640-644.

Shulla A, Gallagher T. 2009. Role of spike protein endodomains in regulating coronavirus entry. J Biol Chem 284:32725-34.

Stertz S, Reichelt M, Spiegel M, Kuri T, Martinez-Sobrido L, Garcia-Sastre A, Weber F, Kochs G. 2007. The intracellular sites of early replication and budding of SARS-coronavirus. Virology 361:304-15.

Swarthout JT, Lobo S, Farh L, Croke MR, Greentree WK, Deschenes RJ, Linder ME. 2005. DHHC9 and GCP16 constitute a human protein fatty acyltransferase with specificity for H- and N-Ras. J Biol Chem 280:31141-8.

Thorp EB, Boscarino JA, Logan HL, Goletz JT, Gallagher TM. 2006. Palmitoylations on murine coronavirus spike proteins are essential for virion assembly and infectivity. J Virol 80:1280-9.

Tsukamoto H, Tousson A, Circolo A, Marchase RB, Volanakis JE. 2002. Calnexin is associated with and induced by overexpressed human complement protein C2. Anat Rec 267:7-16.

Veit M. 2012. Palmitoylation of virus proteins. Biol Cell 104:493-515.

Woodley KT, Collins MO. 2019. S-acylated Golga7b stabilises DHHC5 at the plasma membrane to regulate cell adhesion. EMBO Rep 20:e47472.

Wrapp D, Wang N, Corbett KS, Goldsmith JA, Hsieh CL, Abiona O, Graham BS, McLellan JS. 2020. Cryo-EM structure of the 2019-nCoV spike in the prefusion conformation. Science 367:1260-1263.

(56) References Cited

PUBLICATIONS

Wu Z, Zhang Z, Wang X, Zhang J, Ren C, Li Y, Gao L, Liang X, Wang P, Ma C. 2021. Palmitoylation of SARS-CoV-2 S protein is essential for viral infectivity. Signal Transduct Target Ther 6:231.

Xia S, Lan Q, Su S, Wang X, Xu W, Liu Z, Zhu Y, Wang Q, Lu L, Jiang S. 2020. The role of furin cleavage site in SARS-CoV-2 spike protein-mediated membrane fusion in the presence or absence of trypsin. Signal Transduct Target Ther 5:92.

Xie X, Muruato A, Lokugamage KG, Narayanan K, Zhang X, Zou J, Liu J, Schindewolf C, Bopp NE, Aguilar PV, Plante KS, Weaver SC, Makino S, LeDuc JW, Menachery VD, Shi PY. 2020. An Infectious cDNA Clone of SARS-CoV-2. Cell Host Microbe 27:841-848 e3.

Yang J, Gibson B, Snider J, Jenkins CM, Han X, Gross RW. 2005. Submicromolar concentrations of palmitoyl-CoA specifically thioesterify cysteine 244 in glyceraldehyde-3-phosphate dehydrogenase inhibiting enzyme activity: a novel mechanism potentially underlying fatty acid induced insulin resistance. Biochemistry 44:11903-12.

Yang J, Lv J, Wang Y, Gao S, Yao Q, Qu D, Ye R. 2012. Replication of murine coronavirus requires multiple cysteines in the endodomain of spike protein. Virology 427:98-106.

Zhou T, et al., 2020. Cryo-EM Structures of SARS-CoV-2 Spike without and with ACE2 Reveal a pH-Dependent Switch to Mediate Endosomal Positioning of Receptor-Binding Domains. Cell Host Microbe 28:867-879 e5.

SEQUENCE LISTING

```
Sequence total quantity: 68
SEQ ID NO: 1               moltype = AA  length = 4
FEATURE                    Location/Qualifiers
source                     1..4
                           mol_type = protein
                           organism = Homo sapiens
SEQUENCE: 1
DHHC                                                                        4

SEQ ID NO: 2               moltype = AA  length = 35
FEATURE                    Location/Qualifiers
source                     1..35
                           mol_type = protein
                           organism = Severe acute respiratory syndrome-related
                            coronavirus 2
SEQUENCE: 2
AIVMVTIMLC CMTSCCSCLK GCCSCGSCCK FDEDD                                     35

SEQ ID NO: 3               moltype = AA  length = 35
FEATURE                    Location/Qualifiers
source                     1..35
                           mol_type = protein
                           organism = Severe acute respiratory syndrome-related
                            coronavirus 1
SEQUENCE: 3
AIVMVTILLC CMTSCCSCLK GACSCGSCCK FDEDD                                     35

SEQ ID NO: 4               moltype = AA  length = 35
FEATURE                    Location/Qualifiers
source                     1..35
                           mol_type = protein
                           organism = Bat coronavirus RaTG13
SEQUENCE: 4
AIIMVTIMLC CMTSCCSCLK GCCSCGSCCK FDEDD                                     35

SEQ ID NO: 5               moltype = AA  length = 34
FEATURE                    Location/Qualifiers
source                     1..34
                           mol_type = protein
                           organism = Middle East respiratory syndrome-related
                            coronavirus
SEQUENCE: 5
LALCVFFILC CTGCGTNCMG KLKCNRCCDR YEEY                                      34

SEQ ID NO: 6               moltype = AA  length = 33
FEATURE                    Location/Qualifiers
source                     1..33
                           mol_type = protein
                           organism = Mouse hepatisis virus A59
SEQUENCE: 6
AVCVLLFFIC CCTGCGSCCF KKCGNCCDEY GGH                                       33

SEQ ID NO: 7               moltype = AA  length = 33
FEATURE                    Location/Qualifiers
source                     1..33
                           mol_type = protein
                           organism = Human coronavirus OC43
SEQUENCE: 7
AMLVLLFFIC CCTGCGTSCF KKCGGCCDDY TGY                                       33

SEQ ID NO: 8               moltype = AA  length = 35
FEATURE                    Location/Qualifiers
source                     1..35
                           mol_type = protein
                           organism = Human coronavirus 229E
SEQUENCE: 8
IFVVSMLLLC CCSTGCCGFF SCFASSIRGC CESTK                                     35

SEQ ID NO: 9               moltype = AA  length = 35
FEATURE                    Location/Qualifiers
source                     1..35
                           mol_type = protein
                           organism = Transmissible gastroenteritis virus
SEQUENCE: 9
IFCIPLLLFC CCSTGCCGCI GCLGSCCHSI CSRRQ                                     35

SEQ ID NO: 10              moltype = AA  length = 35
FEATURE                    Location/Qualifiers
```

```
source                    1..35
                          mol_type = protein
                          organism = Avian infectious bronchitis virus
SEQUENCE: 10
LGWVFFMTGC CGCCCGCFGI MPLMSKCGKK SSYYT                            35

SEQ ID NO: 11             moltype = DNA   length = 27
FEATURE                   Location/Qualifiers
source                    1..27
                          mol_type = other DNA
                          organism = synthetic construct
SEQUENCE: 11
tataatgctg agcagcatga caagctg                                    27

SEQ ID NO: 12             moltype = DNA   length = 18
FEATURE                   Location/Qualifiers
source                    1..18
                          mol_type = other DNA
                          organism = synthetic construct
SEQUENCE: 12
gtcaccatga ctatagcg                                              18

SEQ ID NO: 13             moltype = DNA   length = 26
FEATURE                   Location/Qualifiers
source                    1..26
                          mol_type = other DNA
                          organism = synthetic construct
SEQUENCE: 13
agcagtctca aaggctgttg ctcttg                                     26

SEQ ID NO: 14             moltype = DNA   length = 24
FEATURE                   Location/Qualifiers
source                    1..24
                          mol_type = other DNA
                          organism = synthetic construct
SEQUENCE: 14
gctgctgctt gtcatgcagc acag                                       24

SEQ ID NO: 15             moltype = DNA   length = 24
FEATURE                   Location/Qualifiers
source                    1..24
                          mol_type = other DNA
                          organism = synthetic construct
SEQUENCE: 15
tctagcggct cttgctgcaa attc                                       24

SEQ ID NO: 16             moltype = DNA   length = 24
FEATURE                   Location/Qualifiers
source                    1..24
                          mol_type = other DNA
                          organism = synthetic construct
SEQUENCE: 16
gctactgcct ttgagacagc tgca                                       24

SEQ ID NO: 17             moltype = DNA   length = 26
FEATURE                   Location/Qualifiers
source                    1..26
                          mol_type = other DNA
                          organism = synthetic construct
SEQUENCE: 17
ttgcggctct agcagcaaat tcgatg                                     26

SEQ ID NO: 18             moltype = DNA   length = 19
FEATURE                   Location/Qualifiers
source                    1..19
                          mol_type = other DNA
                          organism = synthetic construct
SEQUENCE: 18
gagcaacagc ctttgagac                                             19

SEQ ID NO: 19             moltype = DNA   length = 50
FEATURE                   Location/Qualifiers
source                    1..50
                          mol_type = other DNA
                          organism = synthetic construct
SEQUENCE: 19
aaaggcagta gctctagcgg ctctagcagc aaattcgatg aggacgattc            50

SEQ ID NO: 20             moltype = DNA   length = 49
```

```
FEATURE              Location/Qualifiers
source               1..49
                     mol_type = other DNA
                     organism = synthetic construct
SEQUENCE: 20
gagactgctg ctgctgcttg tcatgctgct cagcattata gtcaccatg              49

SEQ ID NO: 21        moltype = DNA   length = 19
FEATURE              Location/Qualifiers
source               1..19
                     mol_type = other DNA
                     organism = synthetic construct
SEQUENCE: 21
caagccctcc aacaagacg                                               19

SEQ ID NO: 22        moltype = DNA   length = 21
FEATURE              Location/Qualifiers
source               1..21
                     mol_type = other DNA
                     organism = synthetic construct
SEQUENCE: 22
ccaaagccga tcacagcaaa g                                            21

SEQ ID NO: 23        moltype = DNA   length = 21
FEATURE              Location/Qualifiers
source               1..21
                     mol_type = other DNA
                     organism = synthetic construct
SEQUENCE: 23
aacactggcg aacaagttgt g                                            21

SEQ ID NO: 24        moltype = DNA   length = 21
FEATURE              Location/Qualifiers
source               1..21
                     mol_type = other DNA
                     organism = synthetic construct
SEQUENCE: 24
agatgggaag atccttggct g                                            21

SEQ ID NO: 25        moltype = DNA   length = 21
FEATURE              Location/Qualifiers
source               1..21
                     mol_type = other DNA
                     organism = synthetic construct
SEQUENCE: 25
ccacttccga aacattgagc g                                            21

SEQ ID NO: 26        moltype = DNA   length = 20
FEATURE              Location/Qualifiers
source               1..20
                     mol_type = other DNA
                     organism = synthetic construct
SEQUENCE: 26
ccacagccgt cacggataaa                                              20

SEQ ID NO: 27        moltype = DNA   length = 21
FEATURE              Location/Qualifiers
source               1..21
                     mol_type = other DNA
                     organism = synthetic construct
SEQUENCE: 27
cctgacttgt ggaaccaatc c                                            21

SEQ ID NO: 28        moltype = DNA   length = 22
FEATURE              Location/Qualifiers
source               1..22
                     mol_type = other DNA
                     organism = synthetic construct
SEQUENCE: 28
gcacctcacg ttctttggaa ac                                           22

SEQ ID NO: 29        moltype = DNA   length = 19
FEATURE              Location/Qualifiers
source               1..19
                     mol_type = other DNA
                     organism = synthetic construct
SEQUENCE: 29
cacctgccgc ttttaccgt                                               19
```

```
SEQ ID NO: 30           moltype = DNA   length = 23
FEATURE                 Location/Qualifiers
source                  1..23
                        mol_type = other DNA
                        organism = synthetic construct
SEQUENCE: 30
cggcgaccaa tacagttatt cac                                              23

SEQ ID NO: 31           moltype = DNA   length = 21
FEATURE                 Location/Qualifiers
source                  1..21
                        mol_type = other DNA
                        organism = synthetic construct
SEQUENCE: 31
agtctgccaa gcatacaagg c                                                21

SEQ ID NO: 32           moltype = DNA   length = 23
FEATURE                 Location/Qualifiers
source                  1..23
                        mol_type = other DNA
                        organism = synthetic construct
SEQUENCE: 32
ccagtggtgc taaaaggaga aac                                              23

SEQ ID NO: 33           moltype = DNA   length = 20
FEATURE                 Location/Qualifiers
source                  1..20
                        mol_type = other DNA
                        organism = synthetic construct
SEQUENCE: 33
ctgaccgggt ctggttcatc                                                  20

SEQ ID NO: 34           moltype = DNA   length = 21
FEATURE                 Location/Qualifiers
source                  1..21
                        mol_type = other DNA
                        organism = synthetic construct
SEQUENCE: 34
catgacgaaa gtcaccacga a                                                21

SEQ ID NO: 35           moltype = DNA   length = 21
FEATURE                 Location/Qualifiers
source                  1..21
                        mol_type = other DNA
                        organism = synthetic construct
SEQUENCE: 35
gtatccaggt ccgcatgaag t                                                21

SEQ ID NO: 36           moltype = DNA   length = 19
FEATURE                 Location/Qualifiers
source                  1..19
                        mol_type = other DNA
                        organism = synthetic construct
SEQUENCE: 36
agcgtggttc agcacgtag                                                   19

SEQ ID NO: 37           moltype = DNA   length = 20
FEATURE                 Location/Qualifiers
source                  1..20
                        mol_type = other DNA
                        organism = synthetic construct
SEQUENCE: 37
cccaggcagg aacacctttt                                                  20

SEQ ID NO: 38           moltype = DNA   length = 19
FEATURE                 Location/Qualifiers
source                  1..19
                        mol_type = other DNA
                        organism = synthetic construct
SEQUENCE: 38
ccgaggaatc actccaggg                                                   19

SEQ ID NO: 39           moltype = DNA   length = 20
FEATURE                 Location/Qualifiers
source                  1..20
                        mol_type = other DNA
                        organism = synthetic construct
SEQUENCE: 39
ggtgcagacc ctgatagtcg                                                  20
```

```
SEQ ID NO: 40            moltype = DNA   length = 22
FEATURE                  Location/Qualifiers
source                   1..22
                         mol_type = other DNA
                         organism = synthetic construct
SEQUENCE: 40
gcacgtatgg atctttcctc ac                                                  22

SEQ ID NO: 41            moltype = DNA   length = 20
FEATURE                  Location/Qualifiers
source                   1..20
                         mol_type = other DNA
                         organism = synthetic construct
SEQUENCE: 41
gtgctgacct ggggaatcac                                                     20

SEQ ID NO: 42            moltype = DNA   length = 19
FEATURE                  Location/Qualifiers
source                   1..19
                         mol_type = other DNA
                         organism = synthetic construct
SEQUENCE: 42
ctgcacattc acgtagcca                                                      19

SEQ ID NO: 43            moltype = DNA   length = 22
FEATURE                  Location/Qualifiers
source                   1..22
                         mol_type = other DNA
                         organism = synthetic construct
SEQUENCE: 43
accccactct tattgatgga ga                                                  22

SEQ ID NO: 44            moltype = DNA   length = 22
FEATURE                  Location/Qualifiers
source                   1..22
                         mol_type = other DNA
                         organism = synthetic construct
SEQUENCE: 44
tgtctgccca tttacatctg tc                                                  22

SEQ ID NO: 45            moltype = DNA   length = 22
FEATURE                  Location/Qualifiers
source                   1..22
                         mol_type = other DNA
                         organism = synthetic construct
SEQUENCE: 45
tgtgataact gcgtagaacg gt                                                  22

SEQ ID NO: 46            moltype = DNA   length = 21
FEATURE                  Location/Qualifiers
source                   1..21
                         mol_type = other DNA
                         organism = synthetic construct
SEQUENCE: 46
cgtgggtgat aacgaatgca a                                                   21

SEQ ID NO: 47            moltype = DNA   length = 21
FEATURE                  Location/Qualifiers
source                   1..21
                         mol_type = other DNA
                         organism = synthetic construct
SEQUENCE: 47
ggtgccagtg ctcgttattg t                                                   21

SEQ ID NO: 48            moltype = DNA   length = 22
FEATURE                  Location/Qualifiers
source                   1..22
                         mol_type = other DNA
                         organism = synthetic construct
SEQUENCE: 48
aagacgtagg catagtagga cc                                                  22

SEQ ID NO: 49            moltype = DNA   length = 20
FEATURE                  Location/Qualifiers
source                   1..20
                         mol_type = other DNA
                         organism = synthetic construct
SEQUENCE: 49
```

```
                                        -continued
actccggggt ctagtacagc                                                   20

SEQ ID NO: 50           moltype = DNA   length = 19
FEATURE                 Location/Qualifiers
source                  1..19
                        mol_type = other DNA
                        organism = synthetic construct
SEQUENCE: 50
ccagcggatc acgttgtct                                                    19

SEQ ID NO: 51           moltype = DNA   length = 20
FEATURE                 Location/Qualifiers
source                  1..20
                        mol_type = other DNA
                        organism = synthetic construct
SEQUENCE: 51
ggcccggatg agtacgatac                                                   20

SEQ ID NO: 52           moltype = DNA   length = 22
FEATURE                 Location/Qualifiers
source                  1..22
                        mol_type = other DNA
                        organism = synthetic construct
SEQUENCE: 52
tccaagaggt tcaccatatc ca                                                22

SEQ ID NO: 53           moltype = DNA   length = 19
FEATURE                 Location/Qualifiers
source                  1..19
                        mol_type = other DNA
                        organism = synthetic construct
SEQUENCE: 53
tgacggcctt catcttcgc                                                    19

SEQ ID NO: 54           moltype = DNA   length = 20
FEATURE                 Location/Qualifiers
source                  1..20
                        mol_type = other DNA
                        organism = synthetic construct
SEQUENCE: 54
ctggaccacg agcctttgat                                                   20

SEQ ID NO: 55           moltype = DNA   length = 20
FEATURE                 Location/Qualifiers
source                  1..20
                        mol_type = other DNA
                        organism = synthetic construct
SEQUENCE: 55
ttgctgcctt caatgtggtg                                                   20

SEQ ID NO: 56           moltype = DNA   length = 21
FEATURE                 Location/Qualifiers
source                  1..21
                        mol_type = other DNA
                        organism = synthetic construct
SEQUENCE: 56
cggagccttg atgtaagatg c                                                 21

SEQ ID NO: 57           moltype = DNA   length = 20
FEATURE                 Location/Qualifiers
source                  1..20
                        mol_type = other DNA
                        organism = synthetic construct
SEQUENCE: 57
cgcacccacg ttttcatacg                                                   20

SEQ ID NO: 58           moltype = DNA   length = 23
FEATURE                 Location/Qualifiers
source                  1..23
                        mol_type = other DNA
                        organism = synthetic construct
SEQUENCE: 58
tctggcatac tcattctggt ttg                                               23

SEQ ID NO: 59           moltype = DNA   length = 21
FEATURE                 Location/Qualifiers
source                  1..21
                        mol_type = other DNA
                        organism = synthetic construct
```

```
SEQUENCE: 59
tgttgttgac ccacatggtt g                                                    21

SEQ ID NO: 60           moltype = DNA   length = 19
FEATURE                 Location/Qualifiers
source                  1..19
                        mol_type = other DNA
                        organism = synthetic construct
SEQUENCE: 60
gaggccctca ctaaggcaa                                                       19

SEQ ID NO: 61           moltype = DNA   length = 21
FEATURE                 Location/Qualifiers
source                  1..21
                        mol_type = other DNA
                        organism = synthetic construct
SEQUENCE: 61
gaggcacgac catcactgtt t                                                    21

SEQ ID NO: 62           moltype = DNA   length = 19
FEATURE                 Location/Qualifiers
source                  1..19
                        mol_type = other DNA
                        organism = synthetic construct
SEQUENCE: 62
acagcggaga tgtaggcca                                                       19

SEQ ID NO: 63           moltype = DNA   length = 21
FEATURE                 Location/Qualifiers
source                  1..21
                        mol_type = other DNA
                        organism = synthetic construct
SEQUENCE: 63
tctggatgaa gggtgtgatc g                                                    21

SEQ ID NO: 64           moltype = DNA   length = 19
FEATURE                 Location/Qualifiers
source                  1..19
                        mol_type = other DNA
                        organism = synthetic construct
SEQUENCE: 64
gctcccctaa gccaaggaa                                                       19

SEQ ID NO: 65           moltype = DNA   length = 19
FEATURE                 Location/Qualifiers
source                  1..19
                        mol_type = other DNA
                        organism = synthetic construct
SEQUENCE: 65
ctggcacagt ttgccttgg                                                       19

SEQ ID NO: 66           moltype = DNA   length = 21
FEATURE                 Location/Qualifiers
source                  1..21
                        mol_type = other DNA
                        organism = synthetic construct
SEQUENCE: 66
cagggaccca ggtcatagga g                                                    21

SEQ ID NO: 67           moltype = DNA   length = 19
FEATURE                 Location/Qualifiers
source                  1..19
                        mol_type = other DNA
                        organism = synthetic construct
SEQUENCE: 67
cacattggca cccgcaatc                                                       19

SEQ ID NO: 68           moltype = DNA   length = 20
FEATURE                 Location/Qualifiers
source                  1..20
                        mol_type = other DNA
                        organism = synthetic construct
SEQUENCE: 68
gaggaacgag aagaggcttg                                                      20
```

METHODS OF USING PROTEIN PALMITOYLATIONS INHIBITORS

This application claims the benefit of U.S. Provisional Application No. 63/262,147, filed on Oct. 6, 2021, which is incorporated herein by reference in its entirety.

STATEMENT REGARDING FEDERALLY SPONSORED RESEARCH

This invention was made with government support under CA180758 and NS090160 awarded by the National Institutes of Health. The government has certain rights in the invention.

SEQUENCE LISTING

A Sequence Listing was filed in electronic format on Oct. 6, 2022. The Sequence Listing was provided as a file entitled 11001-152US1_2022_10_06_Sequence_Listing_version 2.xml, created Oct. 6, 2022, which is 59500 bytes in size. The information in the electronic format of the Sequence Listing is incorporated herein by reference in its entirety.

BACKGROUND

β-Coronaviruses are enveloped, positive-stranded RNA viruses that express a spike protein on the surface giving the virus the appearance of a crown or corona. The SARS-CoV-2 spike glycoprotein (S) is a 1273 amino acids type I membrane protein that binds to the ACE2 receptor on the host cell to initiate infection, viral uptake, and cell-cell fusion. Structurally, the unprocessed S protein precursor consists of an N-terminal signal sequence for endoplasmic reticulum (ER) insertion and a large ectodomain (ER luminal-virion exterior) composed of glycosylation sites, a receptor binding domain (RBD), a trimerization domain, and two proteolytic cleavage sites (S1/S2 and S2') that are required for the conformational changes that present the fusion peptide domain necessary for membrane insertion. On the cytosolic side of the single membrane spanning domain is a short endodomain that contains a cysteine rich domain (CRD) capable of undergoing S-acylation/palmitoylation.

Thus, targeting viral proteins addresses the need for generating therapies and treatments to reduce virus infectivity.

SUMMARY

The present disclosure relates to palmitoyltransferase inhibitors to treat or reduce viral infections and the methods for the manufacture and use thereof.

In one aspect, disclosed herein are methods of treating, inhibiting, reducing, decreasing, and/or ameliorating an enveloped viral infection (such as for example, an infection with a coronavirus (including, but not limited to avian coronavirus (IBV), porcine coronavirus HKU15 (PorCoV HKU15), Porcine epidemic diarrhea virus (PEDV), Human Coronavirus 229E (HCoV-229E), human coronavirus OC43 (HCoV-OC43), human coronavirus HKU1 (HCoV-HKU1), Human coronavirus NL63 (HCoV-NL63), severe acute respiratory syndrome coronavirus (SARS-CoV), Middle East respiratory syndrome-related coronavirus (MERS-CoV), SARS-CoV-2 (including, but not limited to the SARS-CoV-2 B1.351 variant, SARS-CoV-2B.1.1.7 (alpha), SARS-CoV-2B.1.1.7 variant mutant N501Y (alpha), SARS-CoV-2 delta variant, SARS-CoV-2 P.1 variant, SARS25 CoV-2 with T487K, P681R, and L452R mutations in B.1.617.2 (Delta), SARS-CoV-2 with K417N mutation in AY.1/AY.2 (Delta plus), SARS-CoV-2 with D614G, P681H, and D950N mutations in B.1.621 (Mu), SARS-CoV-2 with G75V, T76I, Δ246-252, L452Q, F490S, D614G, and T859N mutations in C.37 (Lambda), SARS-CoV-2 with T478K, Q498R, and H655Y mutations in B.1.1.529 (Omicron)), influenza virus (such as, for example influenza A including, but not limited to H1N1, H1N2, H2N2, H3N1, H3N8, H5N1, H5N2, H5N3, H5N8, H5N9, H7N1, H7N2, H7N3, H7N4, H7N7, H7N9, H9N2, H10N7; or influenza B including, but not limited to Victoria or Yamagata), measles virus, cytomegalovirus (CMV), Epstein-Barr virus, HIV, respiratory syncytial virus (RSV), herpes simplex virus 1 (HSV 1), herpes simplex virus 2 (HSV 2), varicella zoster virus, human herpes virus 8 (HHV-8), and human immunodeficiency virus (HIV)) in a subject said method comprising administering to the subject a therapeutically effective amount of a palmitoyltransferase (PAT) inhibitor (such as, for example an inhibitor having the structure

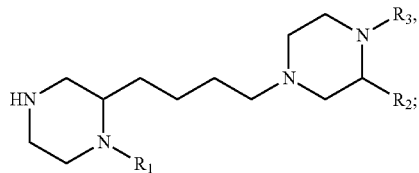

wherein each of R1, R2, and R3 is independently selected from the group consisting of

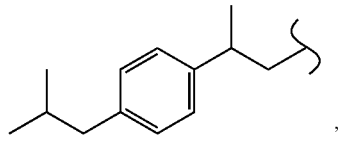
i.

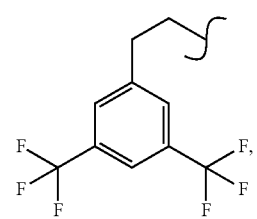
ii.

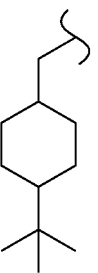
iii.

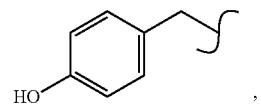
iv.

-continued v.

*[phenyl group]*, vi.

*[naphthyl-methyl group]*, and vii.

*[adamantyl-methyl group]*).

For example, disclosed herein are methods of treating, inhibiting, reducing, decreasing, and/or ameliorating an enveloped viral infection comprising administering to the subject a therapeutically effective amount of a PAT inhibitor wherein the inhibitor comprises Compound 2

*[structure of Compound 2]* or

Compound 3

*[structure of Compound 3]*

Also disclosed herein are methods of treating, inhibiting, reducing, decreasing, and/or ameliorating an enveloped viral infection of any preceding aspect, wherein the PAT inhibitor inhibits DHHC9.

In one aspect, disclosed herein are methods of treating, inhibiting, reducing, decreasing, and/or ameliorating an enveloped viral infection of any preceding aspect, wherein the PAT inhibitor inhibits palmitoylation of one or more cysteine amino acids of a glycoprotein on the viral envelope (such as, for example a coronaviral spike protein (including, but not limited to a SARS-CoV2 spike protein) an influenza virus hemagglutinin protein, and/or HIV gp120). For example, the PAT inhibitor can inhibit palmitoylation at C1235, C1236, C1240, C1241, and/or C1243 of the SARS-CoV2 spike protein.

Also disclosed herein are methods of treating, inhibiting, reducing, decreasing, and/or ameliorating an enveloped viral infection of any preceding aspect, wherein the PAT inhibitor inhibits the palmitoylation at a concentration less than 10 μM such as, for example, a concentration between 1 μM-3 μM.

Also disclosed herein are methods of inhibiting, reducing, decreasing, and/or preventing an enveloped virus (such as, for example, a coronavirus (including, but not limited to avian coronavirus (IBV), porcine coronavirus HKU15 (PorCoV HKU15), Porcine epidemic diarrhea virus (PEDV), Human Coronavirus 229E (HCoV-229E), human coronavirus OC43 (HCoV-OC43), human coronavirus HKU1 (HCoV-HKU1), Human coronavirus NL63 (HCoV-NL63), severe acute respiratory syndrome coronavirus (SARS-CoV), Middle East respiratory syndrome-related coronavirus (MERS-CoV), SARS-CoV-2 (including, but not limited to the SARS-CoV-2 B1.351 variant, SARS-CoV-2B.1.1.7 (alpha), SARS-CoV-2B.1.1.7 variant mutant N501Y (alpha), SARS-CoV-2 delta variant, SARS-CoV-2 P.1 variant, SARS25 CoV-2 with T487K, P681R, and L452R mutations in B.1.617.2 (Delta), SARS-CoV-2 with K417N mutation in AY.1/AY.2 (Delta plus), SARS-CoV-2 with D614G, P681H, and D950N mutations in B.1.621 (Mu), SARS-CoV-2 with G75V, T76I, Δ246-252, L452Q, F490S, D614G, and T859N mutations in C.37 (Lambda), SARS-CoV-2 with T478K, Q498R, and H655Y mutations in B.1.1.529 (Omicron)), influenza virus (such as, for example influenza A including, but not limited to H1N1, H1N2, H2N2, H3N1, H3N8, H5N1, H5N2, H5N3, H5N8, H5N9, H7N1, H7N2, H7N3, H7N4, H7N7, H7N9, H9N2, H10N7; or influenza B including, but not limited to Victoria or Yamagata), measles virus, cytomegalovirus (CMV), Epstein-Barr virus, HIV, respiratory syncytial virus (RSV), herpes simplex virus 1 (HSV 1), herpes simplex virus 2 (HSV 2), varicella zoster virus, human herpes virus 8 (HHV-8), and human immunodeficiency virus (HIV)) from entering a cell comprising contacting the virus with a palmitoyltransferase (PAT) inhibitor (such as, for example an inhibitor having the structure

*[generic piperazine structure with R1, R2, R3 substituents]* wherein each of R1, R2, and R3 is independently selected from the group consisting of i.

[Structure: 4-isobutyl-α-methylbenzyl group]

ii.

[Structure: 3,5-bis(trifluoromethyl)phenethyl group]

iii.

[Structure: 4-tert-butylcyclohexylmethyl group]

iv.

[Structure: 4-hydroxybenzyl group]

v.

[Structure: benzyl group]

vi.

[Structure: 2-naphthylmethyl group], and vii.

[Structure: 1-adamantylmethyl group]), wherein the PAT inhibitor inhibits a palmitoylation of a glycoprotein on the virus envelope (such as, for example a coronaviral spike protein (including, but not limited to a SARS-CoV2 spike protein) an influenza virus hemagglutinin protein, and/or HIV gp120). For example, disclosed herein are methods of inhibiting, reducing, decreasing, and/or preventing an enveloped viral from entering a cell comprising contacting the virus with a therapeutically effective amount of a PAT inhibitor wherein the inhibitor comprises Compound 2

[Structure of Compound 2]

or

Compound 3

[Structure of Compound 3]

In one aspect, disclosed herein are methods of inhibiting, reducing, decreasing, and/or preventing an enveloped virus from entering a cell of any preceding aspect, wherein the PAT inhibitor can inhibit palmitoylation at C1235, C1236, C1240, C1241, and/or C1243 of the SARS-CoV2 spike protein.

Also disclosed herein are methods of inhibiting, reducing, decreasing, and/or preventing an enveloped virus from entering a cell of any preceding aspect, wherein the PAT inhibitor inhibits the palmitoylation at a concentration less than 10 µM such as, for example, a concentration between 1 µM-3 µM.

In one aspect, disclosed herein are methods of inhibiting, decreasing, reducing, and/or preventing palmitoylation of a glycoprotein on a virus envelope (such as, for example a coronaviral spike protein (including, but not limited to a SARS-CoV2 spike protein) an influenza virus hemagglutinin protein, and/or HIV gp120) using a palmitoyltransferase (PAT) inhibitor ((such as, for example an inhibitor having the structure

[Structure with $R_1$, $R_2$, $R_3$ substituents on piperazine groups]

wherein each of R1, R2, and R3 is independently selected from the group consisting of i.

[structure: 4-isobutyl-α-methylbenzyl group]

ii.

[structure: 3,5-bis(trifluoromethyl)benzyl-CH2- group]

iii.

[structure: 4-tert-butylcyclohexyl-CH2- group]

iv.

[structure: 4-hydroxybenzyl group]

v.

[structure: benzyl group]

vi.

[structure: naphthalen-2-ylmethyl group], and vii.

[structure: adamantyl-CH2- group]).

wherein the spike protein is located on an outer surface of an enveloped virus. For example, disclosed herein are methods of inhibiting, decreasing, reducing, and/or preventing palmitoylation of a glycoprotein on a virus envelope comprising contacting the virus with a therapeutically effective amount of a PAT inhibitor wherein the inhibitor comprises Compound 2

[structure of Compound 2]

or

Compound 3

[structure of Compound 3]

Also disclosed herein are disclosed herein are methods of inhibiting, decreasing, reducing, and/or preventing palmitoylation of a glycoprotein on a virus envelope of any preceding aspect, wherein the PAT inhibitor can inhibit palmitoylation at C1235, C1236, C1240, C1241, and/or C1243 of the SARS-CoV2 spike protein.

In one aspect disclosed herein are disclosed herein are methods of inhibiting, decreasing, reducing, and/or preventing palmitoylation of a glycoprotein on a virus envelope of any preceding aspect, wherein the PAT inhibitor inhibits the palmitoylation at a concentration less than 10 µM such as, for example, a concentration between 1 µM-3 µM.

BRIEF DESCRIPTION OF THE DRAWINGS

The accompanying drawings, which are incorporated in and constitute a part of this specification, illustrate certain examples of the present disclosure and together with the description, serve to explain, without limitation, the principles of the disclosure. Like numbers represent the same elements throughout the figures.

FIG. 1A shows the sequence alignment of the carboxy-terminal tails of the spike protein from the indicated coronaviruses. The transmembrane region residues are depicted in bold and the conserved cysteine residues in the c-terminal cysteine rich domain (CRD) are shaded in gray. The 10 cysteines of the SARS-CoV-2 spike protein (S) CRD were grouped as four clusters— C1 (C1235, 1236), C2 (C1240, C1241, 1243), C3 (C1247, 1248, 1250) and C4 (C1253, 1254). Palmitoylation site prediction algorithm predicted 9 of the 10 underlined cysteine residues as potential site of palmitoylation (http://csspalm.biocuckoo.org/online.php). FIG. 1B shows the plasmids with WT SARS-CoV-2 spike protein (S) or the indicated cysteine mutants (C1-4 and ΔC, where all 10 cysteines are mutated to serine) were transfected into HEK293T cells and 48 h later, palmitoylation of the spike protein was assessed by the Acyl-PEGyl Exchange Gel-Shift (APEGS) Assay using anti-spike protein antibody. Addition of mPEG results in slower migrating species, indicated by an asterisk (top panel). GAPDH serves as a loading and palmitoylation control (bottom panel). FIG. 1C shows the schematic of the luciferase reporter SARS-COV-2 spike pseudotyped lentivirus system used. FIGS. 1D and 1E shows the HEK293T-ACE2 or Caco-2 cells were infected with lentivirus pseudotyped with WT spike or its cysteine cluster mutants for 48 h and pseudovirus infection measured by quantifying the luciferase signal. UI represents uninfected control. Data shown are relative to the WT pseudovirus and are averages of the results of at least three independent experiments ±SD. (*$p<0.05$; $p<0.01$; *$p<0.001$, ****=$p<0.0001$ (One-Way ANOVA)).

FIG. 2A shows the native PAGE showing trimeric spike (Tri S), monomeric spike (S) and the S2 fragment of the WT and different cysteine cluster mutants of the S proteins. Actin is included as loading control. FIG. 2B shows the relative normalized intensities of tri S, S and S2 bands in FIG. 2A. FIG. 2C shows the surface immunofluorescence assay for the S protein was performed by using anti-S protein antibodies on unpermeabilized HEK293T cells 48 h after transfection with WT or cysteine cluster mutant S proteins. BF indicates bright field. FIG. 2D shows the HEK293T cells were transfected with plasmids for SARS-CoV-2 spike pseudotyped lentivirus and 48 h later, supernatant containing pseudotyped lentivirus particles (WT and cysteine mutants) were assayed for pseudovirus egress by ELISA against the lentivirus (HIV) p24 protein. FIG. 2E shows the co-immunoprecipitation assay. Plasmids expressing WT or different cysteine cluster mutant S proteins were transfected into HEK293T-ACE2 cells. 48 h after transfection, ACE2 was immunoprecipitated and the presence of S protein was assayed by immunoblot using antibody specific to the S1 subunit. ACE2 immunoprecipitation was also confirmed. Inputs were quantitated by immunoblot (bottom panels).

FIG. 3A shows the schematic representation of dual fluorescent syncytia formation assay. HEK293T-EGFP cells were transfected with WT-S or its cysteine mutant plasmids. After 24 h, cells were detached and mixed with HEK293T-ACE2 cells labeled with cell tracker red CMPTX dye. After another 24 h, syncytia formation was evaluated by visualizing the fluorescence formed by the fusion of the GFP+Spike cells and 293T-ACE2+Red Cell Tracker cells. FIGS. 3B-3C shows the dual fluorescent syncytia formation assay with WT-S and SΔC and quantification of cell-cell fusion ability by measuring the pixel density of the observed syncytia. FIGS. 3D-3E shows the same as in FIGS. 3B-3C, but, with cysteine cluster mutants of the S protein.

FIG. 4A shows the DHHC5 and DHHC9 acyltransferases were knocked down using siRNA for 72 h in HEK293T cells and their respective mRNA levels evaluated by RT-PCR. FIG. 4B shows the immunoblots assessing the efficiency of the siRNA knocked down of DHHC5 and DHHC9. FIG. 4C shows the APEGS assay to evaluate the role of DHHC5 and DHHC9 on S protein palmitoylation in HEK293T cells. FIG. 4D shows the HEK293T-ACE2 cells were infected with WT spike protein pseudotyped lentivirus isolated from HEK293T cells treated with control siRNA or siRNA against DHHC5 or DHHC9. Results are normalized to control siRNA set at 1.0. FIG. 4E shows the HEK293T-ACE2 cells were knocked down for DHHC5 or DHHC9 and 48 h later, infected with WT spike protein pseudotyped lentivirus derived from untreated HEK293T cells. Further 48 h later, pseudovirus infection was measured by quantifying the luciferase signal. Data shown are relative to the control siRNA. FIG. 4F shows the dual fluorescent syncytia formation assay. HEK293T-EGFP cells were transfected with siRNA targeting DHHC5 or DHHC9 and 48 h later, transfected WT-S plasmids. 24 h later, the cells were detached and mixed with HEK293T-ACE2 cells labeled with cell tracker red CMPTX dye. After another 24 h, syncytia formation was evaluated by visualizing the fluorescence formed by the fusion of the GFP+Spike cells and 293T-ACE2+Red Cell Tracker cells. FIG. 4G shows the quantification of cell-cell fusion ability of the data described in FIG. 4E by measuring the pixel density of the observed syncytia. All data shown are averages of the results of at least three independent experiments (3 fields each) ±SD. *=$p<0.05$; =$p<0.01$; *=$p<0.001$, ****, $p<0.0001$ (unpaired t test).

FIG. 5A shows the immunoprecipitation of FLAG tagged DHHC9 with spike protein. HEK293T cells were transfected with either FLAG-DHHC9, or its catalytic inactive mutant of DHHC9 (FLAG-DHHA9 Mut) and an untagged spike protein and 48 h later, immunoprecipitated with FLAG antibodies. The respective empty vectors were used as controls. HC, heavy chain of IgG. FIG. 5B shows the immunoprecipitation of Myc tagged Golga7 with spike protein. HEK293T cells were transfected with Myc tagged Golga7 and an untagged spike protein and 48 h later, immunoprecipitated with anti-Myc antibodies. FIG. 5C shows the co-localization of spike protein with the cis-Golgi marker, GM130 or the endoplasmic reticulum marker, Calnexin. Vero-E6-ACE2 cells were infected with SARS-CoV2 (MOI 0.01) and 48 h later, immunostained for the indicated proteins. FIG. 5D shows similar experiment as in FIG. 5B showing co-localization between spike protein and endogenous DHHC5 and DHHC9. FIG. 5E shows the HEK293T cells were transfected with either untagged spike protein with FLAG-DHHC9 or Myc-Golga7 and 48 h later, immunostained with anti-FLAG or anti-Myc antibodies together with anti-spike antibodies, to show co-localization of transfected spike with exogenous DHHC9 and Golga7. FIG. 5F shows the proximity ligation assay (PLA) to detect the physical proximity between the spike protein and FLAG-DHHC9. Experiment was performed as in FIG. 5D, and PLA was performed with the indicated antibodies followed by immunofluorescence (IFA) against either GM130 or Calnexin to visualize the sub-cellular localization of the detected PLA spots. FIG. 5G shows the PLA to detect the physical proximity between the spike protein and Myc-Golga7. Experiment in FIG. 5G is the same as in FIG. 5D.

FIG. 6A shows the Caco-2 cells were knocked down for DHHC5 or DHHC9 and 48 h later, infected with icSARS-CoV-2-mNG (SARS-CoV-2 stably encoding mNeonGreen; MOI 0.1). 24, 48 and 72 h post-infection, the cells were fixed, nucleus stained with DAPI and visualized under a fluorescence microscope. FIG. 6B shows the mNeonGreen signal from FIG. 6A was quantitated, normalized to DAPI and plotted to show the effect of the respective acyltransferase knocked down on icSARS-CoV-2-mNG infection. All data shown are averages of the results of at least three independent experiments (3 fields each) ±SD. *=p<0.05; =p<0.01; *=p<0.001, ****, p<0.0001 (unpaired t test).

FIG. 7A shows the chemical structures of compounds 2 and 3. FIGS. 7B-7C shows the XTT cell viability assay to access the toxicity of compounds 2 and 3 on HEK293T and Caco-2 cells respectively. Survival is plotted relative to DMSO, vehicle only control. FIG. 7D shows the APEGS Assay to evaluate the palmitoylation of the WT-S protein after treatment with compounds 2 and 3. HEK293T cells were treated with the maximal non-toxic concentration of each compound (3 µM) or the broad spectrum, non-specific acyltransferase inhibitor 2-BP (10 µM) for 12 h before transfection with the spike plasmid. 48 h later, APEGS assay was performed. DHHC9 independent palmitoylation of GAPDH is included as a control. FIG. 7E shows the 293T-ACE2 cells were pretreated with either compounds 2 (3 µM), 3 (3 µM) or 2-BP (10 µM) for 12 h and then infected with luciferase reporter lentivirus pseudotyped with WT-S protein. Luciferase activity was measured 48 h later. FIG. 7F shows the HEK293T cells were pretreated with either compounds 2 (3 µM), 3 (3 µM) or 2-BP (10 µM) for 12 h and then transfected with plasmids required to produce luciferase reporter lentivirus pseudotyped with WT-S protein. The pseudovirus collected was used to infect 293T-ACE2 cells and luciferase activity was measured after 48 h. FIG. 7G shows the HEK293T cells were pretreated with compounds 2 (3 µM), 3 (3 µM) or 2-BP (10 µM) and then transfected with plasmids required to produce lentivirus pseudotyped with WT-spike protein. 48 h later, the supernatant containing pseudotyped lentivirus particles were assayed for pseudovirus egress by ELISA against the HIV p24 protein. FIG. 7H shows the dual fluorescent syncytia formation assay. HEK293T-EGFP cells were pretreated with the indicated concentrations of compounds 2 and 3 for 12 h and then transfected with WT S plasmid. 24 h later, the cells were detached and mixed with HEK293T-ACE2 cells labeled with cell tracker red CMPTX dye. Syncytia formation was evaluated at 24 h by visualizing the fluorescence formed by the fusion of the GFP+Spike cells and 293T-ACE2+Red Cell Tracker cells. FIG. 7I shows the Quantification of cell-cell fusion ability by measuring the pixel density of the observed syncytia in FIG. 7H. All data shown are averages of the results of at least three independent experiments ±SD. *=p<0.05; =p<0.01; *=p<0.001, ****, p<0.0001 (unpaired t test).

FIG. 8A shows the Caco-2 cells were pretreated with the indicated concentrations of compounds 3 and 25 for 12 h and then infected with icSARS-CoV-2-mNG (MOI 0.1). Post-infection, the cells were continued to be incubated in the presence of the respective compound dilutions. 72 h later, the cells were fixed, nucleus stained with DAPI and visualized under a fluorescence microscope. 10 µM 2-BP was also included in this experiment. FIG. 8B shows the mNeonGreen signal from (J) was quantitated (6 fields from each experiment), normalized to DAPI and plotted to show the effect of the respective concentrations of the DHHC9 PAT inhibitors on icSARS-CoV-2-mNG infection. FIG. 8C shows the Caco-2 cells were pretreated with compounds 2 (3 µM), 3 (3 µM) or 2-BP (10 µM) for 12 h and then infected with SARS-CoV-2 (MOI 0.1). Post-infection, the cells were continued to be incubated in the presence of the respective compound dilutions. 72 h later, the virus containing supernatants were collected and used to infect Vero-E6 ACE2 cells. 24 h after this infection, the Vero-E6 ACE2 cells were collected, RNA extracted, and the SARS-CoV-2 N gene quantified using RT-qPCR. UI represents uninfected cells. All data shown are averages of the results of at least three independent experiments ±SD. *=p<0.05; =p<0.01; *=p<0.001, ****, p<0.0001 (unpaired t test).

FIG. 10A shows the co-localization of FLAG-DHHC9, Myc-Golga7 and spike protein with the cis-Golgi marker, GM130 or the endoplasmic reticulum marker, Calnexin. HEK293T2 cells were transfected with the indicated plasmids and 72 h later, immunostained for the indicated proteins. FIG. 10B shows the control PLA with isotype IgGs showing absence of non-specific PLA signal.

DETAILED DESCRIPTION

Figure 1A:
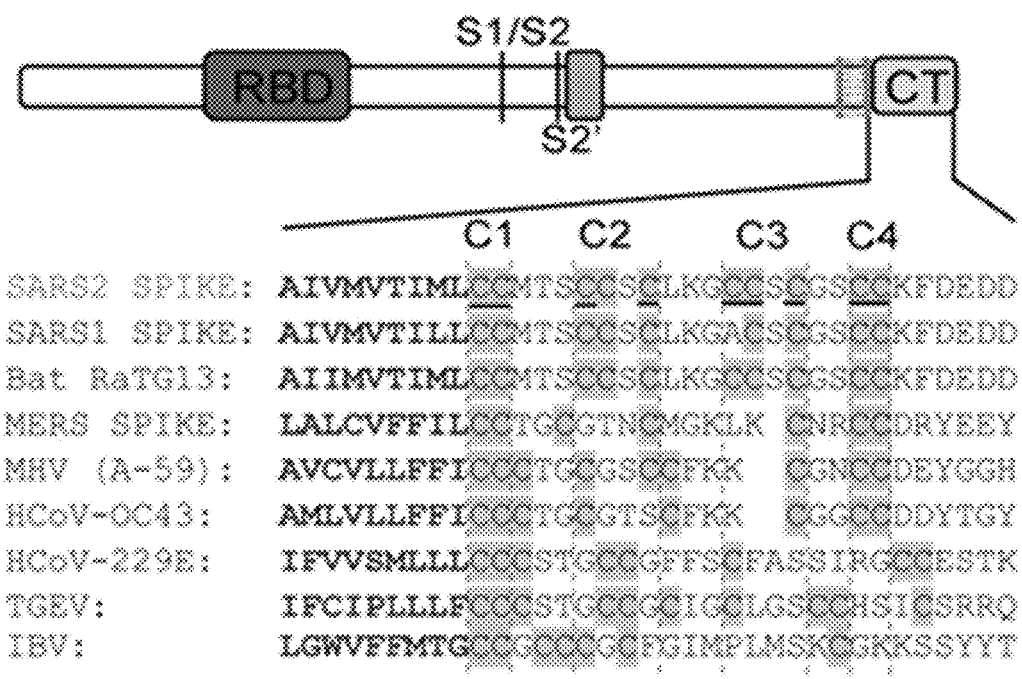
FIGS. 1A, 1B, 1C, 1D, and 1E show palmitoylation of SARS-CoV-2 spike protein and effect of different cysteine clusters mutation of the S protein on pseudotyped lentivirus infection.

The following description of the disclosure is provided as an enabling teaching of the disclosure in its best, currently known embodiment. To this end, those skilled in the relevant art will recognize and appreciate that many changes can be made to the various embodiments herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

Definitions

In this specification and in the claims which follow, reference will be made to a number of terms which shall be defined to have the following meanings:

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, one aspect includes from the one particular value and/or to the other particular value. Similarly, when values are expressed as approximations, by use of the antecedent "about," it will be understood that the particular value forms one aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

The terms "about" and "approximately" are defined as being "close to" as understood by one of ordinary skill in the art. In one non-limiting embodiment the terms are defined to be within 10%. In another non-limiting embodiment, the terms are defined to be within 5%. In still another non-limiting embodiment, the terms are defined to be within 1%.

An "increase" can refer to any change that results in a greater amount of a symptom, disease, composition, condition, or activity. An increase can be any individual, median, or average increase in a condition, symptom, activity, composition in a statistically significant amount. Thus, the increase can be a 1, 2, 3, 4, 5, 6, 7, 8, 9, 10, 15, 20, 25, 30, 35, 40, 45, 50, 55, 60, 65, 70, 75, 80, 85, 90, 95, or 100% increase so long as the increase is statistically significant.

A "decrease" can refer to any change that results in a smaller amount of a symptom, disease, composition, condition, or activity. A substance is also understood to decrease the genetic output of a gene when the genetic output of the gene product with the substance is less relative to the output of the gene product without the substance. Also for example, a decrease can be a change in the symptoms of a disorder such that the symptoms are less than previously observed. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

"Inhibitors" or "antagonist" of expression or of activity are used to refer to inhibitory molecules, respectively, identified using in vitro and in vivo assays for expression or activity of a described target protein, e.g., ligands, antagonists, and their homologs and mimetics. Inhibitors are agents that, e.g., inhibit expression or bind to, partially or totally block stimulation or activity, decrease, prevent, delay activation, inactivate, desensitize, or down regulate the activity of the described target protein, e.g., antagonists. Control samples (untreated with inhibitors) are assigned a relative activity value of 100%. Inhibition of a described target protein is achieved when the activity value relative to the control is about 80%, optionally 50% or 25, 10%, 5%, or 1% or less.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

The term "subject" refers to any individual who is the target of administration or treatment. The subject can be a vertebrate, for example, a mammal. In one aspect, the subject can be human, non-human primate, bovine, equine, porcine, canine, or feline. The subject can also be a guinea pig, rat, hamster, rabbit, mouse, or mole. Thus, the subject can be a human or veterinary patient. The term "patient" refers to a subject under the treatment of a clinician, e.g., physician.

The term "administering" refers to an administration that is oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation or via an implanted reservoir. The term "parenteral" includes subcutaneous, intravenous, intramuscular, intra-articular, intra-synovial, intrasternal, intrathecal, intrahepatic, intralesional, and intracranial injections or infusion techniques.

The term "therapeutically effective" refers to the amount of the composition used is of sufficient quantity to ameliorate one or more causes or symptoms of a disease or disorder. Such amelioration only requires a reduction or alteration, not necessarily elimination.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The terms "treat," "treating," "treatment," and grammatical variations thereof as used herein, include partially or completely delaying, alleviating, mitigating, or reducing the intensity of one or more attendant symptoms of an infection and/or alleviating, mitigating, or impeding one or more causes of a disease, disorder, or condition. Treatments according to the disclosure may be applied preventively, prophylactically, palliatively, or remedially. Treatments are administered to a subject during early onset (e.g., upon initial signs and symptoms of infection), or after an established development of infection. Prophylactic administration can occur for several days after the manifestation of symptoms of an infection.

"Comprising" is intended to mean that the compositions, methods, etc. include the recited elements, but do not exclude others. "Consisting essentially of" when used to define compositions and methods, shall mean including the recited elements, but excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions provided and/or claimed in this disclosure. Embodiments defined by each of these transition terms are within the scope of this disclosure.

As used herein, a "variant" or a "viral variant" refers to a specific virus from a lineage of a group of closely related viruses with a common viral ancestor. The variant generally has acquired a viral genome (or genetic code) that may contain one or more mutations that differ from previous generations.

The terms "cell," "cell line" and "cell culture" include progeny. It is also understood that all progenies may not be precisely identical in DNA content, due to deliberate or inadvertent mutations. All progeny that have the same function or biological property, as screened for in the originally transformed cell, are included. The "cells" used in the present disclosure generally originate from eukaryotic or prokaryotic hosts.

As used herein, an "infection" refers to the invasion of tissues by pathogens, their multiplication, and reaction of host tissues to the infectious agent and any toxins they release. Infections can be caused by a wide range of pathogen, most common are bacteria and viruses.

"Amino acid" is used herein to refer to a chemical compound with the general formula: $NH_2$—CRH COOH, where R, the side chain, is H or an organic group. Where R is organic, R can vary and is either polar or nonpolar (i.e., hydrophobic). The following abbreviations are used throughout the application: A=Ala=Alanine, T=Thr=Threonine, V=Val=Valine, C=Cys=Cysteine, L=Leu=Leucine, Y=Tyr=Tyrosine, N=Asn=Asparagine, P=Pro=Proline, Q=Gln=Glutamine, F=Phe=Phenylalanine, D=Asp=Aspartic Acid, W=Trp=Tryptophan, E=Glu=Glutamic Acid, M=Met=Methionine, K=Lys=Lysine, G=Gly=Glycine, R=Arg=Arginine, S=Ser=Serine, H=His=Histidine. Unless otherwise indicated, the term "amino acid" as used herein also includes amino acid derivatives that nonetheless retain the general formula. An "amino acid consensus sequence" refers to the calculated order of frequent amino acid residues found at each position in a sequence alignment. The consensus sequence can represent multiple sequence alignments in which related sequences within one organism or species, or across various organisms or species are compared to each other and similar sequence patterns are recognized.

A "protein", "polypeptide", or "peptide" each refer to a polymer of amino acids and does not imply a specific length of a polymer of amino acids. Thus, for example, the terms peptide, oligopeptide, protein, antibody, and enzyme are included within the definition of polypeptide. This term also includes polypeptides with post-expression modification, such as palmitoylation (e.g., the addition of a palmitoyl moiety), acetylation, phosphorylation, and the like. A "spike protein" also called an "S protein" refers to the highly glycosylated and large transmembrane protein usually found on the surface of a virus, such as a coronavirus, that allow entry into a host cell and initiates infection.

A "host" refers to any animal (either vertebrate or invertebrate) or plant that harbors a smaller organism; where their relationship can be parasitic, pathogenic, or symbiotic, and where the smaller organism generally uses the animal or plant for shelter, nourishment, and/or reproductive/replicative purposes. The smaller organism can be a microorganism, such as bacteria, viruses, fungi, a parasite, including, but not limited to worms and insects.

Methods of Treating a Viral Infection

The last two decades have seen the emergence of three major coronavirus (CoV) outbreaks. The first was the Severe Acute Respiratory Syndrome-CoV (SARS-CoV) in 2002, then Middle East Respiratory Syndrome-CoV (MERS-CoV) in 2012 and most recently, the SARS-CoV-2 virus causing the COVID-19 pandemic. A coronavirus refers to a large family of single-stranded RNA viruses with a spherical lipid envelope coated with club-shaped spike proteins that usually cause mild to moderate upper-respiratory tract illnesses in birds and mammals, including humans. These viruses are part of a larger group called enveloped viruses. Enveloped viruses are well known in the art and can include, but are not limited, to coronaviruses (including, but not limited to avian coronavirus (IBV), porcine coronavirus HKU15 (PorCoV HKU15), Porcine epidemic diarrhea virus (PEDV), Human Coronavirus 229E (HCoV-229E), human coronavirus OC43 (HCoV-OC43), human coronavirus HKU1 (HCoV-HKU1), Human coronavirus NL63 (HCoV-NL63), severe acute respiratory syndrome coronavirus (SARS-CoV), Middle East respiratory syndrome-related coronavirus (MERS-CoV), SARS-CoV-2 (including, but not limited to the SARS-CoV-2 B1.351 variant, SARS-CoV-2B.1.1.7 (alpha), SARS-CoV-2B.1.1.7 variant mutant N501Y (alpha), SARS-CoV-2 delta variant, SARS-CoV-2 P.1 variant, SARS25 CoV-2 with T487K, P681R, and L452R mutations in B.1.617.2 (Delta), SARS-CoV-2 with K417N mutation in AY.1/AY.2 (Delta plus), SARS-CoV-2 with D614G, P681H, and D950N mutations in B.1.621 (Mu), SARS-CoV-2 with G75V, T76I, Δ246-252, L452Q, F490S, D614G, and T859N mutations in C.37 (Lambda), SARS-CoV-2 with T478K, Q498R, and H655Y mutations in B.1.1.529 (Omicron)), influenza viruses (such as, for example influenza A including, but not limited to H1N1, H1N2, H2N2, H3N1, H3N8, H5N1, H5N2, H5N3, H5N8, H5N9, H7N1, H7N2, H7N3, H7N4, H7N7, H7N9, H9N2, H10N7; or influenza B including, but not limited to Victoria or Yamagata), measles viruses, cytomegalovirus (CMV), Epstein-Barr virus, respiratory syncytial virus (RSV), herpes simplex virus 1 (HSV 1), herpes simplex virus 2 (HSV 2), varicella zoster virus, human herpes virus 8 (HHV-8), and human immunodeficiency virus (HIV)).

Enveloped viruses have developed many strategies to invade cells and evade detection by the host immune system. The entry strategies used by different viruses are determined primarily by the viral structure. Enveloped viruses contain the viral genome and core proteins wrapped within one or more membranes acquired from the cell membranes of a host. After early stages of viral infection, an assembled virus can bud off of an infected host cell, thus becoming an enveloped virus, to further infect other nearby host cells.

Enveloped viruses use membrane fusion to enter or penetrate a cell's membrane and enter the cell. The viral membrane fuses with the cell membrane so that the viral genome is released into the cell cytosol. Protein modifications, such as glycosylation and palmitoylation, regulate membrane interactions and trafficking, and thus are important for viral membrane fusion to host cells.

Protein palmitoylation is the reversible posttranslational addition of palmitate, from palmitoyl-CoA, onto the side chain of cysteine residues via a thioester linkage. Palmitoylation regulates membrane association, trafficking, vesical fission and fusion, and protein stability. Palmitoylation of viral proteins are involved in replication, viral assembly, budding, and cell fusion. Protein palmitoylation is carried out by a family of 23 mammalian DHHC proteins (such as, for example, DHHC9), also called palmitoyltransferases (PAT). An unmet challenge to date is to develop high affinity, specific, PAT inhibitors, to prevent viral membrane associations and trafficking. The most widely used inhibitor, 2-bromopalmitic acid (2-BP) is a non-metabolizable palmitate analog with no detectable preference toward any specific DHHC PAT. Thus, there is a need for PAT inhibitors with high affinity and specificity for targeting enveloped viruses to reduce infectivity.

The present disclosure relates to palmitoyltransferase inhibitors to treat or reduce viral infections and the methods for the manufacture and use thereof.

In one aspect, disclosed herein is are methods of treating, inhibiting, reducing, decreasing, and/or ameliorating an enveloped viral infection in a subject said method comprising administering to the subject a therapeutically effective amount of a palmitoyltransferase (PAT) inhibitor such as those PAT inhibitors disclosed in U.S. Pat. No. 10,085,981 which is incorporated herein by reference in its entirety. Accordingly, disclosed herein are methods of treating, inhibiting, reducing, decreasing, and/or ameliorating an enveloped viral infection (such as for example, an infection with a coronavirus (including, but not limited to avian coronavirus (IBV), porcine coronavirus HKU15 (PorCoV HKU15), Porcine epidemic diarrhea virus (PEDV), Human Coronavirus 229E (HCoV-229E), human coronavirus OC43 (HCoV-OC43), human coronavirus HKU1 (HCoV-HKU1), Human coronavirus NL63 (HCoV-NL63), severe acute respiratory syndrome coronavirus (SARS-CoV), Middle East respiratory syndrome-related coronavirus (MERS-CoV), SARS-CoV-2 (including, but not limited to the SARS-CoV-2 B1.351 variant, SARS-CoV-2B.1.1.7 (alpha), SARS-CoV-2B.1.1.7 variant mutant N501Y (alpha), SARS-CoV-2 delta variant, SARS-CoV-2 P.1 variant, SARS25 CoV-2 with T487K, P681R, and L452R mutations in B.1.617.2 (Delta), SARS-CoV-2 with K417N mutation in AY.1/AY.2 (Delta plus), SARS-CoV-2 with D614G, P681H, and D950N mutations in B.1.621 (Mu), SARS-CoV-2 with G75V, T76I, Δ246-252, L452Q, F490S, D614G, and T859N mutations in C.37 (Lambda), SARS-CoV-2 with T478K, Q498R, and H655Y mutations in B.1.1.529 (Omicron)), influenza virus (such as, for example influenza A including, but not limited to H1N1, H1N2, H2N2, H3N1, H3N8, H5N1, H5N2, H5N3, H5N8, H5N9, H7N1, H7N2, H7N3, H7N4, H7N7, H7N9, H9N2, H10N7; or influenza B including, but not limited to Victoria or Yamagata), measles virus, cytomegalovirus (CMV), Epstein-Barr virus, HIV, respiratory syncytial virus (RSV), herpes simplex virus 1 (HSV 1), herpes simplex virus 2 (HSV 2), varicella zoster virus, human herpes virus 8 (HHV-8), and human immunodeficiency virus (HIV)) in a subject said method comprising administering to the subject a therapeutically effective amount of a palmitoyltransferase (PAT) inhibitor (such as, for example an inhibitor having the structure wherein each of R1, R2, and R3 is independently selected from the group consisting of i.

, ii.

iii.

, iv.

, v.

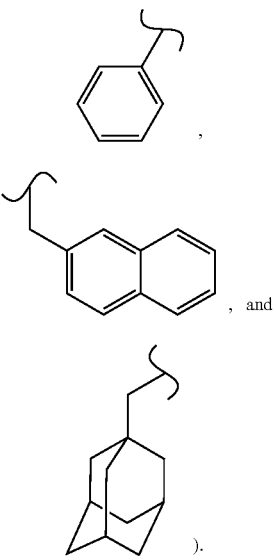

, and vi.

vii.

For example, disclosed herein are methods of treating, inhibiting, reducing, decreasing, and/or ameliorating an enveloped viral infection comprising administering to the subject a therapeutically effective amount of a PAT inhibitor wherein the inhibitor comprises Compound 2

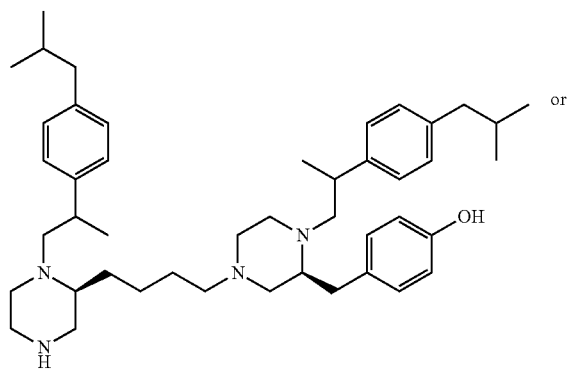

or

Compound 3

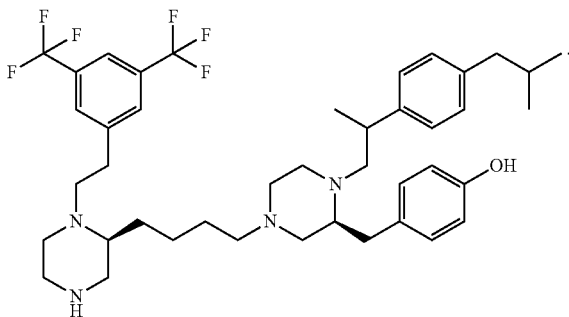

In one aspect, disclosed herein are methods of treating, inhibiting, reducing, decreasing, and/or ameliorating an enveloped viral infection of any preceding aspect, wherein the PAT inhibitor inhibits palmitoylation of one or more cysteine amino acids of a glycoprotein on the viral envelope (such as, for example a coronaviral spike protein (including, but not limited to a SARS-CoV2 spike protein) an influenza virus hemagglutinin protein, and/or HIV gp120). It is understood and herein contemplated that the disclosed PAT inhibitors can inhibit the palmitoylation of 1, 2, 3, 4, 5, 6, 7, 8, 9, 10, 11, 12, 13, 14, or 15 cysteine amino acids of a viral glycoprotein (such as, for example, a coronaviral spike protein (including, but not limited to a SARS-CoV2 spike protein) including, but not limited to the inhibition of palmitoylation at C1235, C1236, C1240, C1241, and/or C1243 of the SARS-CoV2 spike protein.

The disclosed PAT inhibitors can be administered via any route known in the art. For example, the PAT inhibitors can be administered orally, parenterally (e.g., intravenously), by intramuscular injection, by intraperitoneal injection, transdermally, extracorporeally, topically or the like, including topical intranasal administration or administration by inhalant. As used herein, “topical intranasal administration” means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation.

In some aspects, the PAT inhibitor is administered during an active viral infection. In some aspects, the PAT inhibitor is administered during the initial days of infection. In some apects, the PAT inhibitor is administered within the first 30 days of infection. In some as[ects, the PAT inhibitor is administered at day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more after initial infection.

In one aspect, disclosed herein methods of treating, inhibiting, reducing, decreasing, and/or ameliorating an enveloped viral infection of any preceding aspect, wherein the PAT inhibitor inhibits the palmitoylation at a concentration less than 10 μM, such as, for example between 1 μM-3 μM. In particular, the PAT inhibitor can inhibit palmitoylation of the viral glycoprotein at a concentration between 0.25 (250 nM), 0.5 (500 nM), 0.75 (750 nM), 1, 1.5, 2, 2.5, 3, 3.5, 4, 4.5, 5, 5.5, 6, 6.5, 7, 7.5, 8, 8.5, 9, 9.5, or 10 μM.

As noted throughout the disclosed methods can be used to treat active viral infections including coronaviral infections and influenza viral infections. In another aspect, disclosed herein are methods of treating, inhibiting, reducing, decreasing, and/or ameliorating an enveloped viral infection, wherein the enveloped virus is a coronavirus. Examples, of coronaviral infections that can be treated with the disclosed methods can include but not limited to avian coronavirus (IBV), porcine coronavirus HKU15 (PorCoV HKU15), Porcine epidemic diarrhea virus (PEDV), Human Coronavirus 229E (HCoV-229E), human coronavirus OC43 (HCoV-OC43), human coronavirus HKU1 (HCoV-HKU1), Human coronavirus NL63 (HCoV-NL63), severe acute respiratory syndrome coronavirus (SARS-CoV), Middle East respiratory syndrome-related coronavirus (MERS-CoV), SARS-CoV-2 (including, but not limited to the SARS-CoV-2 B1.351 variant, SARS-CoV-2B.1.1.7 (alpha), SARS-CoV-2B.1.1.7 variant mutant N501Y (alpha), SARS-CoV-2 delta variant, SARS-CoV-2 P.1 variant, SARS25 CoV-2 with T487K, P681R, and L452R mutations in B.1.617.2 (Delta), SARS-CoV-2 with K417N mutation in AY.1/AY.2 (Delta plus), SARS-CoV-2 with D614G, P681H, and D950N mutations in B.1.621 (Mu), SARS-CoV-2 with G75V, T76I, Δ246-252, L452Q, F490S, D614G, and T859N mutations in C.37 (Lambda), SARS-CoV-2 with T478K, Q498R, and H655Y mutations in B.1.1.529 (Omicron). Thus, the disclosed methods can be used to treat avian, bovine, porcine and human coronavirus infections.

Similarly, the disclosed methods of treating, inhibiting, reducing, decreasing, and/or ameliorating an enveloped viral infection can be used to wherein the enveloped virus is any variant of the type A, type B, type C, or type D influenza viruses such as, influenza A infections including, but not limited to H1N1, H1N2, H2N2, H3N1, H3N8, H5N1, H5N2, H5N3, H5N8, H5N9, H7N1, H7N2, H7N3, H7N4, H7N7, H7N9, H9N2, H10N7; and/or influenza B infections including, but not limited to Victoria or Yamagata.

In one aspect, disclosed herein is a method of any preceding aspect, wherein the subject is a vertebrate. In one aspect, the subject is a bird (including, but not limited to a chicken, a turkey, a duck, or a quail). In one aspect, disclosed herein is a method of any preceding aspect, wherein the subject is a mammal. In one aspect, the subject is a dog, a cat, a rabbit, a cow, a pig, a sheep, a horse, a mouse, a rat, a monkey, or an ape. In one aspect, disclosed herein is a method of any preceding aspect, wherein the subject is a human.

It is understood and herein contemplated that the disclosed PAT inhibitors prevent the viral glycoprotein from fusing with the host cell membrane and entering the cell to establish an infection. Accordingly, in one aspect, Also disclosed herein are methods of inhibiting, reducing, decreasing, and/or preventing an enveloped virus from entering a cell comprising contacting the virus with any of the palmitoyltransferase (PAT) inhibitors disclosed herein. For example, in one aspect, disclosed herein are methods of inhibiting, reducing, decreasing, and/or preventing an enveloped virus (such as, for example, a coronavirus (including, but not limited to avian coronavirus (IBV), porcine coronavirus HKU15 (PorCoV HKU15), Porcine epidemic diarrhea virus (PEDV), Human Coronavirus 229E (HCoV-229E), human coronavirus OC43 (HCoV-OC43), human coronavirus HKU1 (HCoV-HKU1), Human coronavirus NL63 (HCoV-NL63), severe acute respiratory syndrome coronavirus (SARS-CoV), Middle East respiratory syndrome-related coronavirus (MERS-CoV), SARS-CoV-2 (including, but not limited to the SARS-CoV-2 B1.351 variant, SARS-CoV-2B.1.1.7 (alpha), SARS-CoV-2B.1.1.7 variant mutant N501Y (alpha), SARS-CoV-2 delta variant, SARS-CoV-2 P.1 variant, SARS25 CoV-2 with T487K, P681R, and L452R mutations in B.1.617.2 (Delta), SARS-CoV-2 with K417N mutation in AY.1/AY.2 (Delta plus), SARS-CoV-2 with D614G, P681H, and D950N mutations in B.1.621 (Mu), SARS-CoV-2 with G75V, T76I, Δ246-252, L452Q, F490S, D614G, and T859N mutations in C.37 (Lambda), SARS-CoV-2 with T478K, Q498R, and H655Y mutations in B.1.1.529 (Omicron)), influenza virus (such as, for example influenza A including, but not limited to H1N1, H1N2, H2N2, H3N1, H3N8, H5N1, H5N2, H5N3, H5N8, H5N9, H7N1, H7N2, H7N3, H7N4, H7N7, H7N9, H9N2, H10N7; or influenza B including, but not limited to Victoria or Yamagata), measles virus, cytomegalovirus (CMV), Epstein-Barr virus, HIV, respiratory syncytial virus (RSV), herpes simplex virus 1 (HSV 1), herpes simplex virus 2 (HSV 2), varicella zoster virus, human herpes virus 8 (HHV-8), and human immunodeficiency virus (HIV)) from entering a cell comprising contacting the virus with a palmitoyltransferase (PAT) inhibitor (such as, for example an inhibitor having the structure wherein each of R1, R2, and R3 is independently selected from the group consisting of i.

ii.

iii.

iv.

v.

vi.

, and vii.

).

wherein the PAT inhibitor inhibits a palmitoylation of a glycoprotein on the virus envelope (such as, for example a coronaviral spike protein (including, but not limited to a SARS-CoV2 spike protein) an influenza virus hemagglutinin protein, and/or HIV gp120). For example, disclosed herein are methods of inhibiting, reducing, decreasing, and/or preventing an enveloped viral from entering a cell comprising contacting the virus with a therapeutically effective amount of a PAT inhibitor wherein the inhibitor comprises Compound 2 or

Compound 3

It is understood and herein contemplated that the disclosed PAT inhibitors can inhibit the palmitoylation of 1, 2, 3, 4, 5, 6, 7, 8, 9, 10, 11, 12, 13, 14, or 15 cysteine amino acids of a viral glycoprotein (such as, for example, a coronaviral spike protein (including, but not limited to a SARS-CoV2 spike protein) including, but not limited to the inhibition of palmitoylation at C1235, C1236, C1240, C1241, and/or C1243 of the SARS-CoV2 spike protein.

In one aspect, disclosed herein are methods of inhibiting, reducing, decreasing, and/or preventing an enveloped virus from entering a cell of any preceding aspect, wherein the PAT inhibitor inhibits the palmitoylation at a concentration less than 10 μM, such as, for example, inhibiting palmitoylation at a concentration between 1 μM-3 μM. In one aspect, disclosed herein are methods of inhibiting, reducing, decreasing, and/or preventing an enveloped virus from entering a cell of any preceding aspect, wherein the PAT inhibitor inhibits the palmitoylation at a concentration between 0.25 (250 nM), 0.5 (500 nM), 0.75 (750 nM), 1, 1.5, 2, 2.5, 3, 3.5, 4, 4.5, 5, 5.5, 6, 6.5, 7, 7.5, 8, 8.5, 9, 9.5, or 10 μM.

As noted throughout the disclosed methods of inhibiting, reducing, decreasing, and/or preventing an enveloped virus from entering a cell can be used to treat active viral infections including coronaviral infections and influenza viral infections. In one aspect, disclosed herein are methods of inhibiting, reducing, decreasing, and/or preventing an enveloped virus from entering a cell, wherein the enveloped virus is a coronavirus. Examples, of coronaviral infections that can be treated with the disclosed methods can include but not limited to avian coronavirus (IBV), porcine coronavirus HKU15 (PorCoV HKU15), Porcine epidemic diarrhea virus (PEDV), Human Coronavirus 229E (HCoV-229E), human coronavirus OC43 (HCoV-OC43), human coronavirus HKU1 (HCoV-HKU1), Human coronavirus NL63 (HCoV-NL63), severe acute respiratory syndrome coronavirus (SARS-CoV), Middle East respiratory syndrome-related coronavirus (MERS-CoV), SARS-CoV-2 (including, but not limited to the SARS-CoV-2 B1.351 variant, SARS-CoV-2B.1.1.7 (alpha), SARS-CoV-2B.1.1.7 variant mutant N501Y (alpha), SARS-CoV-2 delta variant, SARS-CoV-2 P.1 variant, SARS25 CoV-2 with T487K, P681R, and L452R mutations in B.1.617.2 (Delta), SARS-CoV-2 with K417N mutation in AY.1/AY.2 (Delta plus), SARS-CoV-2 with D614G, P681H, and D950N mutations in B.1.621 (Mu), SARS-CoV-2 with G75V, T76I, Δ246-252, L452Q, F490S, D614G, and T859N mutations in C.37 (Lambda), SARS-CoV-2 with T478K, Q498R, and H655Y mutations in B.1.1.529 (Omicron). Thus, the disclosed methods can be used to treat avian, bovine, porcine and human coronavirus infections.

Similarly, the disclosed methods of inhibiting, reducing, decreasing, and/or preventing an enveloped virus from entering a cell can be used to wherein the enveloped virus is any variant of the type A, type B, type C, or type D influenza viruses such as, influenza A infections including, but not limited to H1N1, H1N2, H2N2, H3N1, H3N8, H5N1, H5N2, H5N3, H5N8, H5N9, H7N1, H7N2, H7N3, H7N4, H7N7, H7N9, H9N2, H10N7; and/or influenza B infections including, but not limited to Victoria or Yamagata.

In one aspect, disclosed herein are methods of inhibiting, reducing, decreasing, and/or preventing an enveloped virus from entering a cell of any preceding aspect, wherein the subject is a vertebrate. In one aspect, the subject is a bird (including, but not limited to a chicken, a turkey, a duck, or a quail). In one aspect, disclosed herein is a method of any preceding aspect, wherein the subject is a mammal. In one aspect, the subject is a dog, a cat, a rabbit, a cow, a pig, a sheep, a horse, a mouse, a rat, a monkey, or an ape. In one aspect, disclosed herein is a method of any preceding aspect, wherein the subject is a human.

In one aspect, disclosed herein are methods of inhibiting, reducing, decreasing, and/or preventing an enveloped virus from entering a cell, wherein the cell is a respiratory cell, a cardiovascular cellI, s a gastrointestinal cell, a neuron, or glial cell.

In one aspect, disclosed herein are methods of inhibiting, decreasing, reducing, and/or preventing palmitoylation of a glycoprotein on a virus envelope, wherein the spike protein is located on an outer surface of an enveloped virus. In particular, disclosed herein are methods of inhibiting, decreasing, reducing, and/or preventing palmitoylation of a glycoprotein on a virus envelope (such as, for example a coronaviral spike protein (including, but not limited to a SARS-CoV2 spike protein) an influenza virus hemagglutinin protein, and/or HIV gp120) using a palmitoyltransferase (PAT) inhibitor ((such as, for example an inhibitor having the structure wherein each of R1, R2, and R3 is independently selected from the group consisting i.

ii.

iii.

iv.

v.

vi.

vii.

wherein the spike protein is located on an outer surface of an enveloped virus. For example, disclosed herein are methods of inhibiting, decreasing, reducing, and/or preventing palmitoylation of a glycoprotein on a virus envelope comprising contacting the virus with a therapeutically effective amount of a PAT inhibitor wherein the inhibitor comprises Compound 2

Compound 3

Also disclosed herein are disclosed herein are methods of inhibiting, decreasing, reducing, and/or preventing palmitoylation of a glycoprotein on a virus envelope of any preceding aspect, wherein the PAT inhibitor can inhibit palmitoylation at C1235, C1236, C1240, C1241, and/or C1243 of the SARS-CoV2 spike protein.

In one aspect disclosed herein are disclosed herein are methods of inhibiting, decreasing, reducing, and/or preventing palmitoylation of a glycoprotein on a virus envelope of any preceding aspect, wherein the PAT inhibitor inhibits the palmitoylation at a concentration less than 10 µM such as, for example, a concentration between 1 µM-3 µM.

It is understood and herein contemplated that the disclosed PAT inhibitors can inhibit the palmitoylation of 1, 2, 3, 4, 5, 6, 7, 8, 9, 10, 11, 12, 13, 14, or 15 cysteine amino acids of a viral glycoprotein (such as, for example, a coronaviral spike protein (including, but not limited to a SARS-CoV2 spike protein) including, but not limited to the inhibition of palmitoylation at C1235, C1236, C1240, C1241, and/or C1243 of the SARS-CoV2 spike protein.

In one aspect, disclosed herein are methods of inhibiting, decreasing, reducing, and/or preventing palmitoylation of a glycoprotein on a virus envelope of any preceding aspect, wherein the PAT inhibitor inhibits the palmitoylation at a concentration less than 10 µM, such as, for example, inhibiting palmitoylation at a concentration between 1 µM-3 µM. In one aspect, disclosed herein are methods of inhibiting, decreasing, reducing, and/or preventing palmitoylation of a glycoprotein on a virus envelope of any preceding aspect, wherein the PAT inhibitor inhibits the palmitoylation at a concentration between 0.25 (250 nM), 0.5 (500 nM), 0.75 (750 nM), 1, 1.5, 2, 2.5, 3, 3.5, 4, 4.5, 5, 5.5, 6, 6.5, 7, 7.5, 8, 8.5, 9, 9.5, or 10 μM.

As noted throughout the disclosed methods of inhibiting, decreasing, reducing, and/or preventing palmitoylation of a glycoprotein on a virus envelope can be used to with active viral infections including coronaviral infections and influenza viral infections. In one aspect, disclosed herein are methods of inhibiting, decreasing, reducing, and/or preventing palmitoylation of a glycoprotein on a virus envelope of any preceding aspect, wherein the enveloped virus is a coronavirus. Examples, of coronaviral infections that can be treated with the disclosed methods can include but not limited to avian coronavirus (IBV), porcine coronavirus HKU15 (PorCoV HKU15), Porcine epidemic diarrhea virus (PEDV), Human Coronavirus 229E (HCoV-229E), human coronavirus OC43 (HCoV-OC43), human coronavirus HKU1 (HCoV-HKU1), Human coronavirus NL63 (HCoV-NL63), severe acute respiratory syndrome coronavirus (SARS-CoV), Middle East respiratory syndrome-related coronavirus (MERS-CoV), SARS-CoV-2 (including, but not limited to the SARS-CoV-2 B1.351 variant, SARS-CoV-2B.1.1.7 (alpha), SARS-CoV-2B.1.1.7 variant mutant N501Y (alpha), SARS-CoV-2 delta variant, SARS-CoV-2 P.1 variant, SARS25 CoV-2 with T487K, P681R, and L452R mutations in B.1.617.2 (Delta), SARS-CoV-2 with K417N mutation in AY.1/AY.2 (Delta plus), SARS-CoV-2 with D614G, P681H, and D950N mutations in B.1.621 (Mu), SARS-CoV-2 with G75V, T76I, Δ246-252, L452Q, F490S, D614G, and T859N mutations in C.37 (Lambda), SARS-CoV-2 with T478K, Q498R, and H655Y mutations in B.1.1.529 (Omicron). Thus, the disclosed methods can be used to treat avian, bovine, porcine and human coronavirus infections.

Similarly, the disclosed methods of inhibiting, decreasing, reducing, and/or preventing palmitoylation of a glycoprotein on a virus envelope, can be used to wherein the enveloped virus is any variant of the type A, type B, type C, or type D influenza viruses such as, influenza A infections including, but not limited to H1N1, H1N2, H2N2, H3N1, H3N8, H5N1, H5N2, H5N3, H5N8, H5N9, H7N1, H7N2, H7N3, H7N4, H7N7, H7N9, H9N2, H10N7; and/or influenza B infections including, but not limited to Victoria or Yamagata.

Also disclosed herein are methods of inhibiting, decreasing, reducing, and/or preventing palmitoylation of a glycoprotein on a virus envelope of any preceding aspect, wherein the subject is a vertebrate such as a bird (including, but not limited to a chicken, a turkey, a duck, or a quail). In one aspect, disclosed herein is are methods of inhibiting, decreasing, reducing, and/or preventing palmitoylation of a glycoprotein on a virus envelope of any preceding aspect, wherein the subject is a mammal. In one aspect, the subject is a dog, a cat, a rabbit, a cow, a pig, a sheep, a horse, a mouse, a rat, a monkey, or an ape. In some aspects, the subject is a human.

EXAMPLES

To further illustrate the principles of the present disclosure, the following examples are put forth so as to provide those of ordinary skill in the art with a complete disclosure and description of how the compositions, articles, and methods claimed herein are made and evaluated. They are intended to be purely exemplary of the disclosure and are not intended to limit the scope of what the inventors regard as their disclosure. Efforts have been made to ensure accuracy with respect to numbers (e.g., amounts, temperatures, etc.); however, some errors and deviations should be accounted for. Unless indicated otherwise, temperature is ° C. or is at ambient temperature, and pressure is at or near atmospheric. There are numerous variations and combinations of process conditions that can be used to optimize product quality and performance. Only reasonable and routine experimentation will be required to optimize such process conditions.

Example 1: Inhibition of SARS-CoV-2 Spike Protein Palmitoylation Reduces Virus Infectivity Here, the role of palmitoylation of the SARS-CoV-2 spike protein it presented using a pseudotyped luciferase lentivirus system as well as SARS-CoV-2 virus. The role of spike palmitoylation was evaluated on trimerization, S1/S2 furin cleavage, transport through the secretory pathway, release on mature virion particles, binding to the ACE2 receptor, cell-cell syncytia formation and infection. DHHC9 was identified as a PAT palmitoylating SARS-CoV-2 S protein and demonstrated co-localization and physical interaction with the S protein in transfected cells and in SARS-CoV-2 infected cells. Finally, SARS-CoV-2-mNG (SARS-CoV-2 stably encoding mNeonGreen) was included and showed that PAT inhibitors also reduce SARS-CoV-2 infection and syncytia formation. Together, these results establish DHHC9 as a target against SARS-CoV-2 and identified lead compounds for the intervention of the SARS-CoV-2 lifecycle and infectivity.

Results

SARS-CoV-2 spike protein is palmitoylated on multiple sites.

Figure 1B:
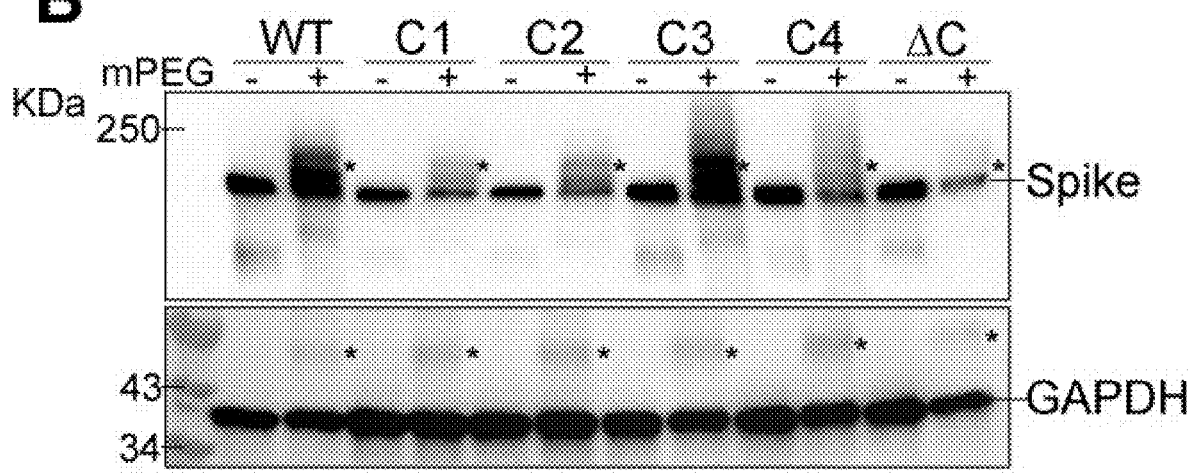

Cysteines in close proximity to transmembrane helices have higher propensity to be palmitoylated. The C-terminal CRD of SARS-CoV-2 spike protein has 10 highly conserved juxtamembrane cysteine residues, 9 of which were predicted to be sites of palmitoylation by the palmitoylation prediction server at http://csspalm.biocuckoo.org/online.php (FIG. 1A). To investigate the role of palmitoylation, these 10 cysteine residues were grouped into 4 clusters —C1 (C1235, 1236), C2 (C1240, C1241, 1243), C3 (C1247, 1248, 1250) and C4 (C1253, 1254), and mutated each cluster to serine (FIG. 1A). A ΔC mutant was also generated in which all 10 cysteines were mutated to serine. The Acyl-PEGyl Exchange Gel-Shift (APEGS) Assay was used to assess the palmitoylation of WT and cysteine mutant S proteins, which employs mPEG-maleimide alkylation to label palmitoylated cysteine residues to study the effect of these mutations on the palmitoylation of the S protein. After PEGylation, the samples were separated by SDS-PAGE and visualized by chemiluminescence using a monoclonal antibody specific for the S2 fragment of the Spike protein. The mPEG minus APEGS reactions served as a control and confirmed the observed gel shifted palmitoylated bands were due to PEGylation at the available cysteine residues. The C1, C2, and C4 cysteine clusters reduced palmitoylation significantly, whereas the ΔC mutation led to undetectable levels of palmitoylation (FIG. 1B). Mutating the C3 cluster appears to be less important for palmitoylation (FIG. 1B). The S protein shifted to several higher molecular weight bands representing different populations of the spike protein with varying degrees of palmitoylation (FIG. 1B). GAPDH, which is also known to undergo palmitoylation was used as a positive control for the APEGS reaction and as a loading control to show equal protein loading per well.

Figure 1C:
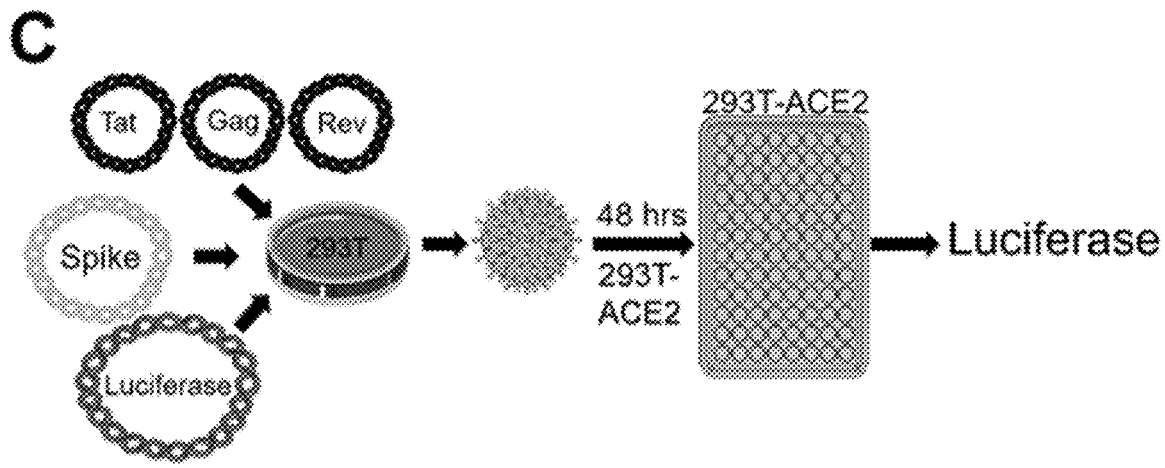
Figure 1D:
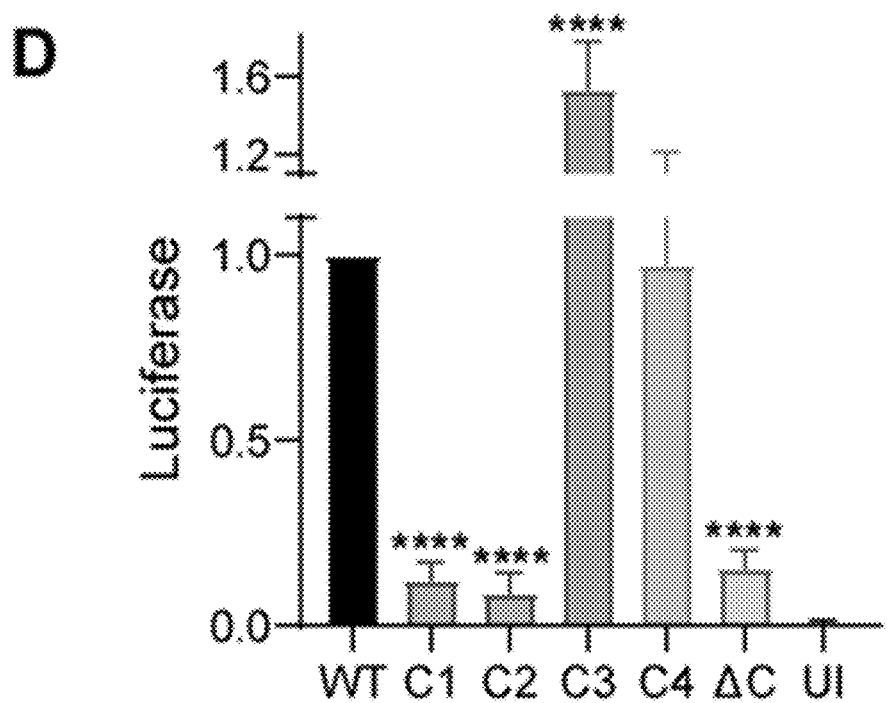
Figure 1E:
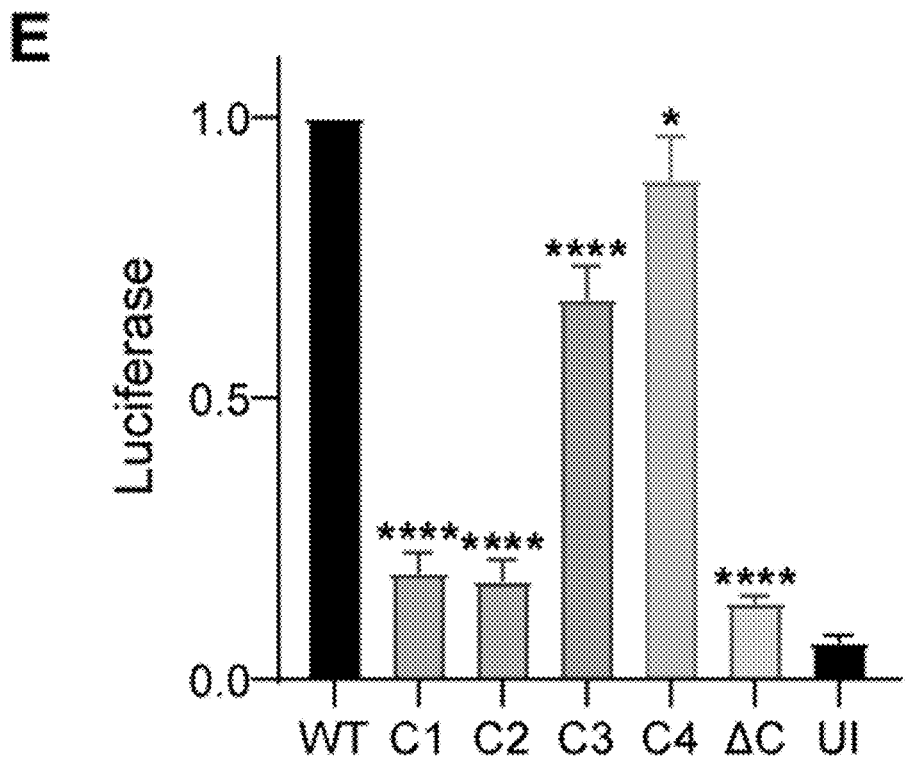
Figure 2A:
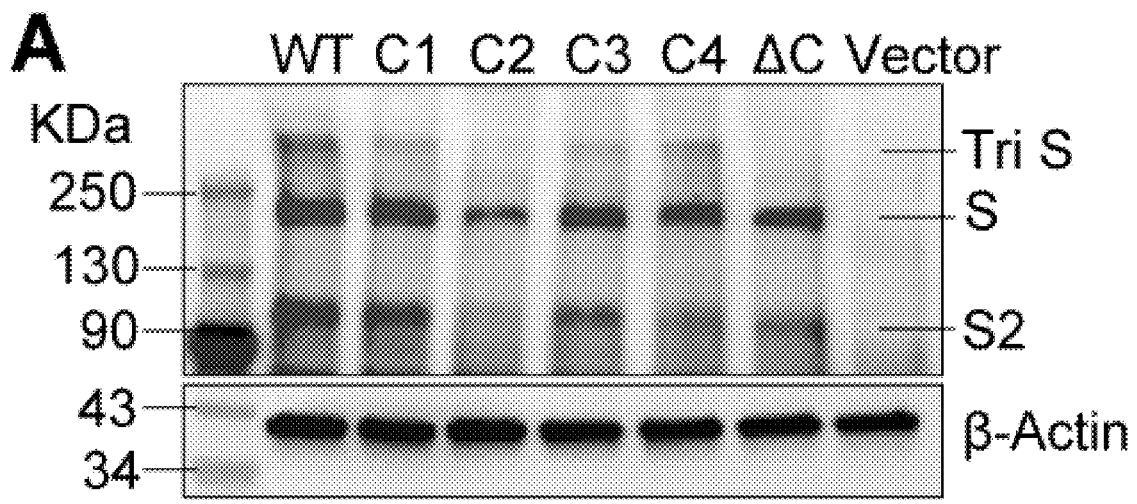
FIGS. 2A, 2B, 2C, 2D, and 2E show the effect of cysteine cluster mutations of SARS-CoV-2 S protein on its trimerization, plasma membrane localization, egress and ACE2 binding.
Figure 2B:
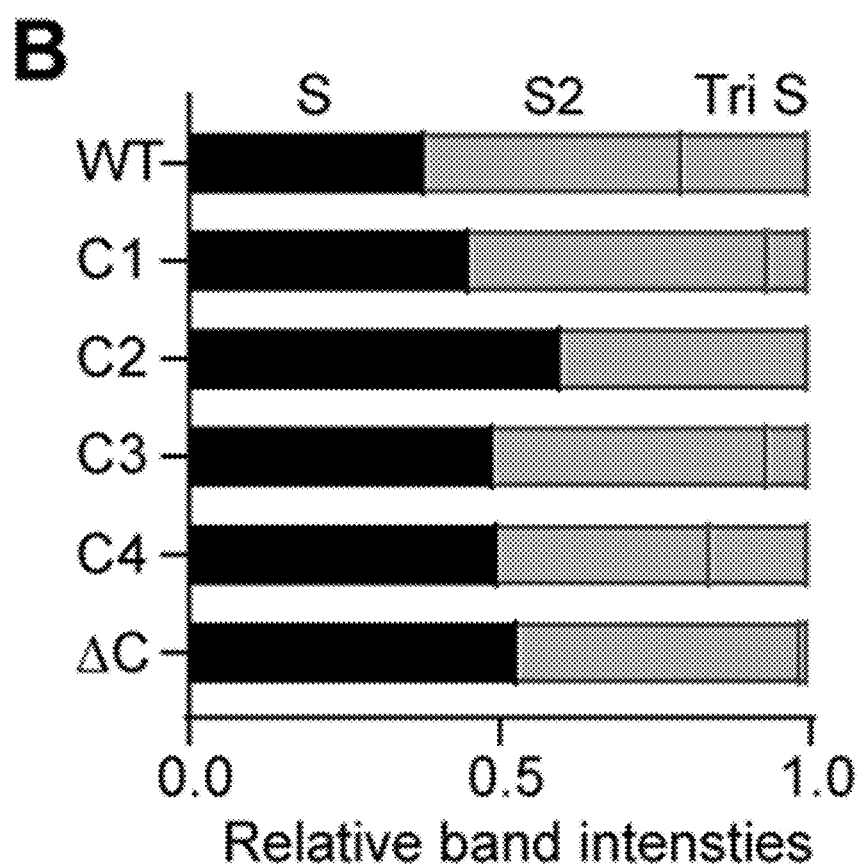
Figure 2C:
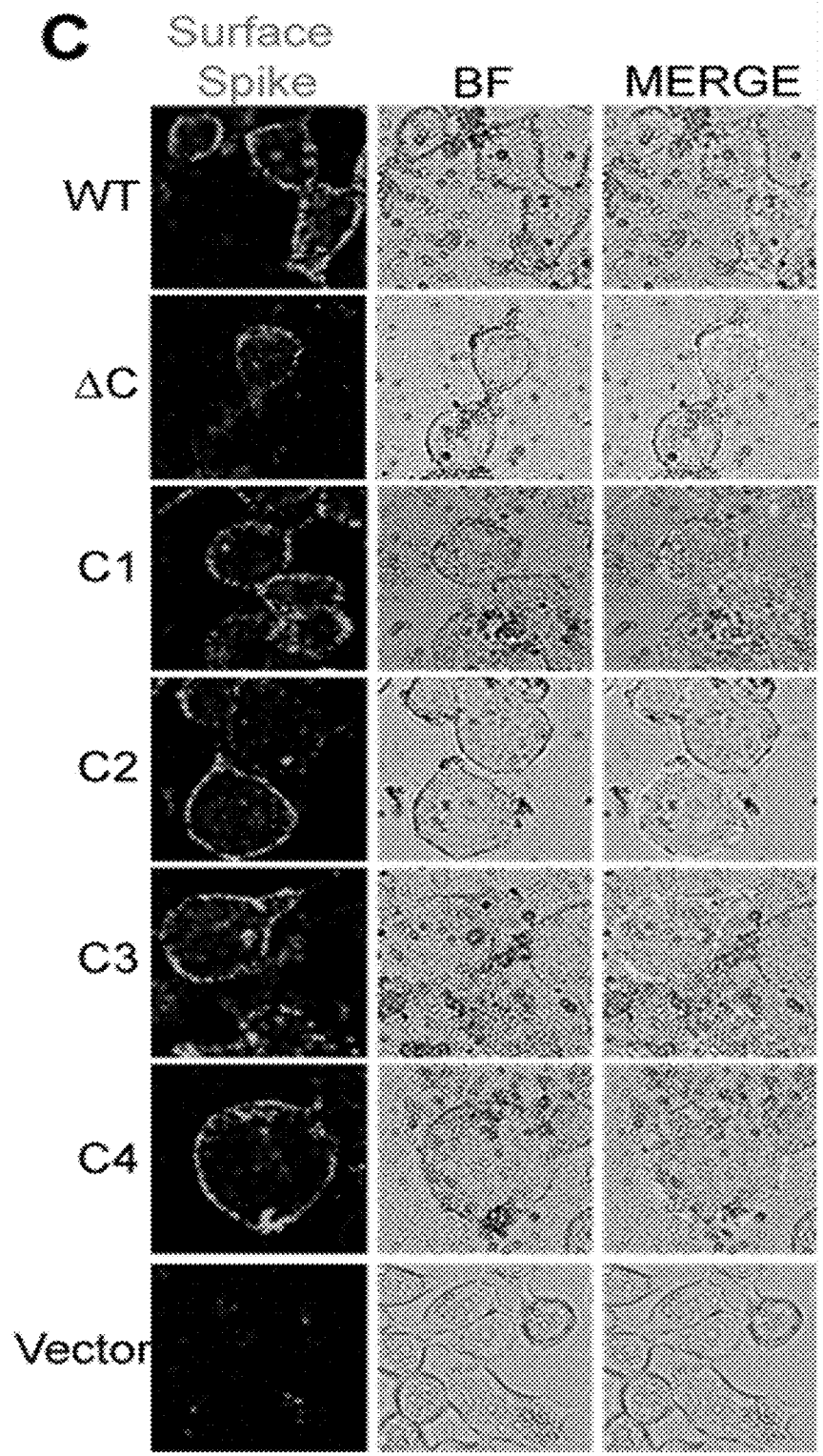
Figure 2D:
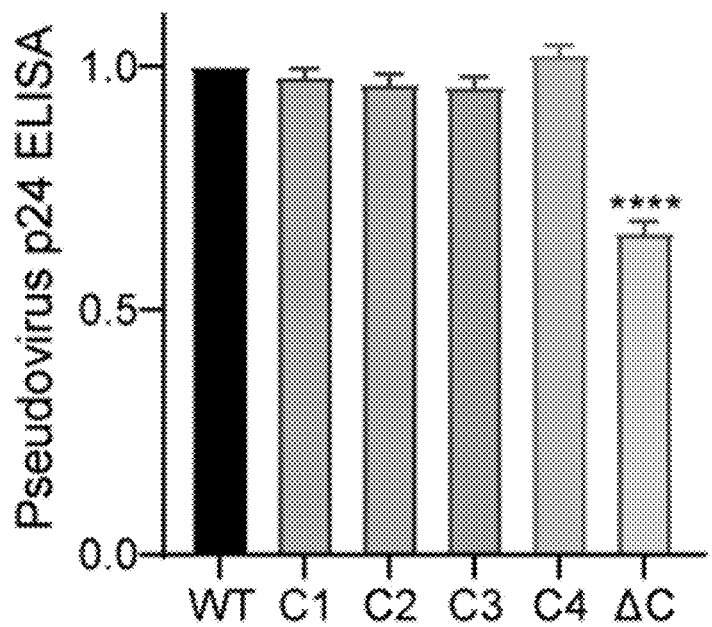
Figure 2E:
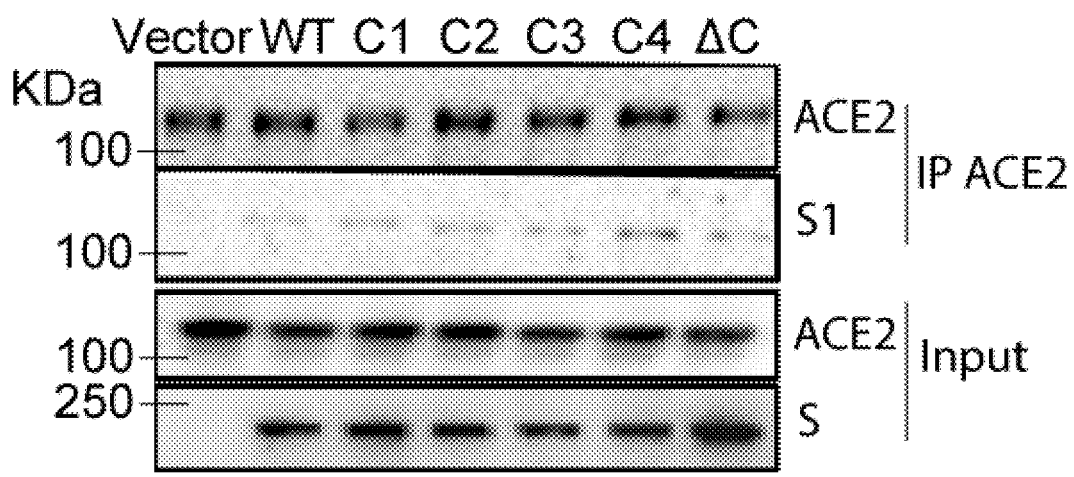
Figure 3A:
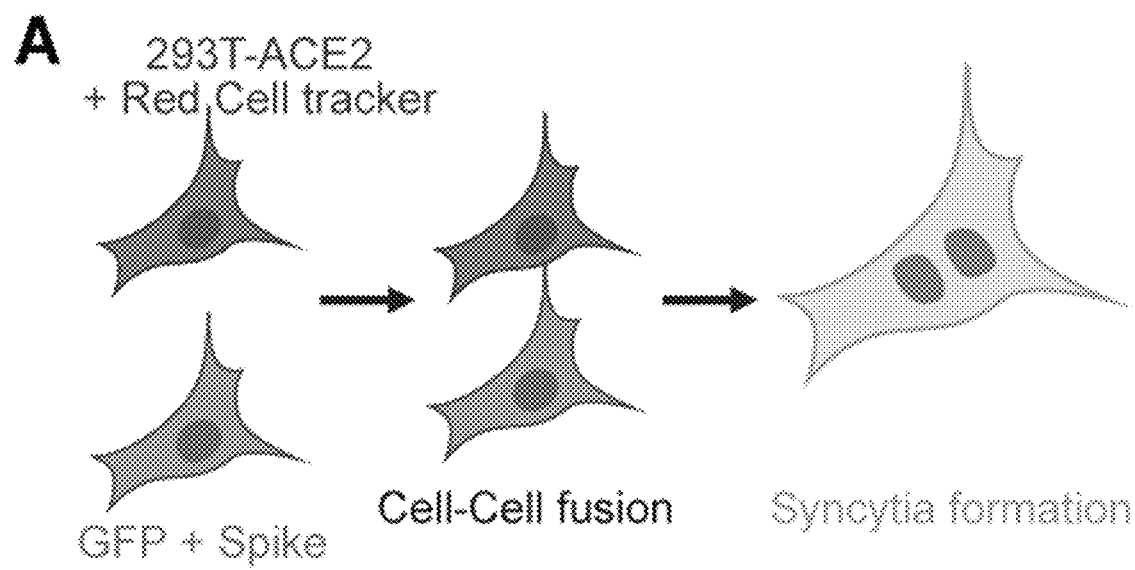
FIGS. 3A, 3B, 3C, 3D, and 3E show that SARS-CoV-2 S protein palmitoylation is required for cell-cell fusion and syncytia formation.
Figure 3B:
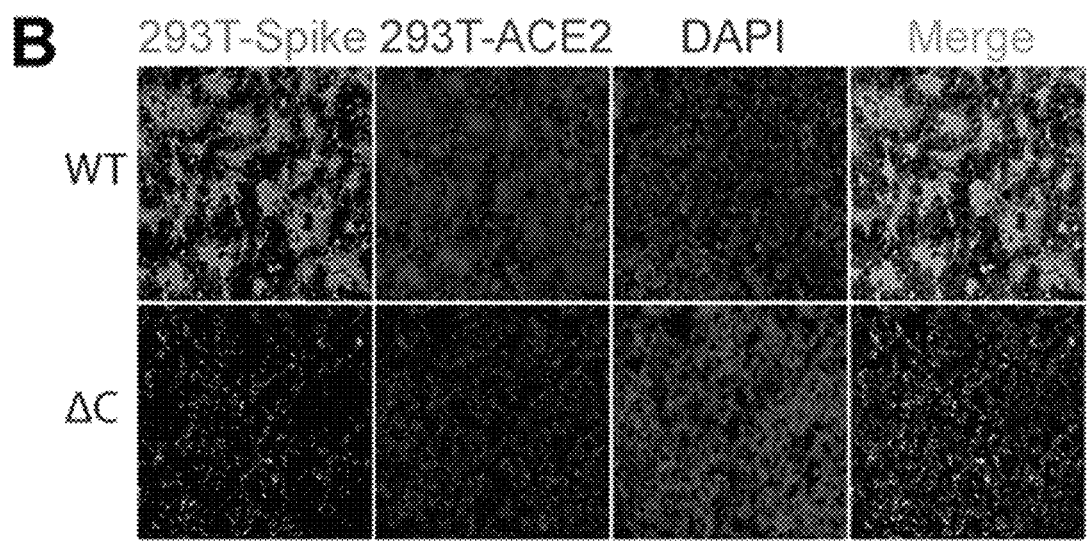
Figure 3C:
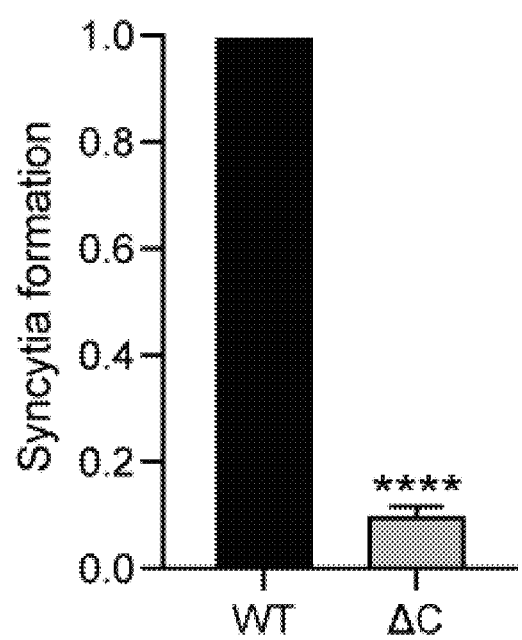
Figure 3D:
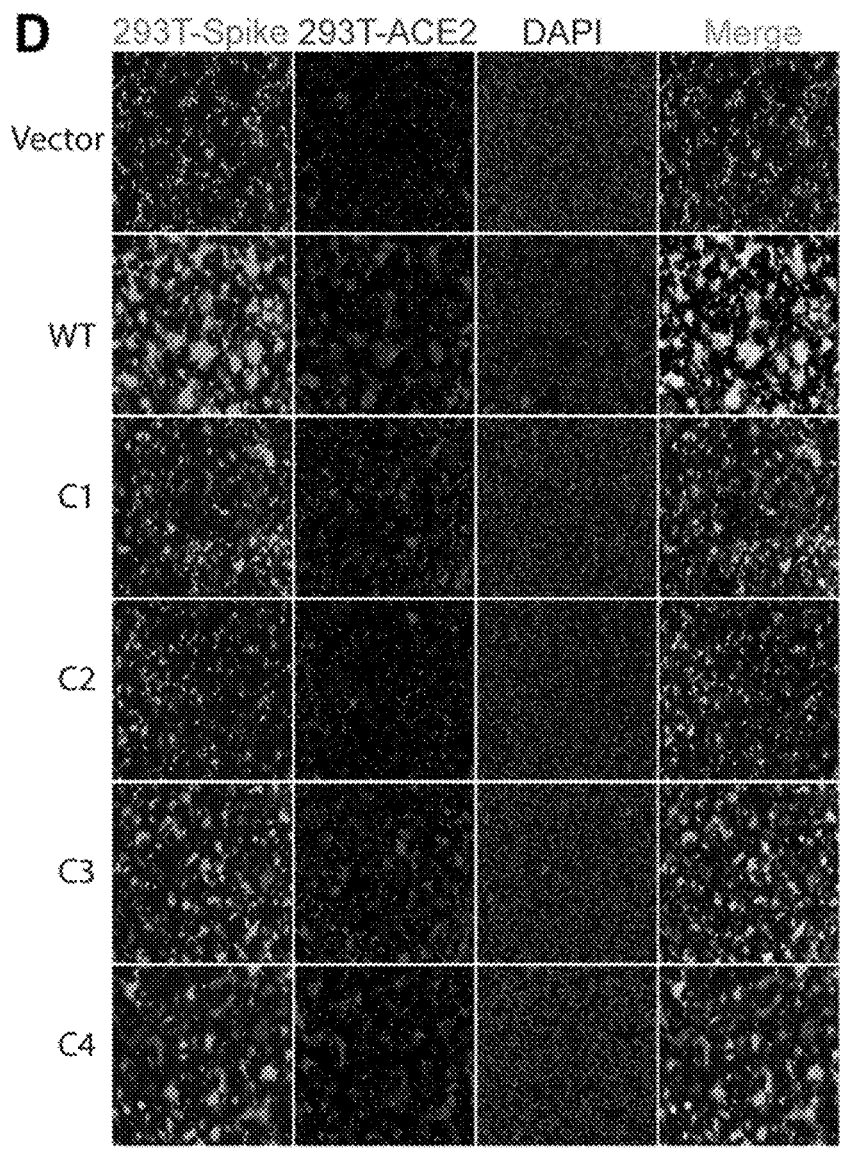
Figure 3E:
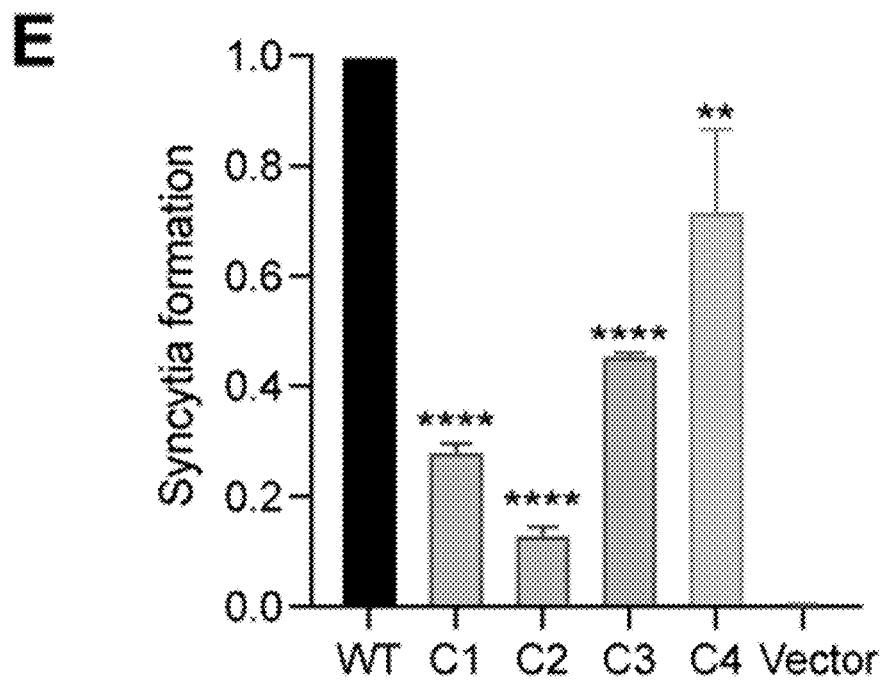

Next, a luciferase reporter SARS-COV-2 spike pseudotyped lentivirus system was employed to study the effect of these cysteine cluster mutations on the cellular entry and infectivity of the S protein by measuring the luciferase activity 48 h after pseudovirus infection of HEK293T-ACE2 or Caco-2 cells (FIG. 1C). Compared to S WT, the ΔC mutant was highly defective in infection of HEK293T-ACE2 cells (FIG. 1D). Clusters C1 and C2 mutations were also defective in infection to levels similar to the ΔC mutant (FIG. 1D). In contrast, clusters C3 and C4 mutations had almost no diminution of pseudovirus entry. Similar results were observed with Caco-2 cells which expresses ACE-2 endogenously (FIG. 1E). Together, these data show that the first five cysteine residues of the SARS-CoV-2 spike protein CRD (C1235, 1236, 1240, 1241 and 1243) are the most functionally important residues to be palmitoylated for infection of ACE-2 expressing cells.

Figure 4A:
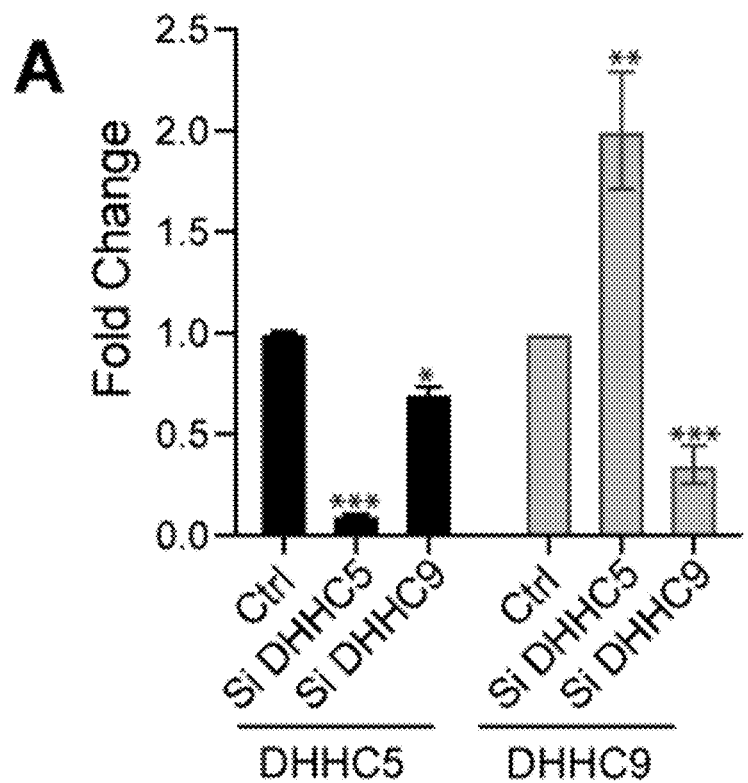
FIGS. 4A, 4B, 4C, 4D, 4E, 4F, and 4G show the evaluation of DHHC5 and DHHC9 acyltransferases as SARS-CoV-2 spike palmitoylating enzymes.
Figure 4B:
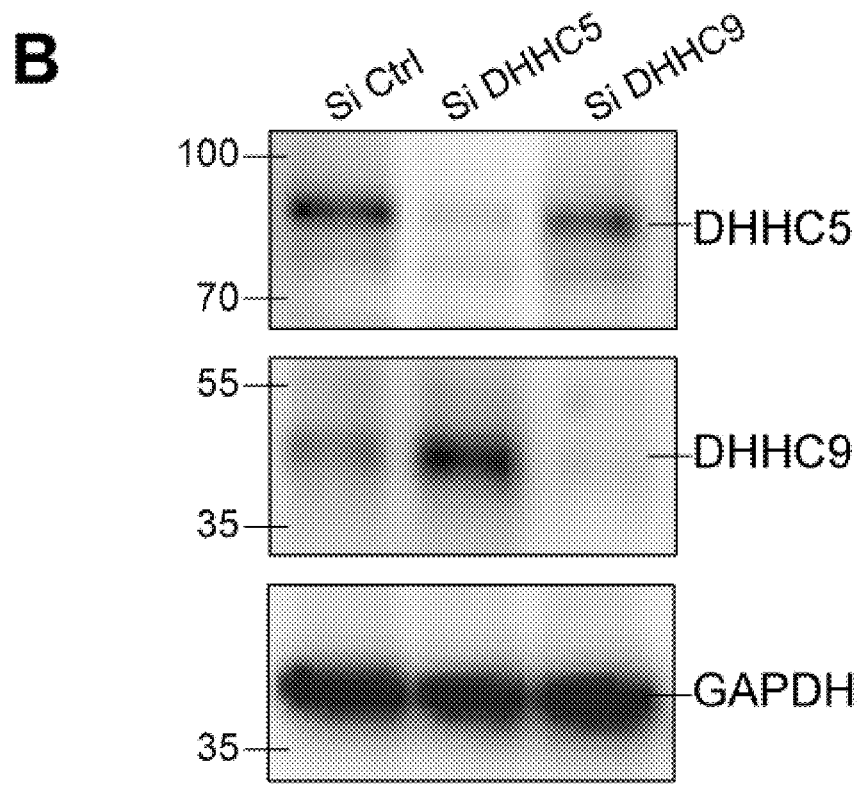
Figure 4C:
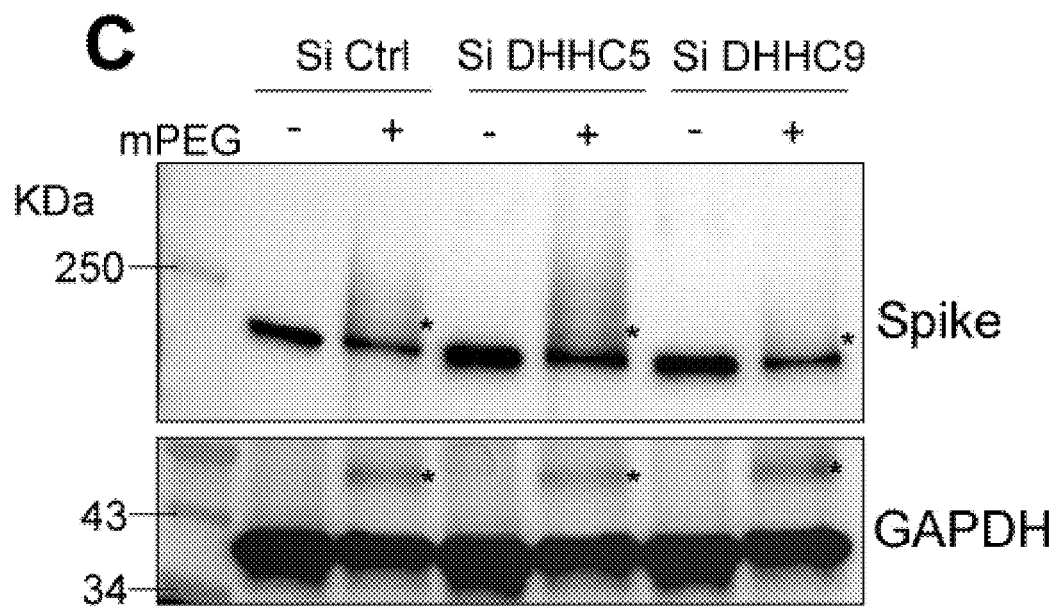
Figure 4D:
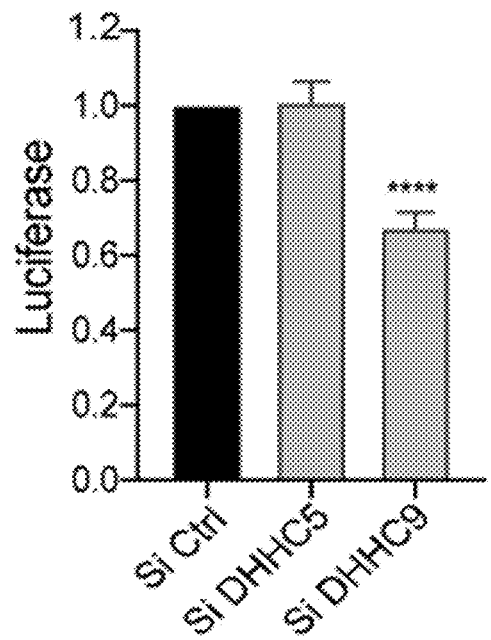
Figure 4E:
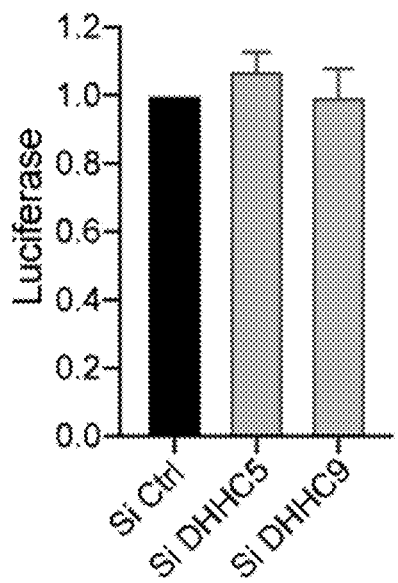
Figure 4F:
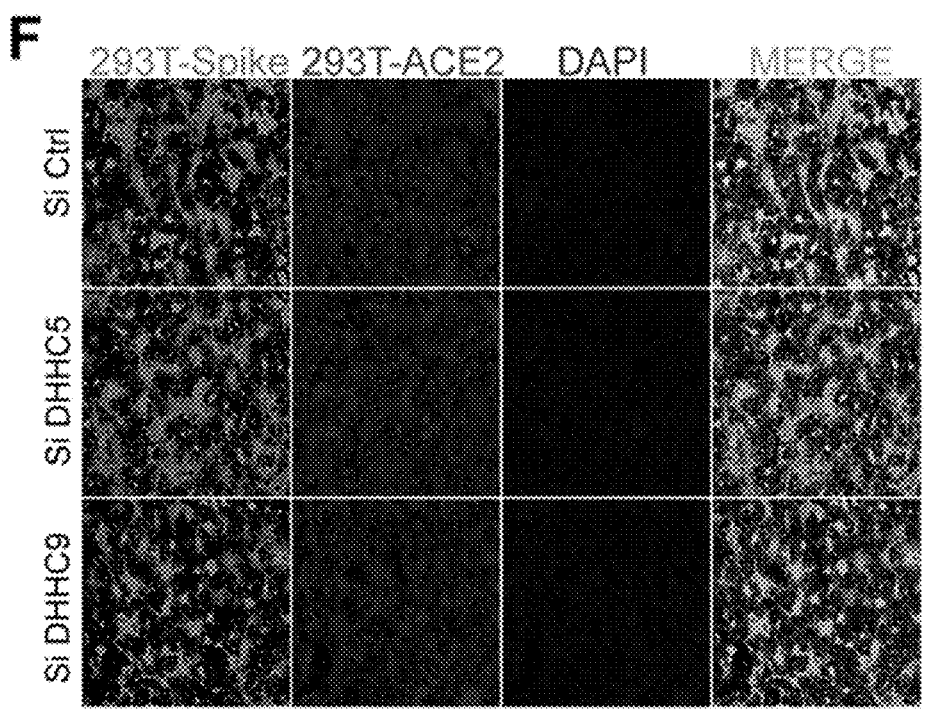
Figure 4G:
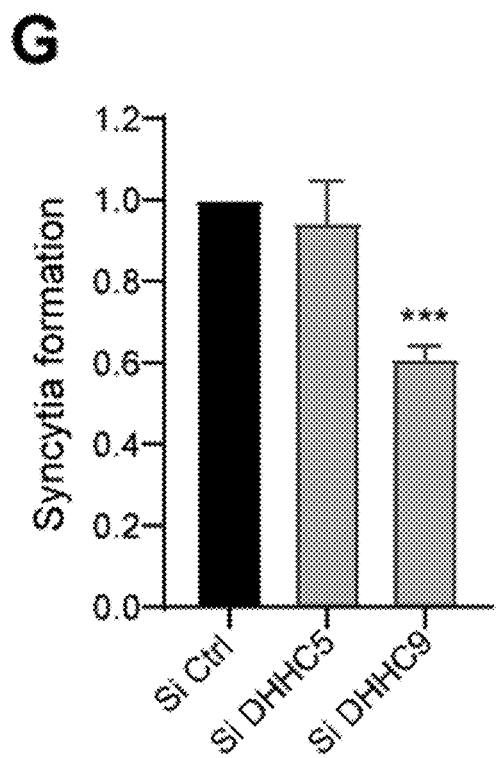

Mutation of Cluster C2 (C1240, C1241, 1243) of S protein abrogates trimerization Next, to investigate if the observed reduction in the infectivity of the C1, C2 and ΔC mutant pseudotyped lentiviruses are due to defects in the intracellular processing of the nascent S protein, trimerization and intracellular furin cleavage were tested at the S1/S2 site by resolving the WT and the mutant S proteins expressed in 293T cells on native-PAGE. Relative band intensities of the three forms of the S protein— S2 fragment, full length, and trimer were normalized to WT being 1.0. As shown in FIGS. 2A and B, compared to the WT protein, mutants C2 and ΔC were severely defective in trimer formation. Spike protein trimerization is known to be essential for its membrane fusion and thus, infection ability. Furin mediated cleavage at the S1/S2 site of the spike protein is a gain-of-function unique to SARS-CoV-2, which is absent in SARS-CoV and other SARS-related coronaviruses. There was no detectable difference in spike furin cleavage between WT and the mutants (FIGS. 2A and B).

Lentivirus based pseudotyped virus assembly and budding occurs at the host plasma membrane. Therefore, the effect of the cysteine cluster mutations on the transport of the S protein to the plasma membrane was investigated. For this, surface immunofluorescence assay (SIF) was performed and then the S protein was immunostained on non-permeabilized cells. Only the ΔC mutant exhibited moderate reduction in its surface expression, while the rest of the cysteine cluster mutations had no measurable effect (FIG. 2C). This showed that the reduced infectivity of the C1 and C2 mutant pseudotyped lentivirus is not due to defects in their ability to be transported to the plasma membrane.

Next, the effect of these mutants on the packaging and egress of the S-pseudotyped lentivirus particles was tested. For this, cell-free S-pseudotyped lentivirus supernatants was collected, and then compared the egress by performing ELISA against the lentivirus capsid protein, p24. The results show that none of the cysteine cluster mutants had any effect on the egress of the pseudotyped lentivirus (FIG. 2D). However, the ΔC mutant showed a moderate, but significant reduction, indicating that only mutating all 10 cysteines has a measurable effect on pseudotyped lentivirus egress.

The effect of spike palmitoylation on ACE2 receptor binding was examined by co-immunoprecipitation. ACE2 was immunoreacted with anti-ACE2 antibody followed by detection of spike by immunoblotting with anti-spike antibody. There appeared to be no difference in ACE2 binding comparing WT to the cysteine cluster mutants (FIG. 2E). Together, these experiments establish that ΔC, and to a lesser extent C1 and C2 exhibit reduced trimerization of the spike protein, whereas furin cleavage, cell surface localization, pseudovirus egress, and ACE2 binding remains unaltered.

Mutating the CRD Diminishes S Protein Mediated Membrane Fusion and Syncytia Formation CoV spike proteins play an indispensable role in the fusion between the viral envelope and the target cell membrane, or between an infected cell and an uninfected cell membrane. Both are essential steps in virus infection and entry, and in cell to cell spread and pathogenesis. Therefore, the effect of the cysteine cluster mutations on the fusogenic potential of the SARS-CoV-2 S protein was investigated. For this, HEK293T-EGFP (HEK293T cells stably transfected with EGFP) were transfected with S WT or its mutant plasmids. 293T-ACE2 cells were stained with a red cell tracker dye and 6 h later, the two cells were mixed at 1:1 ratio, and co-cultured together. When the GFP+S expressing cells and the ACE2 expressing red cells fuse and form a syncytium, it will appear as yellow under a fluorescent microscope (FIG. 3A). First, S WT was compared to the ΔC mutant and observed that the palmitoylation deficient spike protein exhibited a marked reduction in syncytia formation (FIGS. 3B and C). Subsequently, all the cysteine cluster mutants were tested and, consistent with our pseudovirus infection observations (FIGS. 1D and E), C1 and C2 cluster mutations have the greatest effect on syncytia formation (FIGS. 3D and E). C3 and C4 clusters had lower, but significant effects on syncytia formation. These results collectively show that the first 5 cysteines of the SARS-CoV-2 S CRD (C1235, 1236, 1240, 1241, 1243) play the most important role in fusogenic activity.

Reducing DHHC9 Levels Decreases SARS-CoV-2 Spike Palmitoylation

Since palmitoylation of the S protein is an indispensable step for CoV infection, the DHHC PAT responsible for palmitoylating the spike CRD was examined. The SARS-CoV-2 spike protein interaction with DHHC5 and Golga7 was found (Gordon, 2020). Golga7 has been previously identified as an accessory protein of DHHC9 and DHHC5. Thus, DHHC5 and DHHC9 were individually knocked down using siRNA in HEK293T cells and 72 h later knock down efficiencies were confirmed using RT-PCR and WB (FIGS. 4A and B). Both enzymes were knocked down efficiently. Interestingly, knock down of DHHC5 led to a 1.8-fold upregulation of DHHC9 (FIG. 4A), whereas knock down of DHHC9 did not affect DHHC5 expression. The change in mRNA levels resulted in commensurate changes in protein levels (FIG. 4B). To examine this further, mRNA levels of a panel of DHHC genes were measured following knock down of DHHC5 and DHHC9. Knock down of DHHC5 resulted in a compensatory upregulation of DHHC9, 15 and 20 (FIG. 9). However, knock down of DHHC9 did not result in any such compensatory upregulation of any other PAT (FIG. 9).

The APEGS assay was used to examine the palmitoylation of the spike protein following knock down or DHHC5 or DHHC9. Reduction of DHHC9 significantly reduced spike palmitoylation (FIG. 4C). In contrast, in DHHC5 knocked down cells S protein palmitoylation increased, presumably due to the increase in DHHC9, but a contribution from DHHC15 and DHHC20 cannot be ruled out since they are similarly upregulated in a DHHC5 knockdown (FIG. 9). Palmitoylation of GAPDH was unaffected upon knockdown of both DHHC5 or DHHC9 (FIG. 4C, lower pane).

To evaluate the effect of DHHC5 and DHHC9 down regulation on the ability of S protein pseudotyped lentivirus to infect ACE2 bearing cells, lentivirus particles were generated from cells in which DHHC5, and 9 levels have been knocked down. Reduction of DHHC9, but not DHHC5, resulted in a significant reduction in infection of HEK293T-ACE2 cells (FIG. 4D). In contrast, knock down DHHC9 or DHHC5 in the HEK293T-ACE2 cells had no effect on the infection by pseudovirus derived from untreated cells (FIG. 4E). Thus, S protein palmitoylation is required for infection of HEK293T-ACE2 recipient cells, but not for any downstream event following infection. Next, it was tested if syncytia formation requires DHHC5 or DHHC9. As seen in FIGS. 4F and G, knock down of DHHC9, but not DHHC5, resulted in significantly reduced syncytial formation.

Figure 5A:
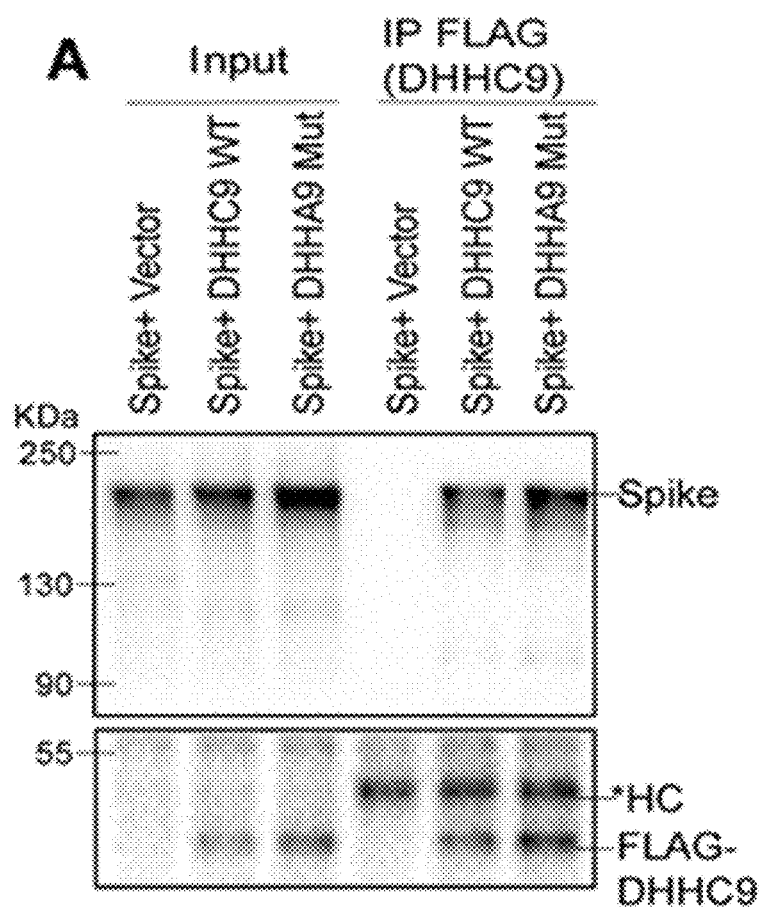
FIGS. 5A, 5B, 5C, 5D, 5E, 5F, and 5G show the interaction of DHHC9 with SARS-CoV-2 spike protein.
Figure 5B:
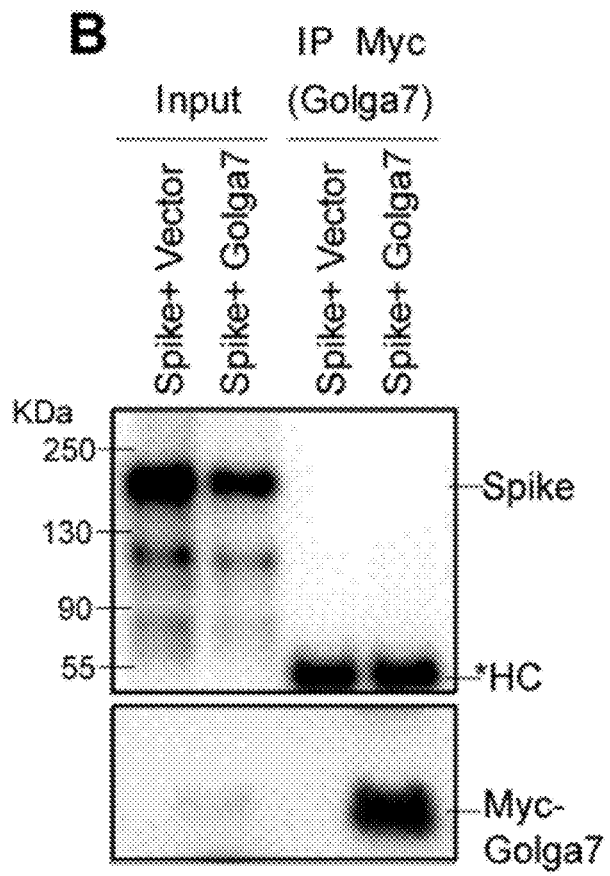

DHHC9 Co-Localizes and Interacts with the SARS-CoV-2 Spike Protein Both in Transfected and Infected Cells To determine whether DHHC9 interacts with the SARS-CoV-2 spike protein, a Co-IP experiment was performed with FLAG tagged DHHC9 or its catalytic mutant, DHHA9 Mut, in HEK293T cells co-transfected with the spike protein. DHHC9 and the spike protein physically interact, and the interaction was not dependent on the palmitoyltransferase activity of DHHC9 (FIG. 5A). In contrast, a similar Co-IP experiment with Myc-tagged Golga7 failed to detect an interaction with the spike protein (FIG. 5B).

Figure 5C:
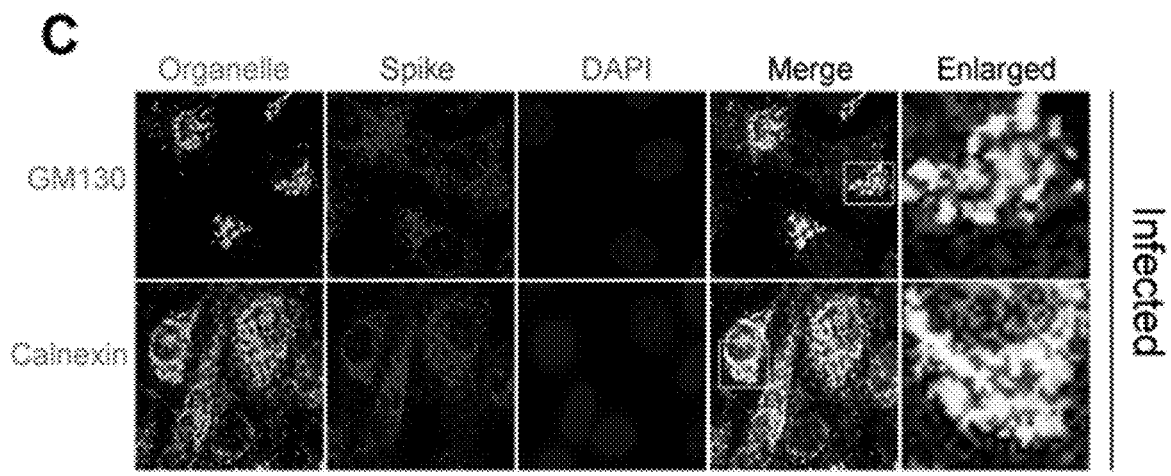
Figure 5D:
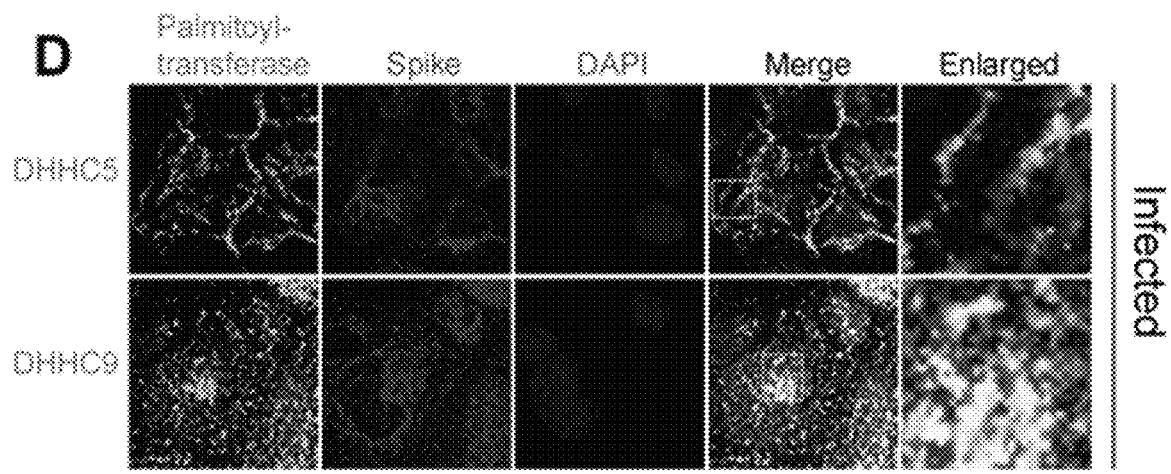
Figure 5E:
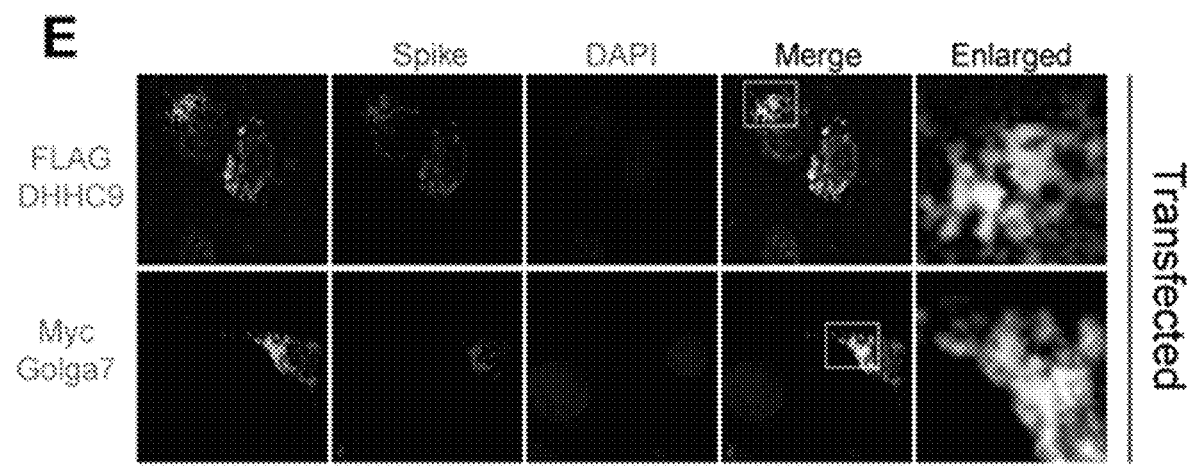
Figure 10:
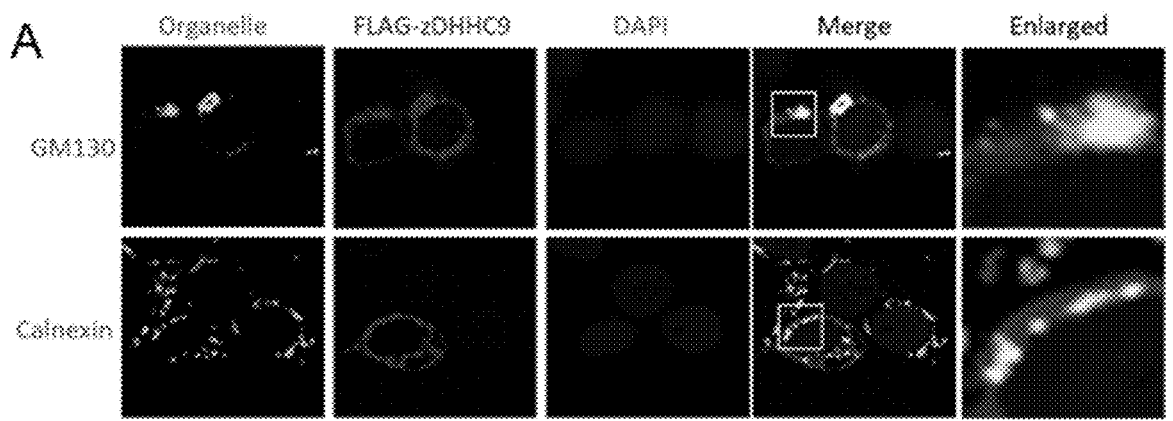
FIGS. 10A and 10B show immunostaining of the viral spike protein.
Figure 10A:
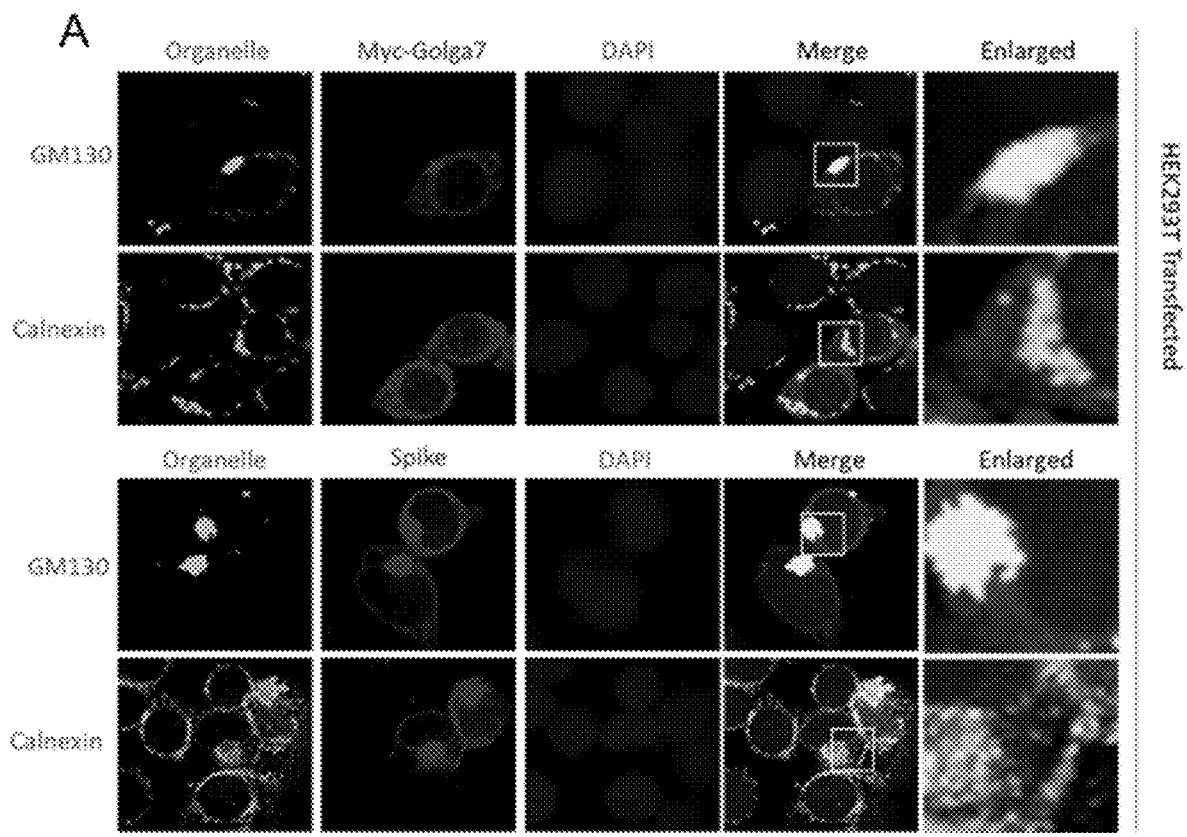

Next, to examine whether the spike protein interacts with DHHC9 in infected cells, immunofluorescence experiments were performed in VERO-E6-ACE2 cells infected with SARS-CoV-2 for 48 h. Co-localization (yellow) with the endoplasmic reticulum marker, Calnexin and the cis-Golgi marker, GM130 indicates that the S protein localizes to both the ER and the Golgi apparatus (FIG. 5C). Similar observations were made in HEK293T cells transfected with FLAG-DHHC9, Myc-Golga7 or the spike protein, where all of these proteins were found to localize to the ER and the Golgi network (FIG. 10A). Following this, co-localization experiments were performed between the spike protein and DHHC5 and 9 in SARS-CoV-2 infected Caco-2 cells (FIG. 5D). In agreement with previous observations, DHHC5 was observed to be localized predominantly on the cell surface, but in addition, some DHHC5 could be observed at other intracellular locations (FIG. 5D). Because the S protein is primarily localized to the ER and the Golgi, a significant co-localization between S and DHHC5 was not observed (FIG. 5D, upper panel). However, under similar conditions, DHHC9 extensively co-localized with spike protein (FIG. 5D, lower panel). To further confirm the spike protein's co-localization with DHHC9 and to exclude the possible non-specific staining due to the DHHC9 antibody, similar co-localization experiments were performed in HEK293T cells transfected with FLAG DHHC9 and Myc-tagged Golga7. Significant co-localization was observed between DHHC9 and the spike protein (FIG. 5E, top panel). Myc Golga7, also co-localized with the spike protein, albeit to a lesser degree (FIG. 5E, bottom panel).

Figure 5F:
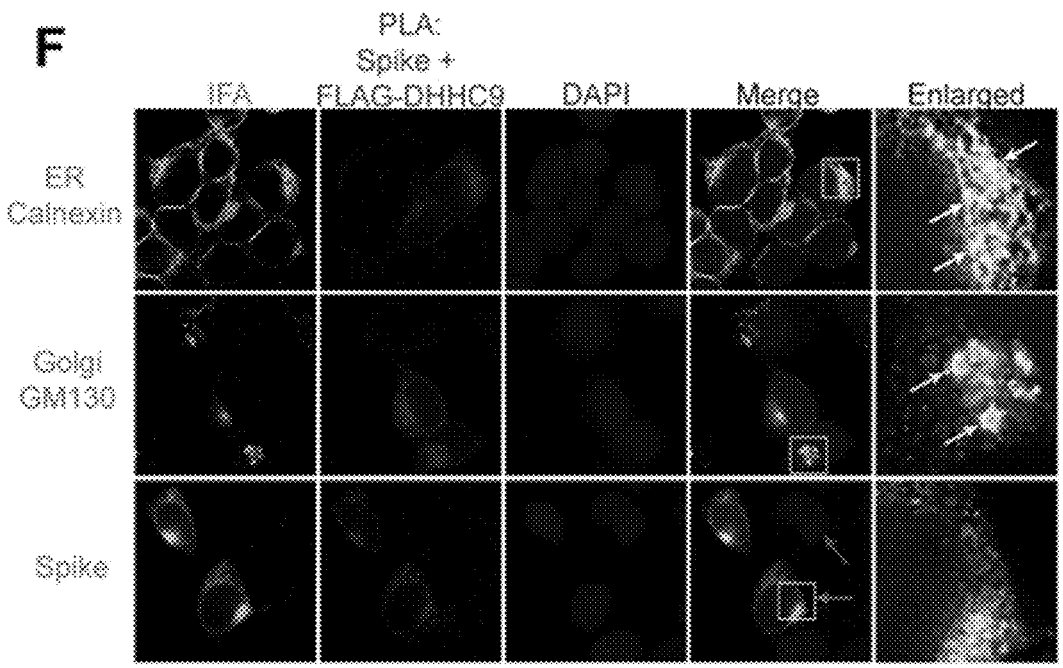
Figure 5G:
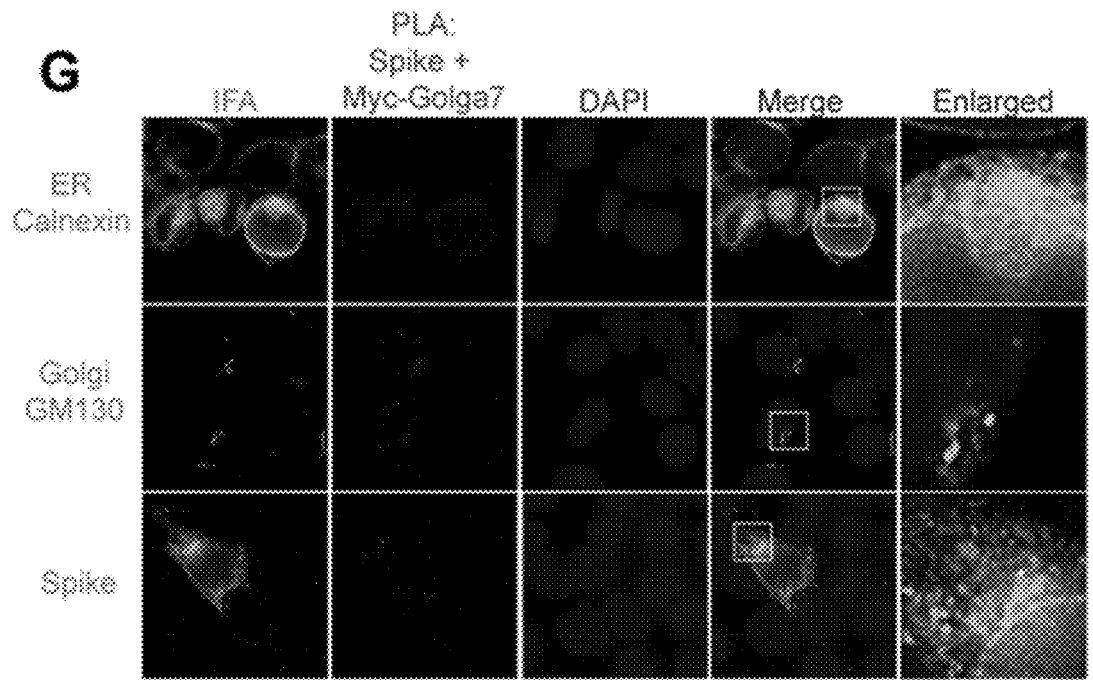
Figure 10B:
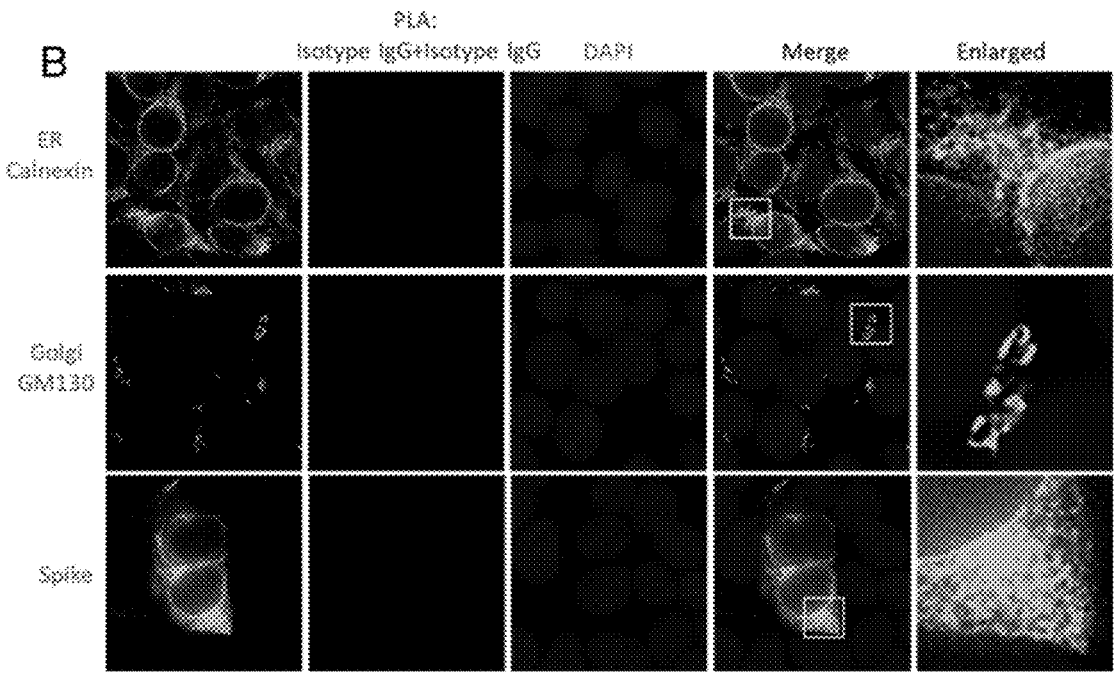

The proximity ligation assay (PLA) provides a better method to assess direct interactions (<40 nm) between proteins in cells. When PLA was performed, robust interactions were observed between the spike protein and FLAG DHHC9 (FIG. 5F). Immunofluorescence against Calnexin and GM130 was also performed in the same experiment and found that the PLA signal between the S protein and DHHC9 localizes partially to the Golgi apparatus, but almost entirely to the ER network (FIG. 5F, arrows). This shows that palmitoylation of spike occurs primarily in the ER and secondarily in the ERGIC, as Calnexin is also found in the ERGIC. In a similar experiment, where PLA was performed between the spike protein and Golga7, a significant PLA signal was not detected, again showing that spike and Golga7 do not directly interact with each other (FIG. 5G). The specificity of the PLA signal was confirmed by isotype IgG controlled PLA reaction which did not produce any signal (FIG. 10B).

Figure 6A:
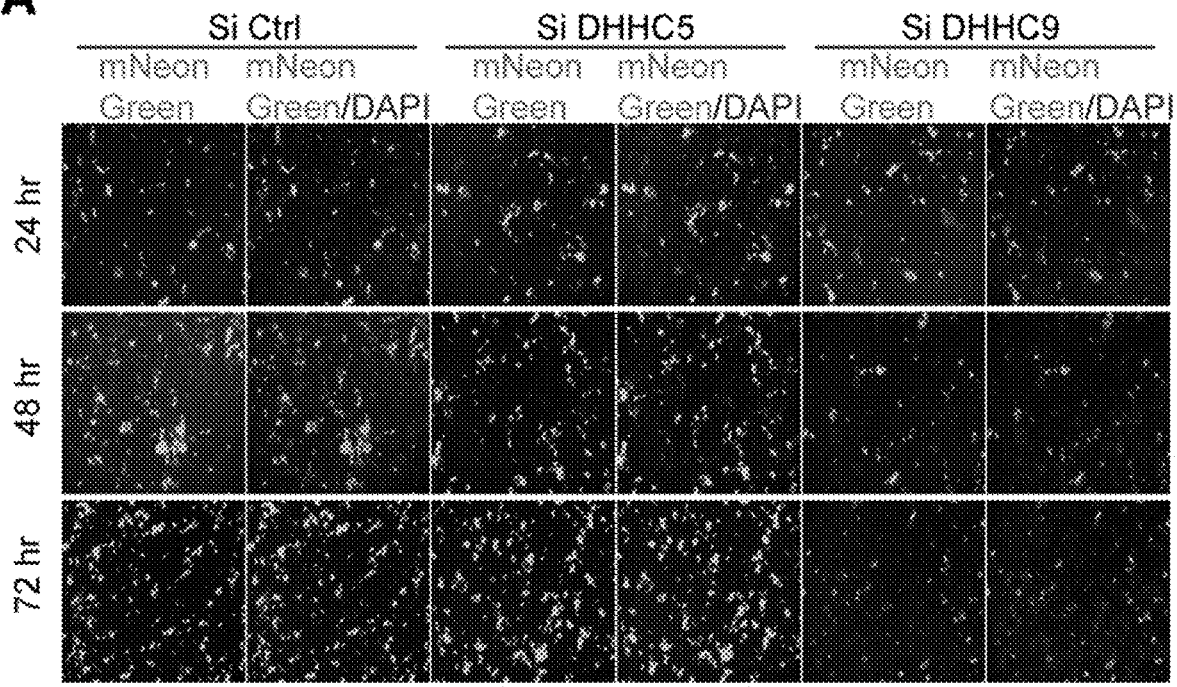
FIGS. 6A and 6B show the effect of DHHC9 knockdown on SARS-CoV-2 infection in Caco-2 cells.
Figure 6B:
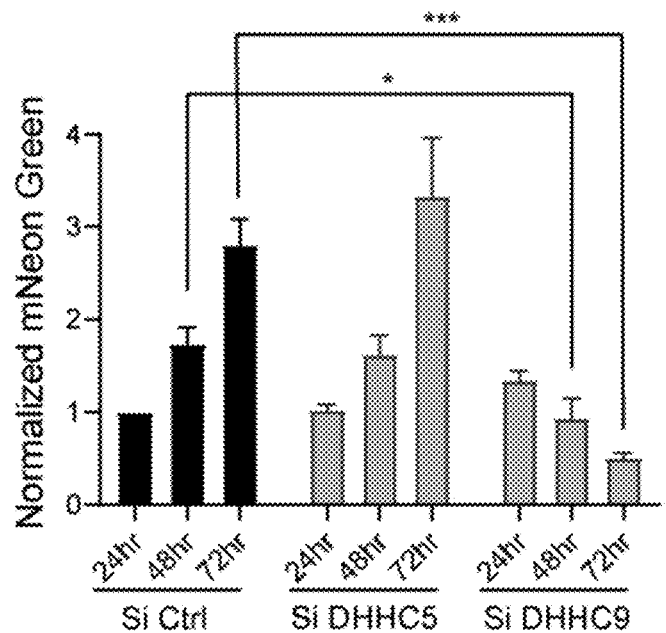
Figure 11:
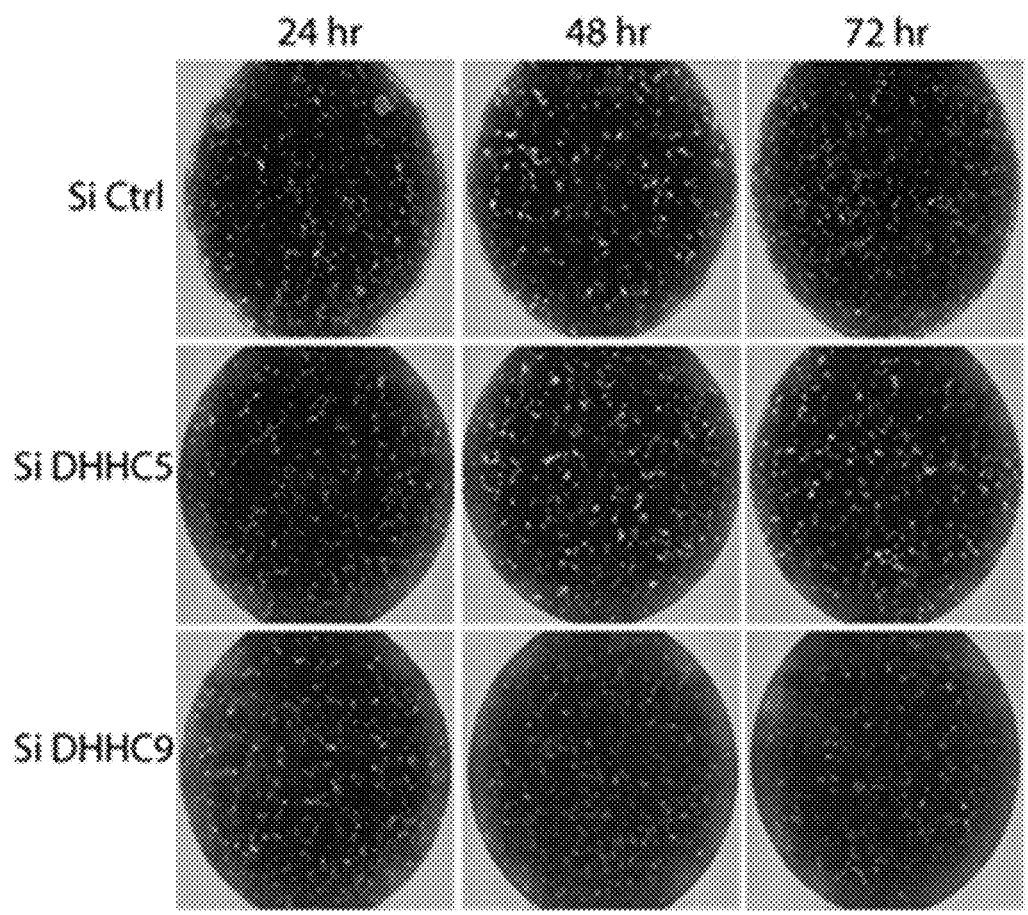
FIG. 11 shows additional images of FIG. 6A. Images of the entire well of the 96 well plate is provided to forego any bias in the region of interest photographed.

SARS-CoV-2 Infection and Syncytia Formation in Caco-2 Cells Requires DHHC9 Dependent Palmitoylation of Spike Protein Having established that DHHC9 plays a major role in the palmitoylation of the SARS-CoV-2 spike protein in-vitro using pseudovirus, attention was directed towards the SARS-CoV-2 virus. SARS-CoV-2-mNG, a fluorescently labeled virus, is based on the 2019-nCoV/USA_WA1/2020 strain isolated from the first reported SARS-CoV-2 case in the US. SARS-CoV-2-mNG is a recombinant virus in which the mNeonGreen gene has been inserted into ORF7 of the viral genome. This recombinant virus exhibits similar plaque morphology, viral RNA profile, and replication kinetics compared to the original clinical isolate. Thus, this virus can be used to determine the efficiency of SARS-CoV-2 infection and syncytia formation. Caco-2 cells transfected with DHHC9 or DHHC5 siRNA were infected with SARS-CoV-2-mNG and 24, 48 and 72 h post-infection, monitored for mNeonGreen expression. At 24 h post-infection, the mNeonGreen signal was not measurably reduced after knockdown of DHHC5 or DHHC9 (FIG. 6A, B and FIG. 11). However, at 48 and 72 h post-infection, the mNeonGreen signal in the DHHC9 knocked down cells reduced significantly. An explanation for this is that as the cells were infected with SARS-CoV-2-mNG harvested from WT VERO-E6 cells, the S protein on these virus particles were efficiently palmitoylated and knock down of the respective PATs in the recipient Caco-2 cells had no effect on the infection process and the expression of mNeonGreen at 24 h post infection. However, with time (48 and 72 h), nascent virion particles increasingly harbored palmitoylation-deficient spike protein which resulted in reduced mNeonGreen signal and lower levels of infection of neighboring cells. The size of the syncytia was also reduced in the DHHC9 knocked down cells compared to the control knocked down cells at 72 h post-infection (FIG. 6A). There was no measurable change in syncytia formation after knock-down of DHHC5, showing that DHHC9 plays a key role in the palmitoylation of the spike protein during SARS-CoV-2 infection.

Figure 7A:
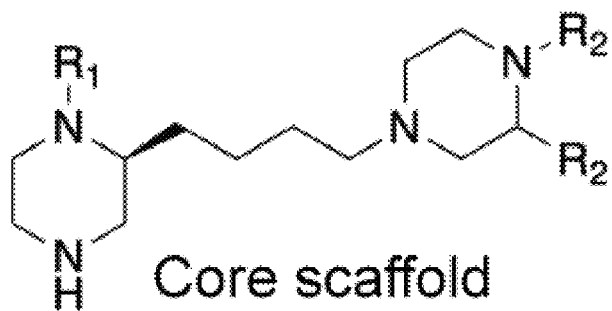
FIGS. 7A, 7B, 7C, 7D, 7E, 7F, 7G, 7H, and 7I show inhibition of SARS-CoV-2 infectivity by DHHC9 inhibitors.
Figure 7A:
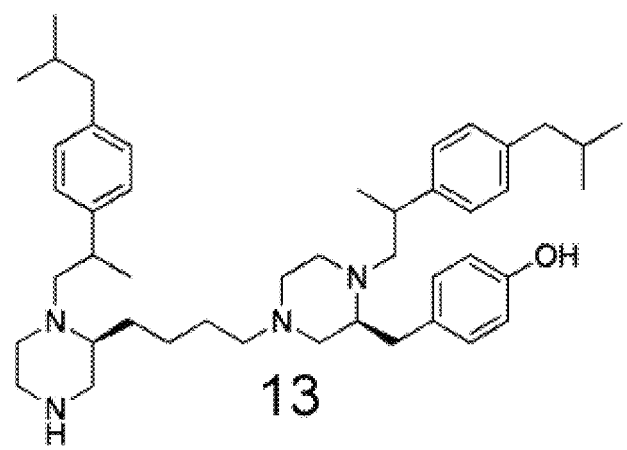
Figure 7A:
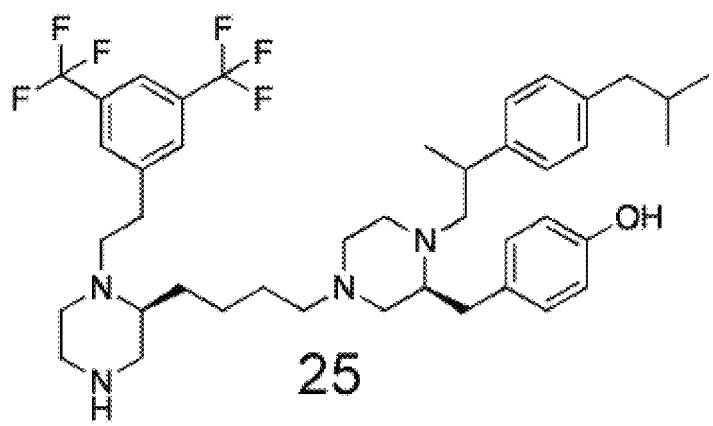

DHHC9 Inhibitors Inhibit SARS-CoV-2 Spike Palmitoylation, Fusogenicity and Infectivity Having identified DHHC9 as a SARS-CoV-2 spike protein palmitoylating enzyme, it was investigated whether inhibiting DHHC9 would inhibit SARS-CoV-2 infection. The availability of validated and specific PAT inhibitors are fairly limited. 2-bromopalmitate (2-BP), the most widely used PAT inhibitor promiscuously inhibit a wide range of enzyme utilizing active site cysteine residues. Previously, using a scaffold ranking approach to screen for novel inhibitors of the yeast homolog of DHHC9, a number of bis-piperazine backbone based compounds (Compound 1) were identified. Two leads, compounds 2 and 3, inhibited palmitoylation at low micromolar concentrations. Compound 2 has the lead functional group, 2-(3,5-bis-trifluoromethylphenyl)-ethyl, at positions R1 and R3, while compound 3 has 4-tert-butyl-cyclohexyl-methyl at the R1 position and 2-(3,5-bis-trifluoromethyl-phenyl)-ethyl at position R3 (FIG. 7A). The palmitoylation inhibitory potential of compounds 2 and 3 were evaluated against the SARS-CoV-2 spike protein.

Figure 7B:
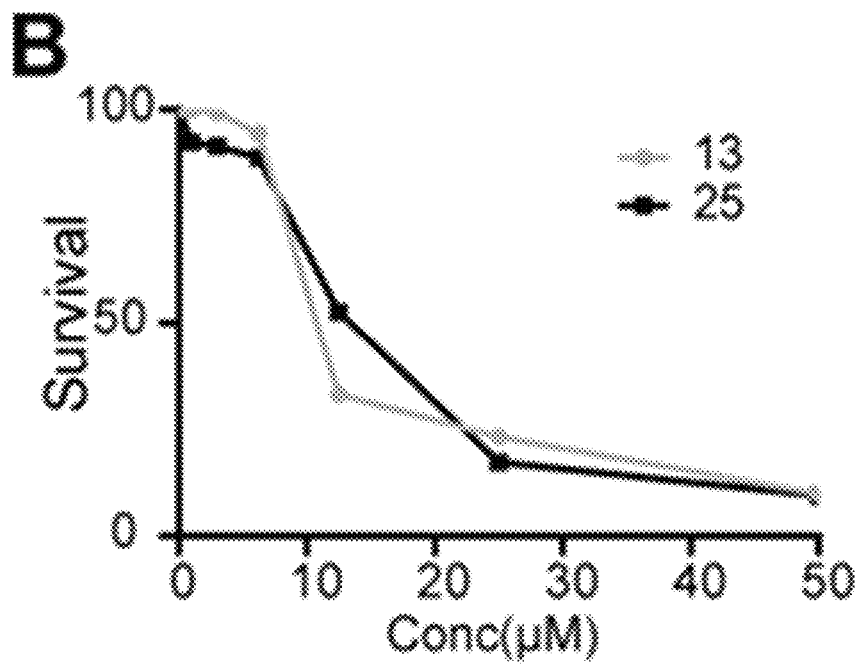
Figure 7C:
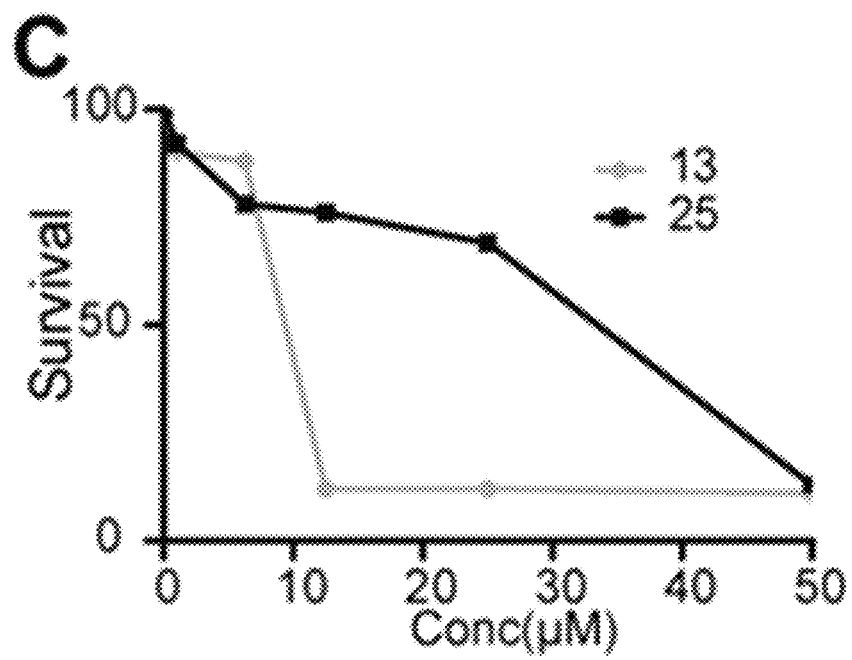
Figure 7D:
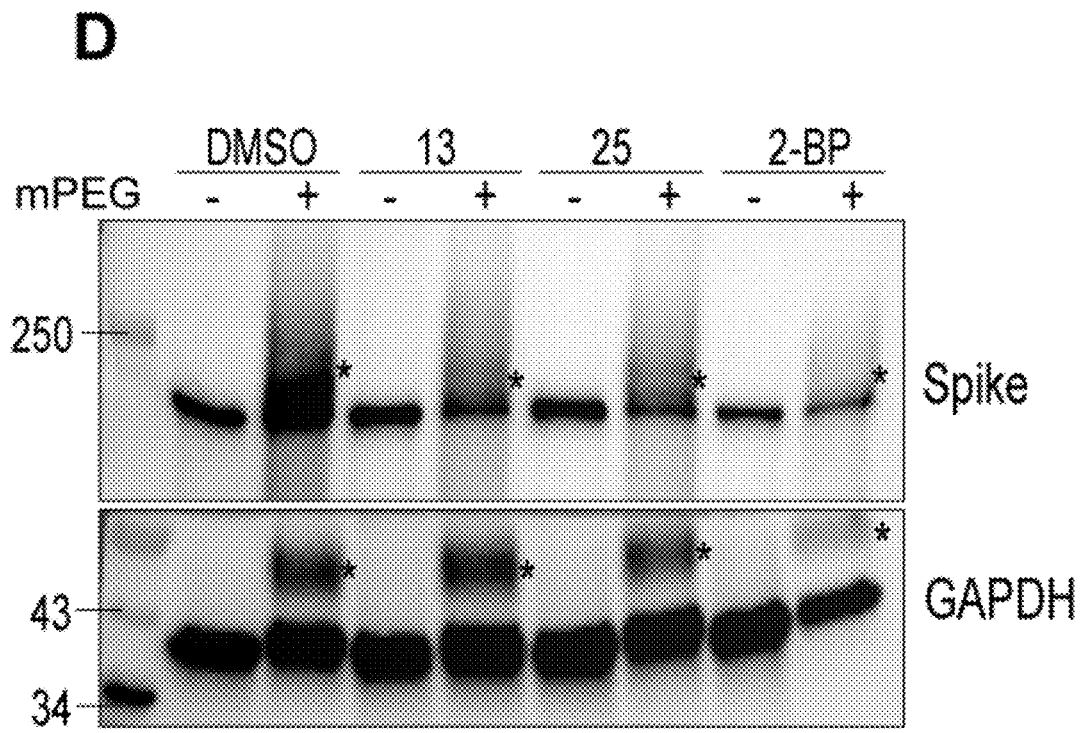

The compounds were first tested for toxicity on HEK293T and Caco-2 cells and found to have no observable toxicity at concentrations below 3 µM (FIGS. 7B and C, respectively). Next, it was examined whether compounds 2 and 3 inhibited the SARS-CoV-2 spike protein palmitoylation using APEGS assay. Compared to the vehicle control, compounds 2 and 3 (3 µM) reduced palmitoylation of the spike protein in HEK293T cells by 37% and 44% respectively (FIG. 7D). The non-specific PAT inhibitor, 2-BP, also inhibited spike palmitoylation, but required 10 µM concentration. In the same experiment, GAPDH palmitoylation is reduced by the non-specific inhibitor, 2-BP, but not by compounds 2 and 3 (FIG. 7D), consistent with the specificity previously observed for these compounds.

Figure 7E:
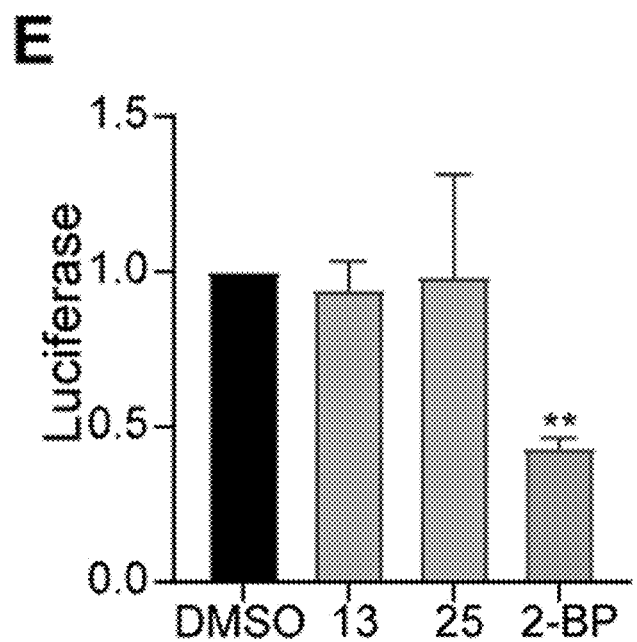
Figure 7F:
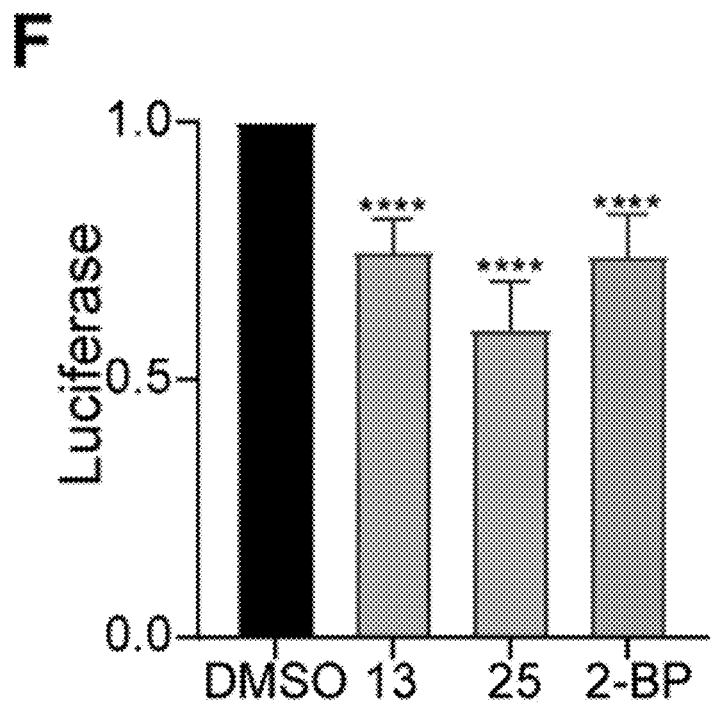
Figure 7G:
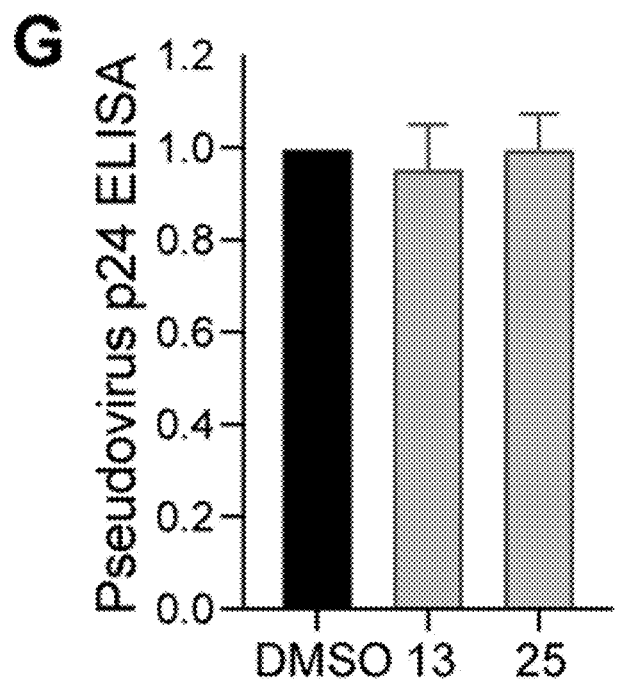
Figure 7H:
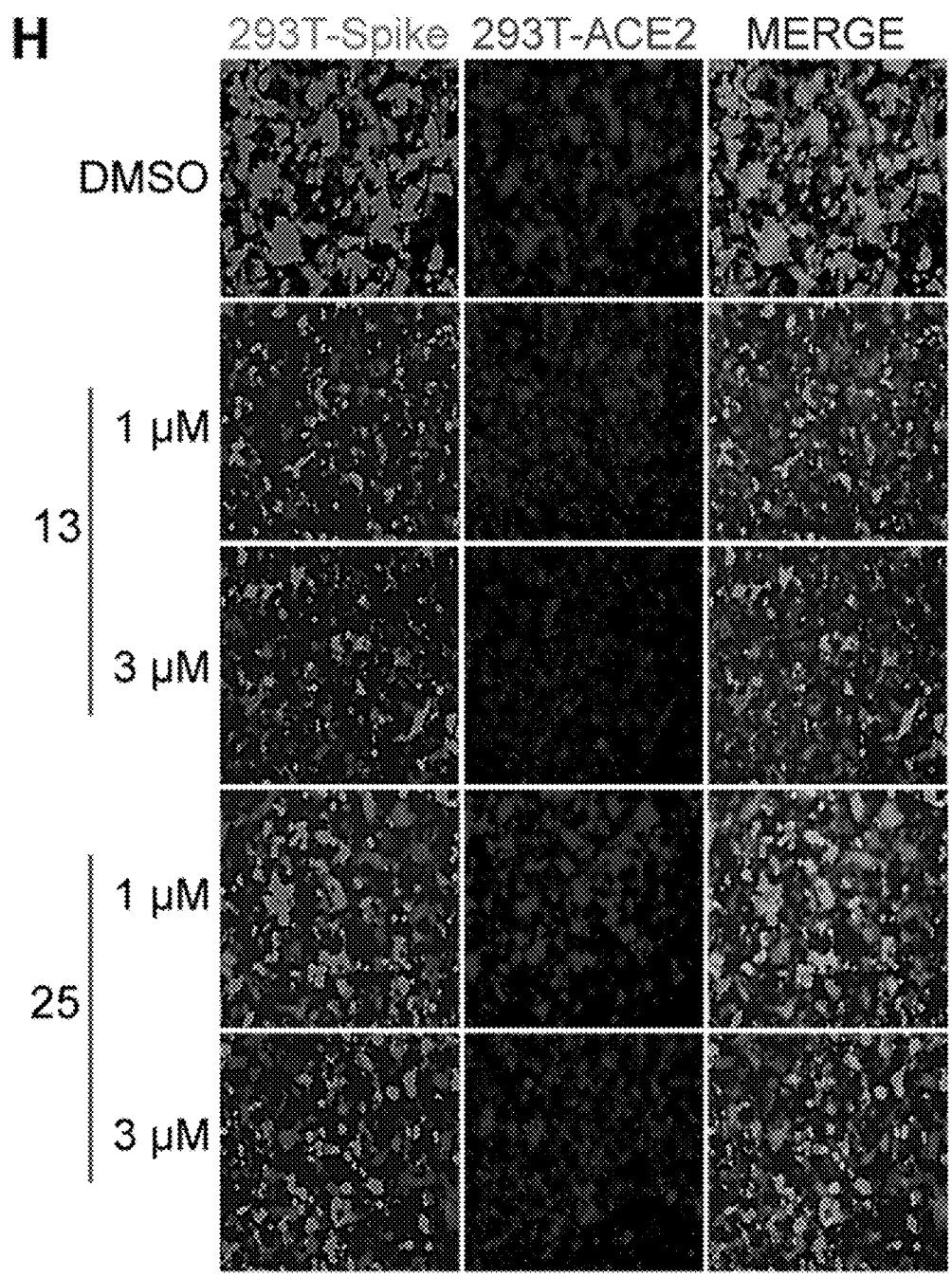
Figure 7I:
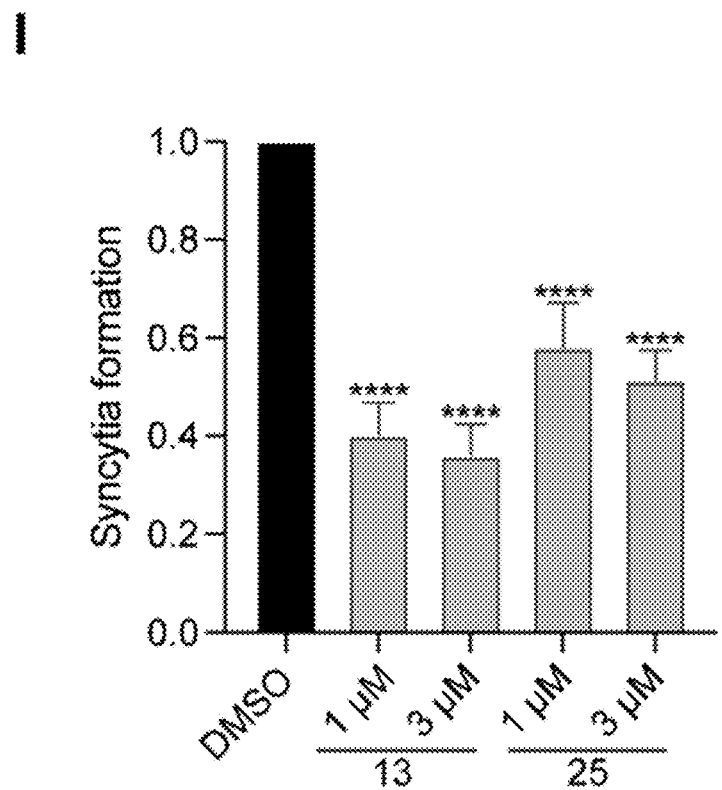

Next, the effect of these palmitoyltransferase inhibitors on the cellular entry and infectivity of SARS-COV-2 spike pseudotyped lentivirus on HEK293T-ACE2 cells. First, the recipient HEK293T-ACE2 was treated with inhibitors and found that there was no reduction in luciferase signal upon treatment with compounds 2 and 3 (FIG. 7E). However, 2-BP caused a significant reduction in pseudovirus infection, showing that it interferes with lentivirus endocytosis (FIG. 7E). This also signifies that compounds 2 and 3 do not affect any step downstream of infection. HEK293T cells were then treated with compounds 2, 3 or 2-BP and pseudovirus produced from these cells were tested for their ability to infect untreated HEK293T-ACE2 cells. In this case, a significant reduction in the luciferase signal was observed (FIG. 7F) showing that inhibition of spike palmitoylation resulted in a pseudovirus with reduced ability to infect cells. Under similar conditions, 2-BP also reduced luciferase signal significantly. Compounds 2 and 3 also do not reduce the quantity of pseudovirus released from the producer cells, showing that there is no measurable effect on lentivirus packaging and egress (FIG. 7G). Furthermore, inhibition of spike palmitoylation by compounds 2 and 3 reduces its fusogenicity in a syncytia formation assay. Treatment with compound 2 (1 µM and 3 µM) resulted in a 58% and 60% reduction in syncytia formation, respectively. Compound 3 (1 µM and 3 µM) similarly reduced syncytia formation by 45% and 50%, respectively (FIGS. 7H and I).

Compounds 2 and 3 Inhibit SARS-CoV-2 Infection in Cell Culture

Figure 8A:
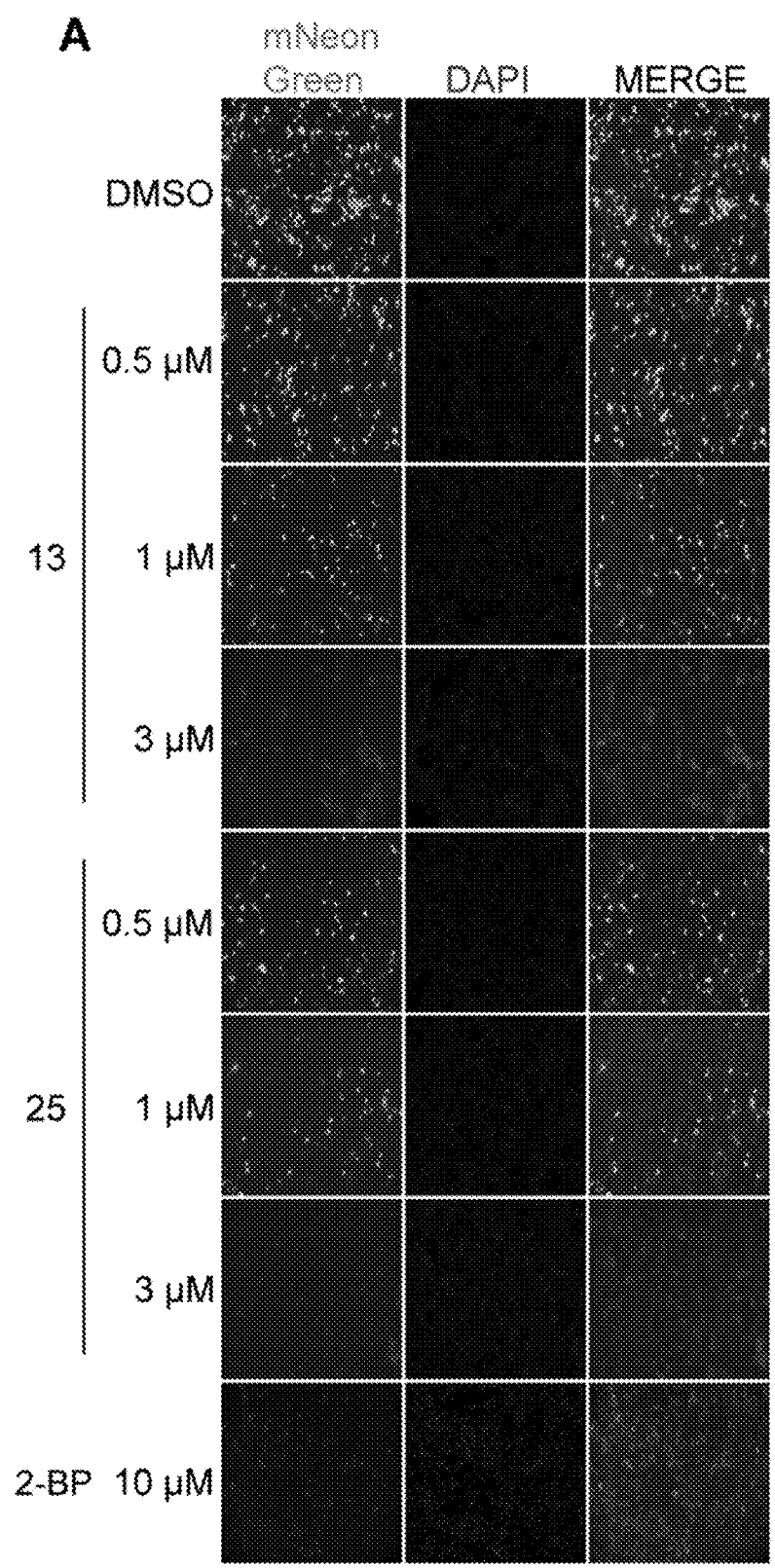
FIGS. 8A, 8B, and 8C show that Compounds 2 and 3 inhibit SARS-CoV-2 infection.
Figure 8B:
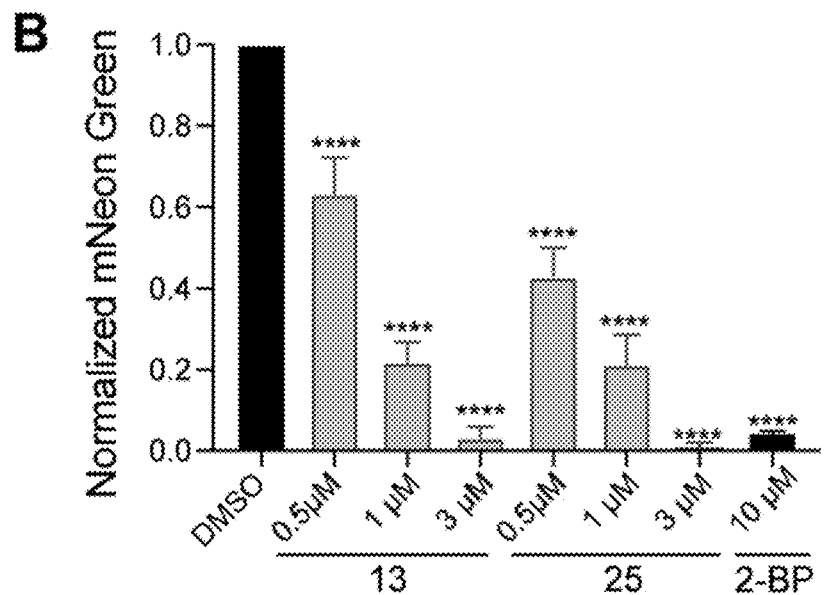
Figure 12:
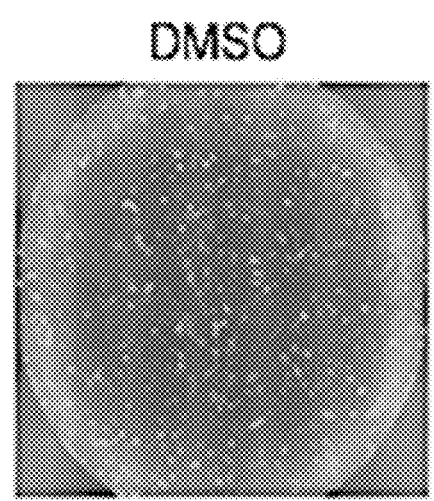
FIG. 12 shows additional images of FIG. 8A. Images of the entire well of the 96 well plate is provided to forego any bias in the region of interest photographed.
Figure 12:
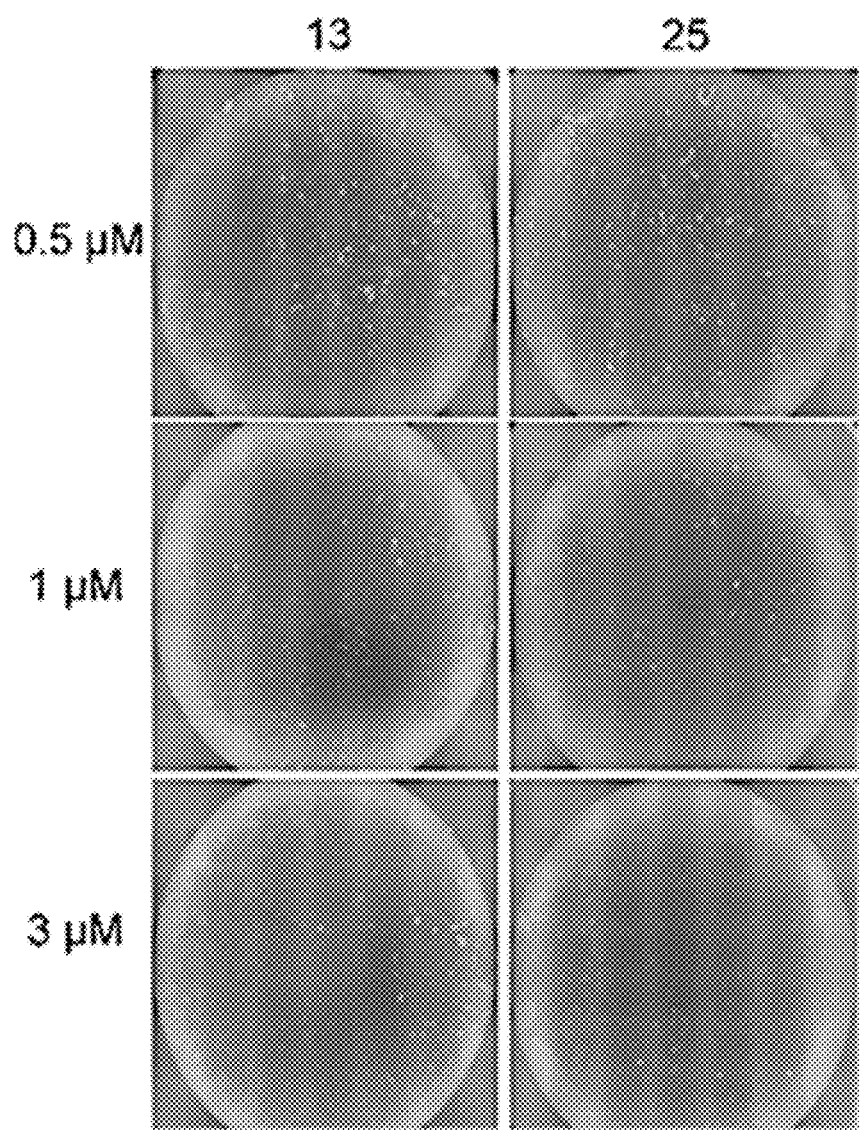

The effect of these palmitoyltransferase inhibitors was tested on SARS-CoV-2 infection using the SARS-CoV-2-mNG. Caco-2 cells pretreated with compounds 2, 3, or 2-BP and infected with SARS-CoV-2-mNG exhibited dose dependent reduction in mNeonGreen signal after 72 h of infection (FIG. 8A, B and FIG. 12). The size of the syncytia were also reduced in the inhibitor treated cells compared to the control vehicle treated cells (FIG. 8A). This shows that compounds 2 and 3 effectively inhibits SARS-CoV-2 spike protein palmitoylation causing a reduction in the infection competent virus released to subsequently infect neighboring cells.

Figure 8C:
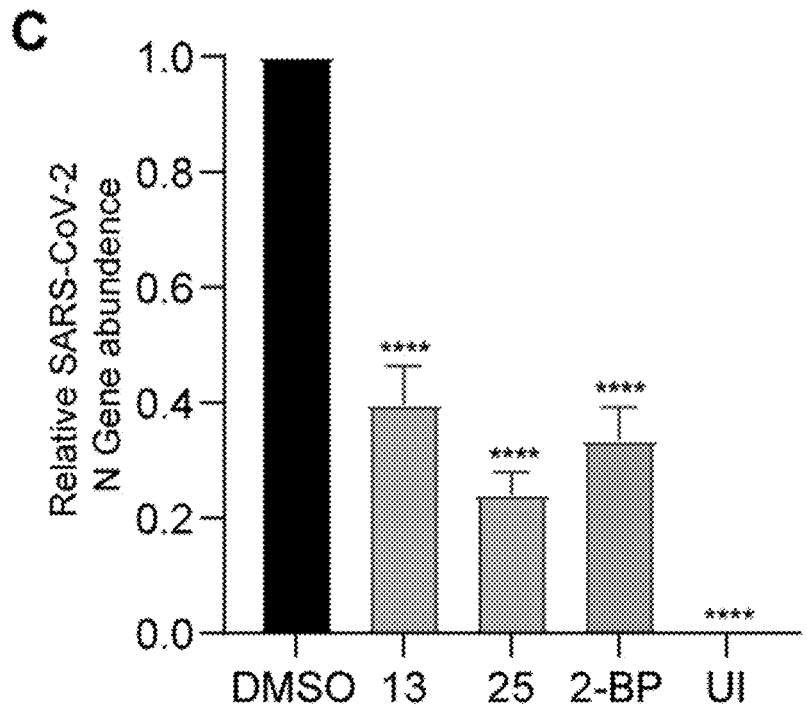
Figure 9:
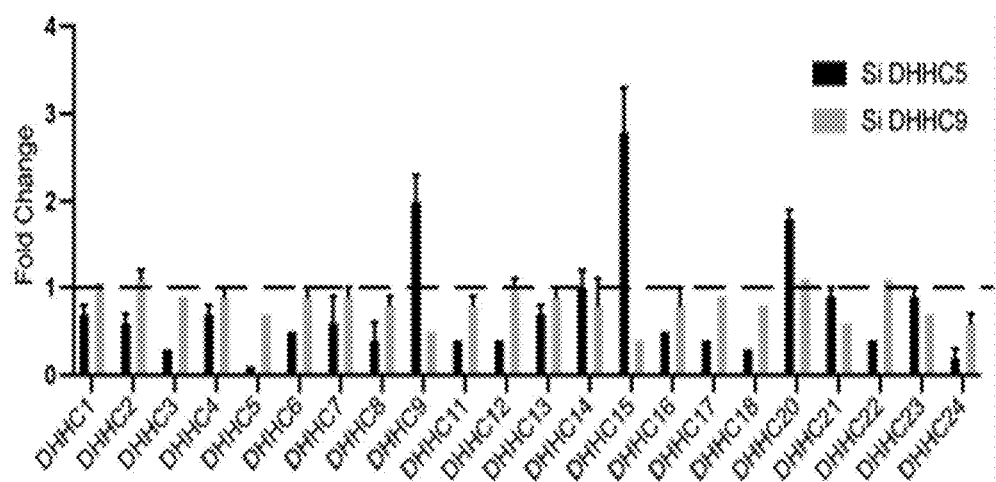
FIG. 9 shows that DHHC5 and DHHC9 acyltransferases were knocked down using siRNA for 72 h in HEK293T cells and the indicated acyltransferase mRNA levels were evaluated by RT-PCR.

Next, virus containing supernatants were collected 72 h after SARS-CoV-2 infection of Caco-2 cells pre-treated with the inhibitors and used to infect Vero-E6 ACE2 cells. After 24 h, infection was quantitated by measuring the appearance of the SARS-CoV-2 N gene by real-time RT-PCR. SARS-CoV-2 virus isolated from Caco-2 cells treated with compounds 2 and 3 resulted in a 60% and 76% reduction viral infection of Vero-E6 cells (FIG. 8C).

DISCUSSION

In this example, it was demonstrated that the SARS-CoV-2 spike protein is palmitoylated on a cluster of conserved cysteines residues on the cytosolic domains of the SARS-CoV-2 spike protein. Mutating all 10 cysteine residues to serine (ΔC) eliminates all detectable palmitoylation but mutating individual clusters of cysteines shows that not all cysteine residues are palmitoylated equivalently. For example, mutating clusters C1 (C1235, C1236), C2 (C1240, C1241, C1243), and C4 (C1253, C1254) significantly reduces, but does not eliminate spike palmitoylation. In contrast, spike palmitoylation is unaffected by mutating the C3 (C1248, C1249, C1250) cluster. Individual cysteine clusters are also functionally different. Mutating C1 and C2 clusters reduce infection of ACE-2 expressing cells to the same extent as ΔC, showing that palmitoylation of the juxtamembrane cysteines are the most important for infection. Mutating the C3 cluster does not reduce palmitoylation or influence infection. Interestingly, mutating the C4 cluster reduces overall palmitoylation, but does not reduce infection showing that palmitoylation of the C4 cysteines may have other roles in the viral life cycle.

Palmitoylation of SARS-CoV-2 spike occurs in the ER and Golgi and results in partitioning into detergent resistant, cholesterol and sphingolipid rich membrane microdomains. In contrast, palmitoylation defective spike is localized in detergent soluble membrane fractions and results in 35% less spike on the cell surface. It was also found that the ΔC mutant of the spike protein decreases surface expression by 40% and taken together, these results show that palmitoylation is important, but not essential for the surface expression of the spike protein. The spike protein appears to be able to access alternate trafficking routes depending on palmitoylation. It was also shown that palmitoylation is not required for ACE2 receptor binding. However, despite being capable of binding ACE2 and a modest decrease in membrane expression, virus harboring non-palmitoylated spike fail to infect host cells.

Since the palmitoylation sites of the SARS-CoV spike protein CRDs are in the vicinity of the membrane bilayer, the cytoplasmic tail folds back creating a membrane anchor. The palmitoylation of up to 10 cysteine residues creates a strong membrane anchor for the endodomains of the spike protein. The wild-type spike protein and its palmitoylation defective mutants were found to be expressed at approximately the same levels, and traffic to the plasma membrane and bind to ACE2 at the same levels. However, the ΔC and C2 cysteine mutants results in a decrease in spike protein trimerization.

Pre-fusion, the spike protein typically exists in a metastable conformation. Once it interacts with the host ACE2 receptor, extensive structural rearrangement of the S protein occurs, allowing the virus to fuse with the host cell membrane. This S2 domain directed fusion event requires a concerted cooperation between the different domains of the spike trimers Thus, conformational changes mediated by palmitoylation in the cytoplasmic endodomain of the spike protein impact the ability of the extracellular ectodomain to adopt the proper conformation required for efficient cell fusion showing a co-operation between the ecto and endodomains. Alternatively, palmitoylation simply concentrates the spike protein in membrane microdomains, thus facilitating trimer formation.

S-acylation of viral proteins requires the host cell palmitoylation machinery that, depending on the cell type, consists of up to 23 individual DHHC PAT genes. Identification of the DHHC protein or proteins that palmitoylate the SARS-CoV-2 spike has begun to emerge from several lines of investigation. First, a comprehensive interactome study uncovered an interaction between the SARS-CoV-2 spike protein and Golga7, an auxiliary protein for DHHC5, DHHC9, and additional DHHC proteins. All animal reservoirs of coronaviruses express DHHC9 and DHHC20, and observations from the knockdown and overexpression of DHHC8, 9, and 20 further show these PATs in the palmitoylation of SARS-CoV-2 spike protein. Several approaches were used to show that DHHC9 plays a major role in palmitoylating the SARS-CoV-2 spike protein. Knockdown of DHHC9 resulted in a decrease in spike protein palmitoylation, pseudovirus fusion, syncytia formation, and a 55% and 80% reduction of SARS-CoV-2 infection at 48 h and 72 h post inoculation, respectively. Surprisingly, it was observed that knockdown of DHHC5 resulted in an increase in palmitoylation of the spike protein. On further investigation, it was found that knockdown of DHHC5 resulted in compensatory upregulation of DHHC9, DHHC15 and DHHC20 PATs. This shows that in addition to DHHC9, DHHC15 or DHHC20 can also palmitoylate the spike protein.

This example shows that inhibitors of palmitoylation were developed into a new class of antivirals. Commonly used inhibitors such as 2-bromopalmitte show little specificity, hitting a wide range of thiol containing enzymes. A high throughput palmitoylation assay was developed and used to screen a chemical library consisting of 68 unique scaffolds and 30 million unique structures for inhibition of the yeast ortholog of DHHC9. Two compounds based on a bis-piperazine backbone (compounds 2 and 3) were selected to be tested for inhibition of SARS-CoV-2 spike palmitoylation and viral infection. It was found that both compounds decreased spike protein palmitoylation, pseudovirus infection and syncytia formation. Further, experiments on SARS-CoV-2 infection established the robust inhibitory effect of compounds 2 and 3 on progeny virion formation.

Materials and Methods

Plasmids and HIV-1 Derived Pseudovirus Generation

Plasmids used in this study for the production of pseudo-typed virus were a gift from Jesse D. Bloom's lab (BEI Resources #NR52516, NR52517, NR52518 and NR52519). The HDM-IDTSpike-fixK (BEI catalog number NR-52514) plasmid expressing a codon-optimized spike from SARS-CoV-2 strain Wuhan-Hu-1 (Genbank NC_045512) under a CMV promoter, was used as the wild-type spike and all the mutagenesis was performed on this codon-optimized spike clone. Third Generation Lentivirus EGFP plasmid, pLJM1-EGFP, was a gift from David Sabatini (Addgene #19319). $3^{rd}$ generation lentivirus were produced using the flowing packaging plasmids, which were a gift from Didier Trono's lab, pMDL (Addgene #12251), pRev (Addgene #12253) and pMD2.G (Addgene #12259) (61).

HIV-1 derived virus particles pseudotyped with full length wild-type and mutant SARS-CoV-2 spike protein were generated by transfecting HEK293T cells as previously described (62). Briefly, plasmids expressing the HIV-1 gag and pol (pHDM-Hgpm2), HIV-1 rev (pRC-CMV-rev1b), HIV-1 Tat (pHDM-tat1b), the SARS CoV2 spike (pHDM-SARS-CoV-2 Spike) and a luciferase/ZsGreen reporter (pHAGE-CMV-Luc2-IRES-ZsGreen-W) were co-transfected into HEK293T cells at a 1:1:1:1.6:4.6 ratio using CalPhos mammalian transfection kit (TaKaRa Clontech, Mountain View, CA #631312) according to manufacturer's instructions. Fresh media was added after 18 hours and 60 hours later, culture supernatant was collected, clarified by passing through 0.45 um filter and used freshly.

Cell Culture

Human female embryonic kidney HEK293T cells (ATCC) were grown in Dulbecco modified Eagle's medium (DMEM) supplemented with 10% fetal bovine serum (FBS) (Sigma, #F4135) and Penicillin-Streptomycin (Gibco, #15140148). HEK293T cells constitutively expressing human ACE2 (HEK293T-ACE2 cells) obtained from BEI Resources (#NR52511) were grown in the same media supplemented with hygromycin (100 µg/ml). HEK293T cells constitutively expressing EGFP (HEK293T-EGFP) were established by transducing HEK293T cells with the pLJM1-EGFP containing lentivirus. Lentivirus was produced by transfecting $10^6$ HEK293T cells on a 60 mm plate with pMDL, pRev and pVSVG using CalPhos mammalian transfection kit (TaKaRa Clontech). Next day, fresh media was added, then two days after transfection, the supernatant was harvested, and filtered 0.45-µm filter to remove cell debris. The filtered supernatant containing lentiviral vectors was used to transduce 293T cells seeded one day before. 48 hours later, the cells were selected in DMEM supplemented with 2 µg/ml puromycin for one week. The puromycin-resistant population of HEK293T-EGFP cells was found to constitutively express EGFP by fluorescent microscopy. These HEK293T-EGFP cells were used as donor cells in syncytium formation assays. Caco-2 (human colon epithelial cells) cells, obtained from ATCC (HTB-37), were grown in Minimum Essential Medium (Gibco #11095080.) media supplemented with 20% fetal bovine serum (Sigma, #F4135), Penicillin-Streptomycin (Gibco, #15140148), 1× non-essential amino acid solution (Cytiva, SH3023801) and 10 mM sodium pyruvate (Gibco, #11360070). All cell lines were incubated at 37° C. in the presence of 5% $CO_2$.

CoV Spike Protein Sequence Alignment

Amino acid sequences of the S protein used in the alignment were obtained from UniProKB. The accession numbers are SARS-CoV-2 (P0DTC2), SARS-CoV-1 (P59594), Bat RaTG13 (A0A6B9WHD3), MERS (K9N5Q8), MHV [A-59] (P11224), HCoV-OC43 (P36334), HCoV-229E (P15423), TGEV (P07946) and IBV (P11223). Alignment of these sequences was done using Clustal Omega (https://www.ebi.ac.uk/Tools/msa/clustalo/).

Site-Directed Mutagenesis

All mutagenesis was done using Q5 Site-directed Mutagenesis Kit Protocol (NEB #E0554S) according to the manufacturer's instructions using primers in Table 1. All mutagenesis was confirmed with sequencing (GENEWIZ, South Plainfield, NJ).

TABLE 1

Mutagenic primers used
Transfection
For pseudo-typed virus production, HEK293T cells were transfected using the CalPhos mammalian transfection kit (TaKaRa Clontech) according to the manufacturer's instructions. For the syncytia formation assay, HEK293T- GFP cells were transiently transfected with wild-type and mutant spike plasmids using TransIT-X2 transfection reagent (Mirus #MIR 6000) according to the manufacturer's instructions, and fresh media was added after 6 hours.

| Primer | Sequence |
|---|---|
| C1_F | TATAATGCTGAGCAGCATGACAAGCTG (SEQ ID NO. 11) |
| C1_R | GTCACCATGACTATAGCG (SEQ ID NO. 12) |

TABLE 1-continued

Mutagenic primers used
Transfection
For pseudo-typed virus production, HEK293T cells were
transfected using the CalPhos mammalian transfection kit
(TaKaRa Clontech) according to the manufacturer's instructions.
For the syncytia formation assay, HEK293T- GFP cells were
transiently transfected with wild-type and mutant spike
plasmids using TransIT-X2 transfection reagent (Mirus #MIR 6000)
according to the manufacturer's instructions, and fresh media
was added after 6 hours.

| Primer | Sequence |
|---|---|
| C2_F | AGCAGTCTCAAAGGCTGTTGCTCTTG (SEQ ID NO. 13) |
| C2_R | GCTGCTGCTTGTCATGCAGCACAG (SEQ ID NO. 14) |
| C3_F | TCTAGCGGCTCTTGCTGCAAATTC (SEQ ID NO. 15) |
| C3_R | GCTACTGCCTTTGAGACAGCTGCA (SEQ ID NO. 16) |
| C4_F | TTGCGGCTCTAGCAGCAAATTCGATG (SEQ ID NO. 17) |
| C4_R | GAGCAACAGCCTTTGAGAC (SEQ ID NO. 18) |
| ΔC_F | AAAGGCAGTAGCTCTAGCGGCTCTAGCAGCAAATTCGATGAGGACGATTC (SEQ ID NO. 19) |
| ΔC_R | GAGACTGCTGCTGCTGCTTGTCATGCTGCTCAGCATTATAGTCACCATG (SEQ ID NO. 20) |

SARS-CoV-2 Spike Pseudotyped Virus Entry

The assay was done as previously described with minor modification. Briefly, 96-Flat bottom well plates were coated with poly-D-lysine (Gibco, #A3890401) and seeded with $1.25 \times 10^4$ HEK293T-ACE2 or Caco-2 cells per each well. After 12 h, pseudotyped virus with wild type and mutant spike (with no polybrene) were used for infection. After 48 hours, Steady-Glo Reagent (Promega #E2620) equal to the volume of culture medium in each well was added as per manufacturer's instructions, cells were allowed to lyse for 5 minutes and then luminescence measured with a microtiter plate reader (Biotek, Winooski, VT).

Pseudovirus Egress

In order to quantitate HIV based pseudovirus egress from HEK293T cells, ELISA was performed against HIV p24 (TaKaRa Clontech #632200) according to manufacturer's instructions. Briefly, pseudotyped virus containing cell culture supernatant was collected, diluted 1:20, ELISA performed, and absorbance measured at 450 nm using a microtiter plate reader (Biotek, Winooski, VT).

Immunoblotting

Whole cell lysates were prepared using RIPA Lysis Buffer (Thermo scientific #89900) supplemented with a protease inhibitor cocktail (Roche #11836170001) for 30 min on ice and then sonicated three times at an amplitude setting of 50 with pulses of 15 s on and 15 s off on a Qsonica Q700 sonicator. The lysates were clarified by centrifugation at 13,000 X g for 15 min at 4° C. Protein concentrations were estimated using Pierce BCA protein assay kit (Thermo scientific #23225) as per manufactural instructions and equal concentration of proteins resolved appropriate SDS PAGE gels. SDS polyacrylamide gels were transferred on Nitrocelluose membranes (GE) by Wet transfer BioRad System at 300 Amps for 90 min at 4° C., membranes were blocked with 5% non-fat milk for 1 hour at room temperature (RT) and were incubated with primary antibodies diluted in PBST solution at 4° C. overnight. All primary antibodies used in this study are listed in Table 3.

TABLE 3

Primary antibodies used

| Antibody | Source | Catalog Number |
|---|---|---|
| Spike S2 | GeneTex | GTX632604 |
| Spike S1 | Sino Biological | 40591-MM42 |
| ACE2 | Novus | NBP2-67692 |
| GAPDH | Santa Cruz | sc-47724 |
| Calnexin | Novus | NB 300-518 |
| Calnexin | Cell Signaling | 2679P |
| FLAG | Sigma-Aldrich | F1804 |
| FLAG | Sigma-Aldrich | F7425 |
| MYC | Cell Signaling | 71D10 |
| MYC | Cell Signaling | 9B11 |
| DHHC9 | Sigma-Aldrich | HPA031814 |
| DHHC5 | Sigma-Aldrich | HPA014670 |
| β-Actin | Protein-tech | HRP-60008 |
| GM130 | Invitrogen | PA5-95727 |
| GM130 | R&D | AF8199 |

Membranes were washed with PBST for 5 minutes, 3 times and subsequently incubated with appropriate secondary antibodies. Blots were then washed three times with PBST for 5 minutes each wash. The immunoreactive bands were developed using Super Signal West Pico chemiluminescent substrate (Thermo scientific #34078) or Super Signal West Femto chemiluminescent substrate (Thermo scientific #34095) depending on the signal strength. Blots were developed on a Bio-Rad ChemiDoc XRS+ System.

Co-Immunoprecipitation (Co-IP)

Whole cell lysates were prepared using Pierce IP Lysis Buffer (Pierce #87788) supplemented with a protease inhibitor cocktail for 30 min on ice and then sonicated three times at an amplitude setting of 30 with pulses of 15 s on and 15 s off on a Qsonica Q700 sonicator at 4° C. The lysates were then clarified by centrifugation at 13,000×g for 15 minutes at 4° C. and protein concentrations estimated by BCA reaction. For IP, 300 μg of the prepared lysate was incubated with the appropriate antibody (3 μg) and pulled down using protein A Sepharose 6 MB (GE healthcare #17-0469-01). All primary antibodies used in this study are listed in Table 3. The immunoprecipitates were washed three times with lysis buffer at 4° C. and resolved on SDS-PAGE followed by immunoblotting. Wherever mentioned, light-chain-specific secondary antibodies were used to avoid heavy chain bands in WB of co-IP experiments.

Acyl-PEGyl Exchange Gel-Shift (APEGS) Assay

To assess the level of protein S-palmitoylation on the SARS-CoV2 spike protein, APEGS was performed. In brief, HEK293T cells transfected with appropriate plasmids were lysed with the following buffer, 4% SDS, 5 mM EDTA, in triethanolamine buffer (TEA) pH 7.3 with protease inhibitors and PMSF (5 mM). After centrifugation at 20,000×g for 15 min, proteins in the supernatant were reduced with 25 mM tris(2-carboxyethyl)phosphine (TCEP, Thermo Scientific, #20490) for 1 hour at RT, and free cysteine residues were blocked with 20 mM N-ethyl maleimide (NEM, Sigma #E3876) for 3 hours at RT. To terminate the NEM reaction and wash any residual NEM, pre-chilled methanol:chloroform:$H_2O$ (4:1.5:3) was added to the reaction. This wash was repeated three times. Next, the proteins were re-suspended in TEA with 4% SDS and 5 mM EDTA, then incubated in buffer containing 0.2% Triton X-100, 5 mM EDTA, 1 M $NH_2OH$, pH 7.0 for 1 hour at RT to cleave palmitoylation thioester bonds. The reaction was terminated as above, and proteins re-suspended in TEA with 4% SDS were PEGylated with 1.33 mM mPEGs (10 kDa, Sunbright, #ME050) for 2 hours at RT to label palmitoylation sites. The reaction was terminated as above; proteins were re-suspended with TEA buffer with 4% SDS. Protein concentration was measured by BCA protein assay. Thereafter, SDS PAGE sample buffer was added, and samples were heated at 70° C. for 10 minutes and run on a 7.5% gel for Spike and 12% for GAPDH.

Syncytium Formation Assay

HEK293T-EGFP cells (donor cell) were transiently transfected with wild-type and mutant spike plasmids using TransIT-X2 transfection reagent (Mirus #MIR 6000). HEK293T-ACE2 and HEK293T (as a negative control) were stained with CellTracker Red CMTPX Dye (Invitrogen #C34552) according to manufacturer's instructions. 6 h after transfection, the HEK293T-ACE2 cells were treated with accutase cell detachment reagent and added to the HEK293T-EGFP cells transfected with spike protein, at a 1:1 ratio. 48 h after transfection, cells were fixed and imaged using Keyence BX700 fluorescent microscope. Images were quantified using ImageJ.

Compound Synthesis and Characterization

Bis-piperidines 2 and 3 were synthesized using solid-phase chemistry, purified by RP-HPLC, and characterized by LCMS and 1H NMR as previously described. The compounds were additionally recharacterized by LCMS before performing all biological assays. For LCMS analysis a Shimadzu 2010 LCMS system, consisting of a LC-20AD binary solvent pumps, a DGU-20A degasser unit, a CTO-20A column oven, and a SIL-20A HT auto sampler. A Shimadzu SPD-M20A diode array detector was used for detections. A full spectra range of 190-800 nm was obtained during analysis. Chromatographic separations were obtained using a Phenomenex Gemini NX-C18 analytical column (5 μm, 50×4.6 mm ID). The column was protected by a Phenomenex Gemini-NX C18 column SecurityGuard (5 μm, 4×3.0 mm ID). All equipment was controlled and integrated by Shimadzu LCMS solutions software version 3. Mobile phases for LCMS analysis were HPLC grade or LCMS grade obtained from Sigma Aldrich and Fisher Scientific. The mobile phases consisted of a mixture of LCMS grade acetonitrile and water (both with 0.1% formic acid for a pH of 2.7). The initial setting for analysis was at 5% acetonitrile (v/v), linearly increasing to 95% acetonitrile over 6 minutes. The gradient was then held at 95% acetonitrile for 2 minutes until linearly decreasing to 5% over 1 minute. From there, the gradient was held until stop for an additional 3 minutes. The total run time was equal to 12 minutes. The total flow rate was set to 0.5 mL/minute. The column oven and flow cell temperature for the diode array detector were set at 40° C. The auto sampler temperature was held at 15° C. 10 μl was injected for analysis. 4-(((2S)-1-(2-(4-isobutylphenyl) propyl)-4-(4-((2S)-1-(2-(4-isobutylphenyl) propyl) piperazin-2-yl) butyl) piperazin-2-yl) methyl) phenol (Compound 2) OC1=CC=C(C[C@@H]2N(CC(C3=CC=C(CC(C)C)C=C3)C)CCN(CCCC[C@@H]4N(CC(C5=CC=C(CC(C)C)C=C5)C)CCNC4)C2)C=C1 LCMS (ESI+) Calculated exact mass for C45H68N4O: 680.54 found [M+H]+: 681.55. Retention Time: 4.78 minutes. 90.1% purity by 214 nM.

4-(((2S)-4-(4-((S)-1-(3,5-bis(trifluoromethyl)phenethyl) piperazin-2-yl) butyl)-1-(2-(4-isobutylphenyl) propyl) piperazin-2-yl) methyl) phenol (Compound 3) OC1=CC=C(C[C@@H]2N(CC(C3=CC=C(CC(C)C)C=C3)C)CCN(CCCC[C@@H]4N(CC C5=CC(C(F)(F)F)=CC(C(F)(F)F)=C5)CCNC4)C2)C=C1 LCMS (ESI+) Calculated exact mass for C42H56F6N4O: 746.44, found [M+H]+:747.40. Retention Time: 4.722 minutes. 90.4% purity by 214 nM.

Cellular Toxicity Assay

The XTT Cell Proliferation Kit II (Roche #11465015001) was used for assessing cellular toxicity following manufacturer's instruction. DMSO was used as a vehicle for all compounds and appropriate dilution of DMSO only was used as a control.

Gene Silencing

Genes were silenced using siRNAs obtained from IDT, DHHC5 (#290128941) and DHHC9 (#290128950). For each gene, a combination of three siRNAs was used. HEK293T cells were seeded on 24 well plate 24 h before transfection. Transfection of these siRNAs was done using TransIT-X2 (Mirus #MIR 6000) according to the manufacturer's instructions. Silencing efficacy was checked using qPCR using SYBR Green real-time reagents (Invitrogen #4367659) and immunoblotting.

RNA extraction and RT-qPCR

Total RNA was isolated using the RNeasy minikit (Qiagen #74106) following manufacturer's instructions. On-column DNase digestion was performed by using an RNase-free DNase set (Qiagen #79254). The extracted RNA concentration was estimated using a NanoDrop spectrophotometer (Thermo Scientific), and 1 μg RNA was reverse transcribed by using the High-Capacity cDNA reverse transcription kit (Applied Biosystems #4368814) with random primers, according to the manufacturer's instructions. For real-time quantitative reverse transcription-PCR (qRT-PCR), the synthesized cDNA was diluted 1:20 and used as a template with Power SYBR Green PCR Master Mix (Applied Biosystems #4367659) on an ABI Prism 7500 detection system (Applied Biosystems). All RNA levels were normalized to β-actin mRNA levels and calculated as the delta-delta threshold cycle (ΔΔCT). Primers used in this study are listed in Table 2.

TABLE 2

Real-time primers used

| Primer | Sequence1 | Sequence2 |
|---|---|---|
| DHHC1 | CAAGCCCTCCAACAAGACG (SEQ ID NO. 21) | CCAAAGCCGATCACAGCAAAG (SEQ ID NO. 22) |
| DHHC2 | AACACTGGCGAACAAGTTGTG (SEQ ID NO. 23) | AGATGGGAAGATCCTTGGCTG (SEQ ID NO. 24) |
| DHHC3 | CCACTTCCGAAACATTGAGCG (SEQ ID NO. 25) | CCACAGCCGTCACGGATAAA (SEQ ID NO. 26) |
| DHHC4 | CCTGACTTGTGGAACCAATCC (SEQ ID NO. 27) | GCACCTCACGTTCTTTGGAAAC (SEQ ID NO. 28) |
| DHHC5 | CACCTGCCGCTTTTACCGT (SEQ ID NO. 29) | CGGCGACCAATACAGTTATTCAC (SEQ ID NO. 30) |
| DHHC6 | AGTCTGCCAAGCATACAAGGC (SEQ ID NO. 31) | CCAGTGGTGCTAAAAGGAGAAAC (SEQ ID NO. 32) |
| DHHC7 | CTGACCGGGTCTGGTTCATC (SEQ ID NO. 33) | CATGACGAAAGTCACCACGAA (SEQ ID NO. 34) |
| DHHC8 | GTATCCAGGTCCGCATGAAGT (SEQ ID NO. 35) | AGCGTGGTTCAGCACGTAG (SEQ ID NO. 36) |
| DHHC9 | CCCAGGCAGGAACACCTTTT (SEQ ID NO. 37) | CCGAGGAATCACTCCAGGG (SEQ ID NO. 38) |
| DHHC11 | GGTGCAGACCCTGATAGTCG (SEQ ID NO. 39) | GCACGTATGGATCTTTCCTCAC (SEQ ID NO. 40) |
| DHHC12 | GTGCTGACCTGGGGAATCAC (SEQ ID NO. 41) | CTGCACATTCACGTAGCCA (SEQ ID NO. 42) |
| DHHC13 | ACCCCACTCTTATTGATGGAGA (SEQ ID NO. 43) | TGTCTGCCCATTTACATCTGTC (SEQ ID NO. 44) |
| DHHC14 | TGTGATAACTGCGTAGAACGGT (SEQ ID NO. 45) | CGTGGGTGATAACGAATGCAA (SEQ ID NO. 46) |
| DHHC15 | GGTGCCAGTGCTCGTTATTGT (SEQ ID NO. 47) | AAGACGTAGGCATAGTAGGACC (SEQ ID NO. 48) |
| DHHC16 | ACTCCGGGGTCTAGTACAGC (SEQ ID NO. 49) | CCAGCGGATCACGTTGTCT (SEQ ID NO. 50) |
| DHHC17 | GGCCCGGATGAGTACGATAC (SEQ ID NO. 51) | TCCAAGAGGTTCACCATATCCA (SEQ ID NO. 52) |
| DHHC18 | TGACGGCCTTCATCTTCGC (SEQ ID NO. 53) | CTGGACCACGAGCCTTTGAT (SEQ ID NO. 54) |
| DHHC19 | TTGCTGCCTTCAATGTGGTG (SEQ ID NO. 55) | CGGAGCCTTGATGTAAGATGC (SEQ ID NO. 56) |
| DHHC20 | CGCACCCACGTTTTCATACG (SEQ ID NO. 57) | TCTGGCATACTCATTCTGGTTTG (SEQ ID NO. 58) |
| DHHC21 | TGTTGTTGACCCACATGGTTG (SEQ ID NO. 59) | GAGGCCCTCACTAAGGCAA (SEQ ID NO. 60) |
| DHHC22 | GAGGCACGACCATCACTGTTT (SEQ ID NO. 61) | ACAGCGGAGATGTAGGCCA (SEQ ID NO. 62) |
| DHHC23 | TCTGGATGAAGGGTGTGATCG (SEQ ID NO. 63) | GCTCCCCTAAGCCAAGGAA (SEQ ID NO. 64) |
| DHHC24 | CTGGCACAGTTTGCCTTGG (SEQ ID NO. 65) | CAGGGACCCAGGTCATAGGAG (SEQ ID NO. 66) |
| SARS-CoV-2 N | CACATTGGCACCCGCAATC (SEQ ID NO. 67) | GAGGAACGAGAAGAGGCTTG (SEQ ID NO. 68) |

Immunofluorescence Assay (IFA) and Proximity Ligation Assay (PLA)

Cells were grown on eight chamber glass slides and treated as described in the results. After appropriate incubations, the cells were fixed using 4% paraformaldehyde for 15 min, and permeabilized with 0.2% Triton X-100 in PBS for 20 min. The slides were then washed, blocked with Image-iT FX signal enhancer (Invitrogen #I36933) for 30 minutes at 37° C. and incubated with primary antibodies for 1 h at 37° C. All primary antibodies used in this study are listed in Table 3. After this, the slides were washed three times in PBS and incubated with corresponding fluorescent dye-conjugated secondary antibodies for 30 minutes at 37° C. PLA was performed according to the manufacturer's instructions using the following kits and reagents: Duolink in-situ PLA Probe Anti-Rabbit PLUS (Sigma-Aldrich #DUO92002), Duolink in-situ PLA Probe Anti-Mouse MINUS (Sigma-Aldrich #DUO92004), Duolink in-situ Detection Reagents Red (Sigma-Aldrich #DUO92008). After completion of IFA or PLA, slides were mounted using mounting medium containing DAPI and observed either by a Keyence BZ-X fluorescence microscope.

Surface Immunofluorescence Assay

To detect the amount of spike protein localizing to the surface of the cell, HEK293T cells were seeded in 8-chamber glass bottomed slides and transfected with appropriate plasmids. Cells were washed and treated with freshly prepared 0.1% paraformaldehyde and incubated for 10 minutes at 4° C. Thereafter, the cells were washed two times with DMEM with 5% FBS and incubated with anti-spike antibody diluted (1:200) in DMEM with 5% FBS and 0.1% Sodium Azide for 1 h at 37° C. Next, cells were washed four times with DMEM with 5% FBS at 4° C. for 10 minutes and incubated with appropriate secondary antibody (1:500) for 30 minutes at 4° C. Finally, the cells were washed, anti-fade reagent added and imaged using a Keyence BX700 microscope.

SARS-CoV-2 Virus Stock Preparation and Titration with Plaque-Based Assays

All replication competent SARS-CoV-2 experiments were performed in a biosafety level 3 laboratory (BSL-3) at the University of South Florida. All viral stocks were produced and isolated from supernatants of Vero-E6 ACE2 cells, cultured in T175 culture flasks to a confluency of 80-90%, and infected with an original passage 2 (P2) SARS-CoV-2 or SARS-CoV-2-mNG (SARS-CoV-2 stably encoding mNeonGreen) virus, at MOI of 0.1 for 72 h, in 10 ml MEM supplemented with 5% FBS. SARS-CoV-2 was obtained from BEI Resources (NR52281), while SARS-CoV-2-mNG was a kind gift from Dr. PEI-Yong Shi from the University of Texas Medical Branch, Galveston, TX, USA. Supernatants were harvested, cleared of cell debris by centrifugation (500 g, 10 min) and filtration (0.45 μm), mixed with 10% SPG buffer (ATCC #MD9692), aliquoted and stored at −80° C. Viral titers were quantified by determining the number of individual plaques forming units after 72 h of infection on confluent Vero-E6-ACE2 expressing cells. In brief, viral stocks were serially diluted (10-fold) in serum-free medium and inoculated on $1 \times 10^5$ Vero E6-ACE2 cells in triplicates in a 48 well plate.

SARS-CoV-2 Infection

All SARS-CoV-2 infections were performed using the same passage 3 SARS-CoV-2 or SARS-CoV-2-mNG virus stocks. Caco-2 cells seeded to a confluency of 70 to 80%, were washed twice in warm serum-free medium and inoculated with the indicated MOI of the appropriate virus, diluted in serum-free medium (5 ml for T75; 2 ml for T25; 1 ml for 6-well plates). Two hours after inoculation cells were washed with complete medium and infection was allowed to proceed for the indicated time points in DMEM supplemented with 2.5% FBS. After infection, media with respective drugs were added and incubated for 72 h. Images were quantified using ImageJ.

Drug Treatments

For drug treatment, cells were treated with indicated concentrations of 2-BP (Sigma, #238422) or compounds 2 and 3 dissolved in DMSO, 12 h prior to infection. Post-infection, cells were continued to be incubated in presence of the respective drugs for the indicated time.

Statistical Analysis and Reproducibility

Statistical analysis was performed using GraphPad Prism 9 (San Diego, CA). For two groups, means were compared by two-tailed unpaired Student's t test. For multiple groups, analysis was done by one-way ANOVA with Dunnett correction for multiple comparisons. P value of <0.05 was considered statistically significant. Specific statistical test results are indicated in each figure: *, $p<0.05$; , $p<0.01$; *=$p<0.001$; ****=$p<0.0001$.

SEQUENCES

1. SEQ ID NO. 1-PAT consensus amino acid sequence
DHHC

2. SEQ ID NO. 2-SARS2 SPIKE
AIVMVTIMLCCMTSCCSCLKGCCSCGSCCKFDEDD

3. SEQ ID NO. 3-SARS1 SPIKE
AIVMVTILLCCMTSCCSCLKGACSCGSCCKFDEDD

4. SEQ ID NO. 4-Bat RaTG13
AIIMVTIMLCCMTSCCSCLKGCCSCGSCCKFDEDD

5. SEQ ID NO. 5-MERS SPIKE
LALCVFFILCCTGCGTNCMGKLKCNRCCDRYEEY

6. SEQ ID NO. 6-MHV (A-59)
AVCVLLFFICCCTGCGSCCFKKCGNCCDEYGGH

7. SEQ ID NO. 7-HCoV-OC43
AMLVLLFFICCCTGCGTSCFKKCGGCCDDYTGY

8. SEQ ID NO. 8-HCoV-229E
IFVVSMLLLCCCSTGCCGFFSCFASSIRGCCESTK

9. SEQ ID NO. 9-TGEV
IFCIPLLLFCCCSTGCCGCIGCLGSCCHSICSRRQ

10. SEQ ID NO. 10-IBV
LGWVFFMTGCCGCCCGCFGIMPLMSKCGKKSSYYT

11. SEQ ID NO. 11-C1_F
TATAATGCTGAGCAGCATGACAAGCTG

12. SEQ ID NO. 12-C1_R
GTCACCATGACTATAGCG

13. SEQ ID NO. 13-C2_F
AGCAGTCTCAAAGGCTGTTGCTCTTG

14. SEQ ID NO. 14-C2_R
GCTGCTGCTTGTCATGCAGCACAG

15. SEQ ID NO. 15-C3_F
TCTAGCGGCTCTTGCTGCAAATTC

16. SEQ ID NO. 16-C3_R
GCTACTGCCTTTGAGACAGCTGCA

17. SEQ ID NO. 17-C4_F
TTGCGGCTCTAGCAGCAAATTCGATG

| SEQUENCES |
|---|
| 18. SEQ ID NO. 18-C4_R<br>GAGCAACAGCCTTTGAGAC |
| 19. SEQ ID NO. 19-ΔC_F<br>AAAGGCAGTAGCTCTAGCGGCTCTAGCAGCAAATTCGATGAGGACGATTC |
| 20. SEQ ID NO. 20-ΔC_R<br>GAGACTGCTGCTGCTGCTTGTCATGCTGCTCAGCATTATAGTCACCATG |
| 21. SEQ ID NO. 21-DHHC 1 SEQUENCE 1<br>CAAGCCCTCCAACAAGACG |
| 22. SEQ ID NO. 22-DHHC 1 SEQUENCE 2<br>CCAAAGCCGATCACAGCAAAG |
| 23. SEQ ID NO. 23-DHHC 2 SEQUENCE 1<br>AACACTGGCGAACAAGTTGTG |
| 24. SEQ ID NO. 24-DHHC 2 SEQUENCE 2<br>AGATGGGAAGATCCTTGGCTG |
| 25. SEQ ID NO. 25-DHHC 3 SEQUENCE 1<br>CCACTTCCGAAACATTGAGCG |
| 26. SEQ ID NO. 26-DHHC 3 SEQUENCE 2<br>CCACAGCCGTCACGGATAAA |
| 27. SEQ ID NO. 27-DHHC 4 SEQUENCE 1<br>CCTGACTTGTGGAACCAATCC |
| 28. SEQ ID NO. 28-DHHC 4 SEQUENCE 2<br>GCACCTCACGTTCTTTGGAAAC |
| 29. SEQ ID NO. 29-DHHC 5 SEQUENCE 1<br>CACCTGCCGCTTTTACCGT |
| 30. SEQ ID NO. 30-DHHC 5 SEQUENCE 2<br>CGGCGACCAATACAGTTATTCAC |
| 31. SEQ ID NO. 31-DHHC 6 SEQUENCE 1<br>AGTCTGCCAAGCATACAAGGC |
| 32. SEQ ID NO. 32-DHHC 6 SEQUENCE 2<br>CCAGTGGTGCTAAAAGGAGAAAC |
| 33. SEQ ID NO. 33-DHHC 7 SEQUENCE 1<br>CTGACCGGGTCTGGTTCATC |
| 34. SEQ ID NO. 34-DHHC 7 SEQUENCE 2<br>CATGACGAAAGTCACCACGAA |
| 35. SEQ ID NO. 35-DHHC 8 SEQUENCE 1<br>GTATCCAGGTCCGCATGAAGT |
| 36. SEQ ID NO. 36-DHHC 8 SEQUENCE 2<br>AGCGTGGTTCAGCACGTAG |
| 37. SEQ ID NO. 37-DHHC 9 SEQUENCE 1<br>CCCAGGCAGGAACACCTTTT |
| 38. SEQ ID NO. 38-DHHC 9 SEQUENCE 2<br>CCGAGGAATCACTCCAGGG |
| 39. SEQ ID NO. 39-DHHC 11 SEQUENCE 1<br>GGTGCAGACCCTGATAGTCG |
| 40. SEQ ID NO. 40-DHHC 11 SEQUENCE 2<br>GCACGTATGGATCTTTCCTCAC |
| 41. SEQ ID NO. 41-DHHC 12 SEQUENCE 1<br>GTGCTGACCTGGGGAATCAC |
| 42. SEQ ID NO. 42-DHHC 12 SEQUENCE 2<br>CTGCACATTCACGTAGCCA |
| 43. SEQ ID NO. 43-DHHC 13 SEQUENCE 1<br>ACCCCACTCTTATTGATGGAGA |
| 44. SEQ ID NO. 44-DHHC 13 SEQUENCE 2<br>TGTCTGCCCATTTACATCTGTC |
| 45. SEQ ID NO. 45-DHHC 14 SEQUENCE 1<br>TGTGATAACTGCGTAGAACGGT |
| 46. SEQ ID NO. 46-DHHC 14 SEQUENCE 2<br>CGTGGGTGATAACGAATGCAA |
| 47. SEQ ID NO. 47-DHHC 15 SEQUENCE 1<br>GGTGCCAGTGCTCGTTATTGT |
| 48. SEQ ID NO. 48-DHHC 15 SEQUENCE 2<br>AAGACGTAGGCATAGTAGGACC |
| 49. SEQ ID NO. 49-DHHC 16 SEQUENCE 1<br>ACTCCGGGGTCTAGTACAGC |
| 50. SEQ ID NO. 50-DHHC 16 SEQUENCE 2<br>CCAGCGGATCACGTTGTCT |
| 51. SEQ ID NO. 51-DHHC 17 SEQUENCE 1<br>GGCCCGGATGAGTACGATAC |
| 52. SEQ ID NO. 52-DHHC 17 SEQUENCE 2<br>TCCAAGAGGTTCACCATATCCA |
| 53. SEQ ID NO. 53-DHHC 18 SEQUENCE 1<br>TGACGGCCTTCATCTTCGC |
| 54. SEQ ID NO. 54-DHHC 18 SEQUENCE 2<br>CTGGACCACGAGCCTTTGAT |
| 55. SEQ ID NO. 55-DHHC 19 SEQUENCE 1<br>TTGCTGCCTTCAATGTGGTG |
| 56. SEQ ID NO. 56-DHHC 19 SEQUENCE 2<br>CGGAGCCTTGATGTAAGATGC |
| 57. SEQ ID NO. 57-DHHC 20 SEQUENCE 1<br>CGCACCCACGTTTTCATACG |
| 58. SEQ ID NO. 58-DHHC 20 SEQUENCE 2<br>TCTGGCATACTCATTCTGGTTTG |
| 59. SEQ ID NO. 59-DHHC 21 SEQUENCE 1<br>TGTTGTTGACCCACATGGTTG |
| 60. SEQ ID NO. 60-DHHC 21 SEQUENCE 2<br>GAGGCCCTCACTAAGGCAA |
| 61. SEQ ID NO. 61-DHHC 22 SEQUENCE 1<br>GAGGCACGACCATCACTGTTT |
| 62. SEQ ID NO. 62-DHHC 22 SEQUENCE 2<br>ACAGCGGAGATGTAGGCCA |
| 63. SEQ ID NO. 63-DHHC 23 SEQUENCE 1<br>TCTGGATGAAGGGTGTGATCG |
| 64. SEQ ID NO. 64-DHHC 23 SEQUENCE 2<br>GCTCCCCTAAGCCAAGGAA |
| 65. SEQ ID NO. 65-DHHC 24 SEQUENCE 1<br>CTGGCACAGTTTGCCTTGG |
| 66. SEQ ID NO. 66-DHHC 24 SEQUENCE 2<br>CAGGGACCCAGGTCATAGGAG |
| 67. SEQ ID NO. 67-SARS-CoV-2N SEQUENCE 1<br>CACATTGGCACCCGCAATC |
| 68. SEQ ID NO. 68-SARS-CoV-2N SEQUENCE 2<br>GAGGAACGAGAAGAGGCTTG |

What is claimed is:

1. A method of treating a coronavirus in a subject said method comprising administering to the subject a therapeutically effective amount of a palmitoyltransferase (PAT) inhibitor.

2. The method of claim 1, wherein the inhibitor has the structure

[structure showing piperazine-linked compound with R1, R2, R3 substituents]

wherein each of R1, R2, and R3 is independently selected from the group consisting of i. [4-isobutylphenyl ethyl structure]

ii. [3,5-bis(trifluoromethyl)phenyl ethyl structure]

iii. [4-tert-butylcyclohexyl methyl structure]

iv. [4-hydroxyphenyl methyl structure]

v. [benzyl structure]

vi. [naphthalenylmethyl structure]

vii. [adamantyl ethyl structure]

3. The method of claims 1, wherein the PAT inhibitor inhibits DHHC9.

4. The method of claim 1, wherein the PAT inhibitor inhibits palmitoylation of one or more cysteine amino acids of a glycoprotein on the coronavirus.

5. The method of claim 4, wherein the glycoprotein is a coronaviral spike protein.

6. The method of claim 5, wherein the PAT inhibitor inhibits palmitoylation at C1235, C1236, C1240, C1241, and/or C1243 of a SARS-CoV2 spike protein.

7. The method of claim 1, wherein the inhibitor comprises

Compound 2

[structure of Compound 2]

or

Compound 3

[structure of Compound 3]

8. A method of preventing a coronavirus from entering a cell using a palmitoyltransferase (PAT) inhibitor, wherein the PAT inhibitor inhibits a palmitoylation of a spike protein.

9. The method of claim 8, wherein the inhibitor has the structure wherein each of R1, R2, and R3 is independently selected from the group consisting of i.

ii.

iii.

iv.

v.

vi.

vii.

10. The method of claims 9, wherein the PAT inhibitor inhibits DHHC9.

11. The method of claim 9, wherein the PAT inhibitor inhibits palmitoylation of one or more cysteine amino acids of a glycoprotein on the coronavirus.

12. The method of claim 11, wherein glycoprotein is a coronaviral spike protein.

13. The method of claim 12, wherein the PAT inhibitor inhibits palmitoylation at C1235, C1236, C1240, C1241, and/or C1243 of a SARS-CoV2 spike protein.

14. The method of claim 9, wherein the inhibitor comprises

Compound 2 or

Compound 3

* * * * *